United States Patent [19]

Salzmann et al.

[11] Patent Number: 4,791,207
[45] Date of Patent: Dec. 13, 1988

[54] ENANTIOSELECTIVE PROCESS FOR PRODUCING 1-BETAMETHYLCARBAPENEM ANTIBIOTIC INTERMEDIATES

[75] Inventors: Thomas N. Salzmann, North Plainfield; Lelia M. Fuentes; Ichiro Shinkai, both of Westfield, all of N.J.

[73] Assignee: Merck & Co., Inc., Rahway, N.J.

[21] Appl. No.: 45,724

[22] Filed: May 4, 1987

Related U.S. Application Data

[63] Continuation of Ser. No. 837,103, Mar. 6, 1986, abandoned, which is a continuation-in-part of Ser. No. 717,742, Mar. 29, 1985, abandoned.

[51] Int. Cl.$^4$ ................................................ C07F 5/02
[52] U.S. Cl. .................................... 548/110; 540/200
[58] Field of Search ........................................ 548/110

[56] References Cited

U.S. PATENT DOCUMENTS 4,298,486  11/1981  Horodysky et al. ............ 548/110 Y

OTHER PUBLICATIONS

Hsiao et al., Chemical Abstracts, vol. 104 (1985) 186189n.
Hsaio, Chi Nung et al., Tetrahedron Ltrs, CA Abstract, 26, (40) 1985.
Couquelet et al., Eur. J. Med. Chem. Chim Ther. vol. 18, pp. 301-305 (1983).
Offenhauer et al., J. Org. Chem. vol. 33 (2) pp. 775-777 (1968).
Rao et al., J. Org. Chem. vol. 47 (17) pp. 3265-3269 (1982).
Masamune et al., J. Am. Chem. Soc. vol. 103 (6) pp. 1566-1568 (1981).
Meyers et al., J. Am. Chem. Soc. vol. 103 (14) pp. 4278-4279 (1981).
Horder et al., Chem. Commun. vol. 10, pp. 485-486 (1967).
Baxter et al., J. Chem. Soc., Perkin Trans, vol. 1, pp. 1809-1812 (1983).
Baker et al., J. Chem. Soc. Chem. Comm. vol. 3, pp. 147-148 (1983).
Kuwojima et al., Tetrahedron Letters, vol. 21 (44) pp. 4291-4294 (1980).
Akiba et al., Tetrahedron Letters, vol. 22 (49) pp. 4961-4964 (1981).
McCarthy, Tetrahedron Letters, vol. 23 (41) pp. 4199-4202 (1982).
Jarglis et al., Tetrahedron Letters, vol. 23 (37) pp. 3781-3784 (1982).
Genvair et al., Tetrahedron Letters, vol. 25, pp. 2279-2286 (1984).
Evans et al., J. Am. Chem. Soc. vol. 101 (20) pp. 6120-6123 (1979).
Meltz et al., Tetrahedron Letters, vol. 24 (42) pp. 4507-4510 (1983).
Wada, Chemistry Letters, pp. 153-156 (1981).
Muraham et al., Chemistry Letters, pp. 241-244 (1982).
Mukaiyama et al., Chemistry Letters, pp. 1193-1196 (1981).
Synthesis Communications vol. 9 (6) pp. 585-528 (1979).
Nelson, Diss. Abstr. Int. B, vol. 41 (8) pp. 3036-3037 (1981).
Mukaiyama et al., Kagaku (Kyoto) vol. 37, (11) pp. 853-855 (1982).
Tetrahedron, vol. 40, No. 8, pp. 1281-1390 (1984).
JACS, vol. 103, No. 11, pp. 3099-3111 (1981).
JACS, vol. 103, pp. 2127-2129 (1981).

*Primary Examiner*—Richard L. Raymond
*Attorney, Agent, or Firm*—Robert J. North; Hesna J. Pfeiffer

[57] ABSTRACT

A process is described for the stereochemically controlled synthesis of intermediates useful in producing 1-betamethylcarbapenem antibiotics.

6 Claims, 2 Drawing Sheets

ENANTIOSELECTIVE PROCESS FOR PRODUCING 1-BETAMETHYLCARBAPENEM ANTIBIOTIC INTERMEDIATES

This is a continuation of application Ser. No. 837,103, filed Mar. 6, 1986, now abandoned, which in turn is a continuation-in-part of application Ser. No. 717,472, filed Mar. 29, 1985, now abandoned.

BACKGROUND OF THE INVENTION

1. Field of the Invention

This invention relates to a stereochemically controlled process for producing 1-betamethyl carbapenem antibiotic intermediates involving reacting a beta lactam with a chiral thia- or oxazolidinone enolate to preferentially produce a beta-methyl intermediate which can be transformed into a carbapenem antibiotic.

BRIEF DESCRIPTION OF DISCLOSURES IN THE ART

Since the discovery of thienamycin,

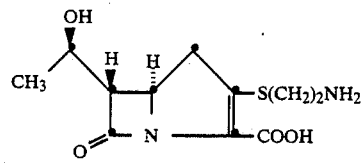

an extremely potent broad spectrum antibiotic, disclosed and claimed in commonly assigned U.S. Pat. No. 3,950,357, a large amount of research activity has been conducted in the medicinal chemistry area for other active analogs not having its associated deficiencies, i.e. chemical instability at high concentration and susceptability to renal dipeptidase.

In addition to the N-formimidoyl derivative of thienamycin, disclosed and claimed in commonly assigned U.S. Pat. No. 4,194,047, among some of the more promising analogs that have been developed are the 1-betamethyl compounds of structure (I), i.e.,

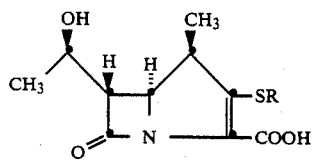

in which the 1-methyl group is in the beta configuration and R is a radical known in the antibiotic art.

Synthesis of the above 1-beta methyl analogs is desired in large quantities for derivatization and pharmacological evaluation and requires introduction of the beta-methyl substituent in a manner designed to yield a high percentage of the beta-methyl intermediate prior to ring closure.

A published procedure by Shih et al. in *Heterocycles*, Vol. 21, No. 1, pp. 29–40 (1984) describes a process for alkylating the 4-alkyl side chain of certain in azetidine-2-ones to produce a mixture of the alpha-and beta-methyl epimers in about a 4:1 molar ratio.

Desirably, a pilot plant or commercial synthesis should achieve higher beta/alpha epimeric molar ratios than this.

There are a variety of disclosed processes involving stereoselective aldol condensations including: D. A. Evans et al., *JACS* Vol. 103, No. 11, 1981, pp. 3099–3114, which describes stereoselective aldol condensations using boron enolates; D. A. Evans et al., *JACS* (1981), 103, 2129–2131 which describes chiral enolates containing 2-oxazolidinones as chiral auxiliaries in enantioselective aldol condensations; D. A. Evans and L. R. McGee in *JACS* (1981), 103, pp. 2876–2878, which describes the use of zirconium enolates containing 2-oxazolidinone chiral auxiliaries in erythro-selective aldol condensations; Evans et al. in *JACS* (1982), Vol. 104, No. 6, pp. 1737–1739, which describes the utility of lithium and sodium enolates derived from N-acyl oxazolidinones in diastereoselective alkylation; P. J. Reider, et al. in *Tetrahedran Letters*, Vol. 23, No. 4, pp. 379–382 and 2293–2296 (1982) which describe a method of β-lactam alkylation using 4-acetoxy-2-azetidinone as the alkylating agent and a variety of silyl enol ethers; Yamamoto et al. in *Tet. Lett.* 1980, 4607–10 discloses the preparation of zirconium enolates from the corresponding lithium enolates and demonstrates their effectiveness in aldol condensations; "Asymmetric Synthesis", Vol. 3, James D. Morrison, Editor, Academic Press, Inc., New York, 1984, Chapter 1, by D. A. Evans, "Stereoselective Alkylation Reactions of Chiral Metal Enolates" describes the utility of chiral enolates broadly in chiral synthesis; . . . Mukaiyama et al. in *Chem. Lett.* No. 11, pp. 1799–802 (1983); ibid., No. 3, pp. 297–8 (1983); ibid, No. 12, pp. 1903–6 (1982); and JP No. 77145448, describe 3-acyl-thiazolidine-2-thiones in anantioselective synthesis; Fujita et al. in *Tennen Yuki Kagobutsu Toronka; Koen Yoshishu*, Vol. 26, pp. 476–83 (1983) (Japanese) and *Acta Crystallogr.*, Sect. B, 1980, Vol., No. B36, pp. 1709–10, describe synthetic studies on virginiamycin and 3-(p-bromobenzoyl)-1,3-thiazolidine-2-thione, respectively.

Japanese reference: Kokai No. 60-19763, Jan. 31, 1985, illustrates related aldol condensation utilizing silyl enol ethers employing non-chiral oxazolidinones.

However, none of these references specifically teach the introduction of a carbon chain onto an azetidinone ring system directly resulting in a carbon chain methyl substituent in the desired beta configuration.

It is therefore an object of this invention to provide a steroselective process for producing intermediates useful in making 1-betamethylcarbapenem antibiotics. It is further an object of this invention to provide a process for producing intermediates in high yield having the necessary 1-beta methyl sterochemistry, prior to ring closure to the carbapenem ring system, in which the products contain the beta methyl/alpha methyl epimers in a molar ratio greater than one. These and further objects of the invention will become obvious from the accompanying disclosure as set forth herein.

SUMMARY OF THE INVENTION

It has been found that by condensing an azetidinone with an Z-enolate containing a chiral 2-thia- or oxazolidinone moiety, intermediates of desired stereochemistry can be obtained which are useful in the synthesis of 1-β-methyl-carbapenem antibiotics.

In accordance with the invention there is provided a composition of matter of the formula:

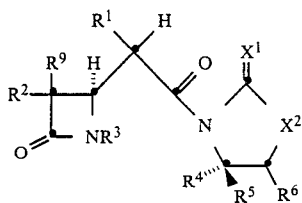

wherein $X^1$ and $X^2$ are independently S or O, R' is $C_1$-$C_4$ alkyl or alkoxyl, $R^2$ and $R^9$ are independently selected from hydrogen, linear, branched or cyclic $C_1$-$C_4$ alkyl, unsubstituted or substituted with fluoro, hydroxy, or protected hydroxy, with the proviso that both $R^2$ and $R^9$ are not unsubstituted alkyl, $R^3$ is H or easily removable protecting group, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical.

Specifically provided are compounds of the formula:

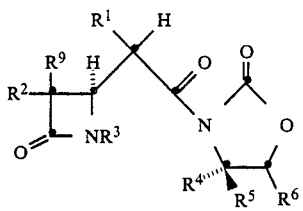

wherein R' is $C_1$-$C_4$ alkyl or alkoxyl, $R^2$ and $R^9$ are independently selected from hydrogen, linear, branched or cyclic $C_1$-$C_4$ alkyl, unsubstituted or substituted with fluoro, hydroxy, or protected hydroxy, with the proviso that both $R^2$ and $R^9$ are not unsubstituted alkyl, $R^3$ is H or easily removable protecting group, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl; with the proviso that $R^4$ and $R^5$ are not identical.

Note that as used herein, Structure IIA, and the like, refers to the generalized structure containing $X^1$ and $X^2$, whereas the absence of "A", refers to a structure where $X^1$ and $X^2$ are independently O or S in a specific compound.

Further provided is a compound of the formula:

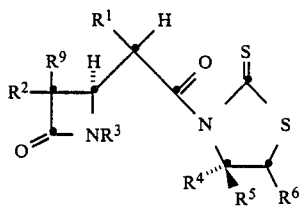

wherein $R^1$ is $C_1$-$C_4$ lower alkyl or alkoxyl, $R^2$ and $R^9$ are independently selected from hydrogen, $C_1$-$C_4$ linear, branched or cyclic alkyl, unsubstituted or substituted with fluoro, hydroxy, or protected hydroxy, with the proviso that both $R^2$ and $R^9$ are not unsubstituted alkyl, $R^3$ is H or easily removable protecting group, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical.

Figure 1:
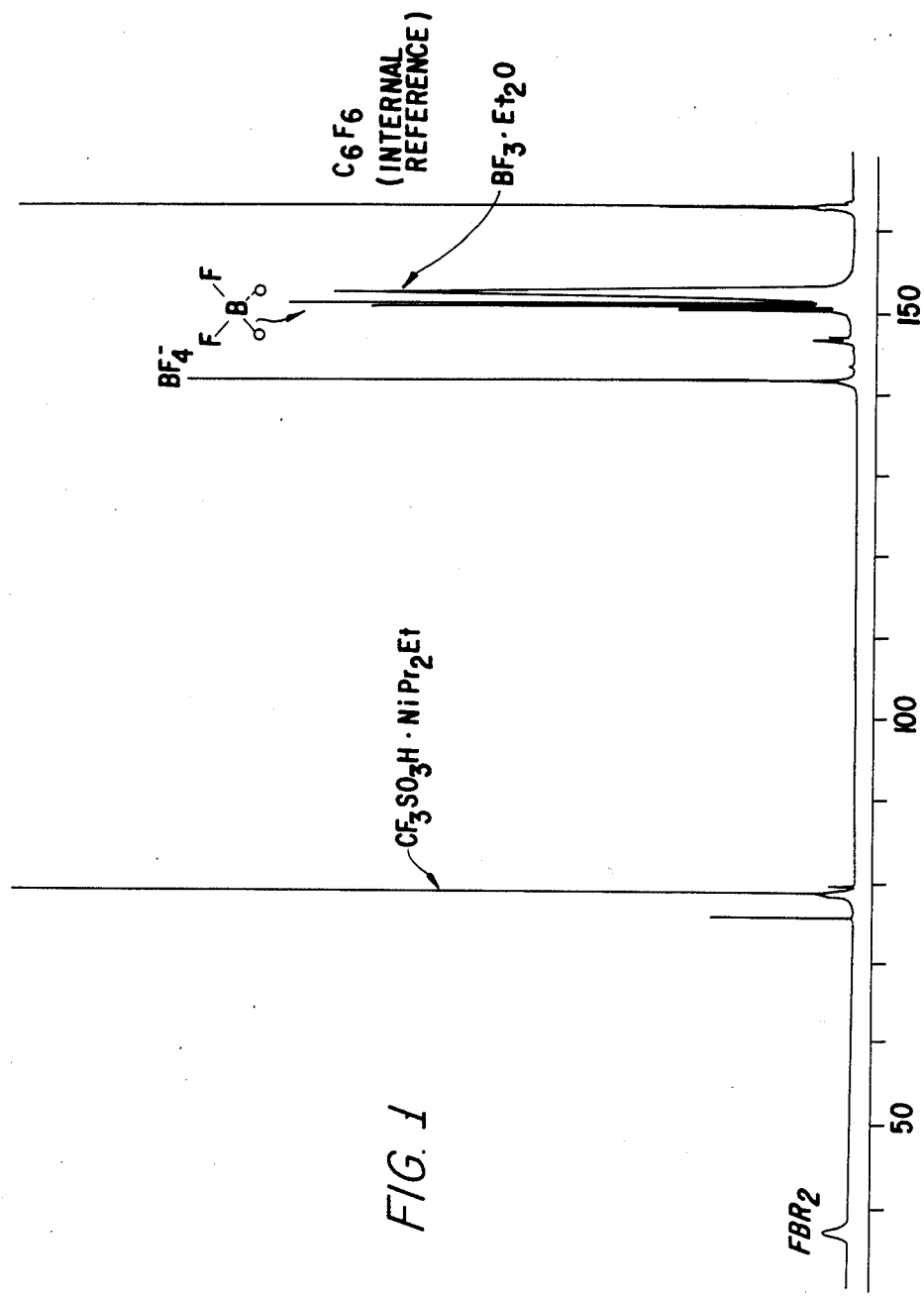
FIG. 1 is a $^{19}F$ NMR spectrogram of the $BF_2$ enolate of N-propionyloxazolidinone taken at 250 MHz using $C_6F_6$ as an internal standard.

Also provided is a compound of the formula:

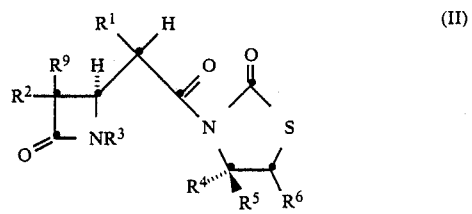

wherein $R^1$ is $C_1$-$C_4$ lower alkyl or alkoxyl, $R^2$ and $R^9$ are independently selected from hydrogen, $C_1$-$C_4$ linear, branched or cyclic alkyl, unsubstituted or substituted with fluoro, hydroxy, or protected hydroxy, with the proviso that both $R^2$ and $R^9$ are not unsubstituted alkyl, $R^3$ is H or easily removable protecting group, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical.

Furthermore there is provided a compound of the formula:

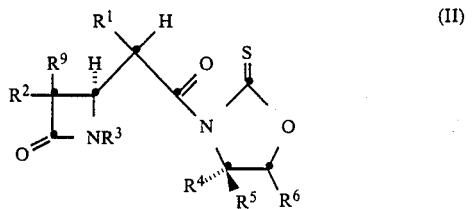

wherein $R^1$ is $C_1$-$C_4$ lower alkyl or alkoxyl, $R^2$ and $R^9$ are independently selected from hydrogen, $C_1$-$C_4$ linear, branched or cyclic alkyl, unsubstituted or substituted with fluoro, hydroxy, or protected hydroxy, with the proviso that both $R^2$ and $R^9$ are not unsubstituted alkyl, $R^3$ is H or easily removable protecting group, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical.

Further there is provided process for preparing the compounds described above of Structure II comprising the step of reacting the azetidinone compound:

where $R^2$ and $R^9$ are independently selected from hydrogen, $C_1$-$C_4$ linear, branched or cyclic alkyl, unsubstituted or substituted with fluoro, hydroxy or protected hydroxy, with the proviso that both $R^2$ and $R^9$ are not unsubstituted alkyl, $R^3$ is H or easily removable protecting group and L is an organo leaving group, with the enolate:

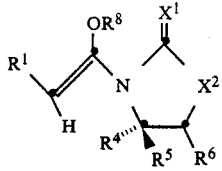
IVA wherein $X^1$ and $X^2$ are independently O or S, $R^1$ is $C_1$-$C_4$ alkyl or alkoxyl, $R^8$ is an easily removable enol protecting group and $R^4$, $R^5$ and $R^6$ are selected from H, $C_1$-$C_4$ alkyl, $C_6$-$C_{10}$ aryl, $C_7$-$C_{10}$ aralkyl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical, in a solvent therefor and in the presence of an organic base and a Lewis acid catalyst to afford Compound IIA.

Specifically provided is where the enolate is of the formula:

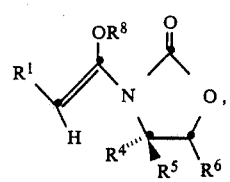

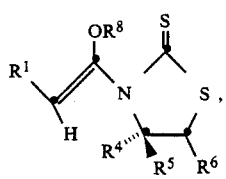

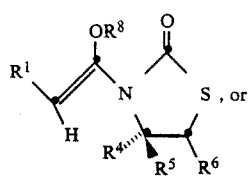

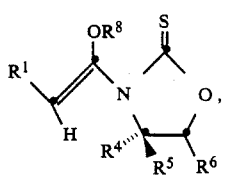

wherein $R^1$ is $C_1$-$C_4$ alkyl or alkoxyl, $R^8$ is an easily removable enol protecting group and $R^4$, $R^5$ and $R^6$ are selected from H, $C_1$-$C_4$ alkyl, $C_6$-$C_{10}$ aryl, $C_7$-$C_{10}$ aralkyl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical, in a solvent therefor and in the presence of an organic base and Lewis acid catalyst to afford Compound II.

Furthermore there is provided a process for preparing a compound of the formula:

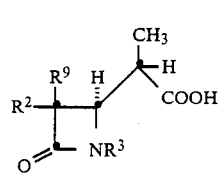
V wherein $R^2$ and $R^9$ are independently selected from hydrogen, $C_1$-$C_4$ linear, branched or cyclic alkyl, unsubstituted or substituted with fluoro, hydroxy, or protected hydroxy, with the proviso that both $R^2$ and $R^9$ are not unsubstituted alkyl, and $R^3$ is H or easily removable protecting group, comprising the steps of (a) reacting the compound:

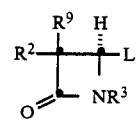
III where $R^2$, $R^9$ and $R^3$ are as described above and L is an organic leaving group, with the chiral compound:

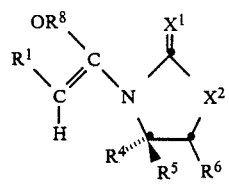
IVA wherein $X^1$ and $X^2$ are independently O or S, $R^1$ is $C_1$-$C_4$ alkyl or alkoxyl, $R^8$ is an easily removable enol protecting group, $R^4$, $R^5$ and $R^6$ independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical, in the presence of an organic base and a Lewis acid catalyst to afford the compound:

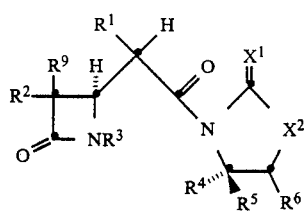
IIA wherein $X^1$, $X^2$, $R^1$, $R^2$, $R^3$, $R^4$, $R^5$, $R^6$ and $R^9$ are as defined hereinabove, and then (b) treating said compound in a solvent therefor, under basic hydrolysis conditions to yield compound V.

Specifically provided is the above process wherein the chiral compound is of the formula:

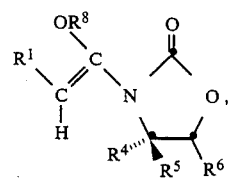

-continued

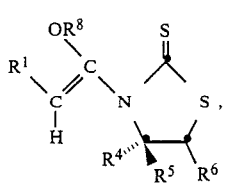

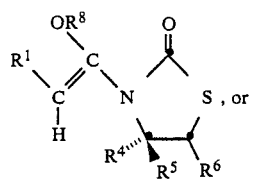

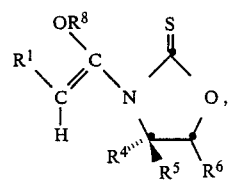

wherein $R^1$ is $C_1$-$C_4$ alkyl or alkoxyl, $R^8$ is an easily removable enol protecting group, $R^4$, $R^5$ and $R^6$ independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, —$SR^{10}$, where $R^{10}$ is $C_1$-$C_4$ alkyl, with the proviso that $R^4$ and $R^5$ are not identical, in the presence of an organic base and a Lewis acid catalyst to afford, respectively, the compound of formula:

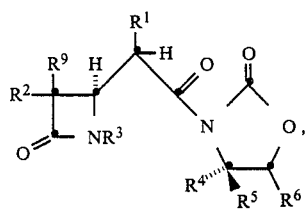

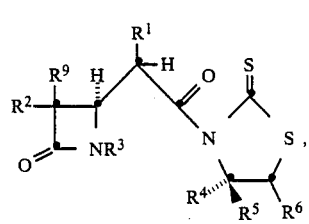

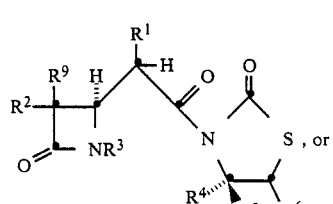

-continued

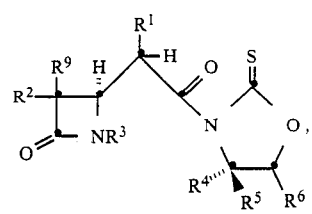

wherein $R^1$, $R^2$, $R^3$, $R^4$, $R^5$, $R^6$ and $R^9$ are as defined hereinabove and then (b) treating said compound in a solvent therefor, under basic hydrolysis conditions to yield compound V.

DESCRIPTION OF THE PROCESS INVENTION AND PREFERRED EMBODIMENTS

The overall subject invention can be easily understood from the following illustrated reaction scheme:

Reaction Scheme

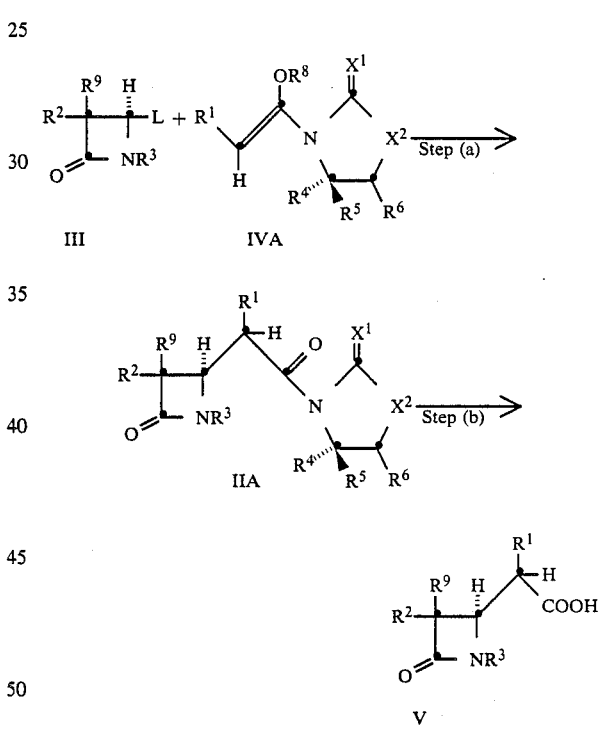

wherein the substituents $R^1$, $R^2$, $R^3$, $R^4$, $R^5$, $R^6$, $R^8$, $R^9$, L, $X^1$ and $X^2$ are described hereinabove.

The chiral auxiliary portion of the enol ether:

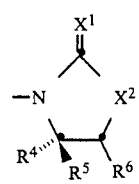

can be any of the following four membered heterocyclic ring systems:

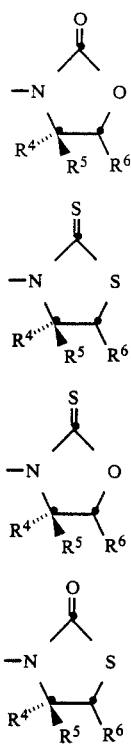

Although all of the ring systems are applicable and included in the subject process, ring system A is preferred due to its higher stability in the basic hydrolysis step and its ability to retain its chiral identity throughout a subsequent recycle step.

Preferably, the subject process is carried out with ring system A as the chiral enol ether according to the scheme:

Reaction Scheme

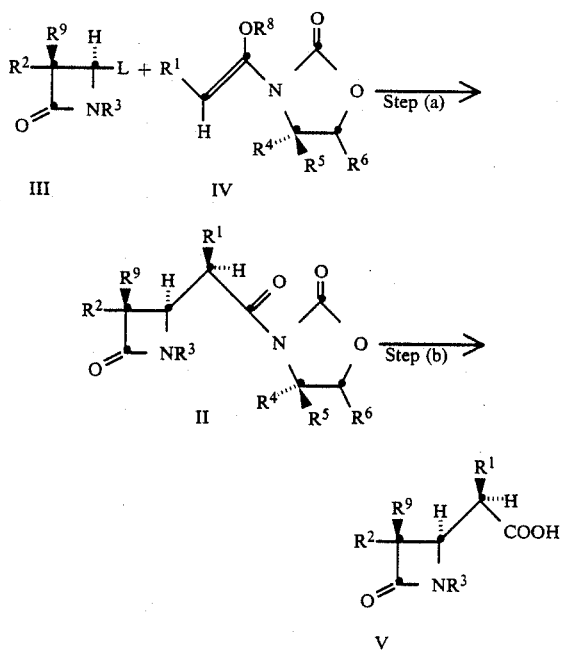

As is seen in the above preferred oxazolidinone reaction scheme, azetidinone III is reacted with the preformed chiral enol ether IV in Step (a) to produce the azetidinone amide II. The resulting structure II is hydrolyzed in Step (b) by suitable means, including use of lithium hydroxide reagent, under basic hydrolysis conditions to produce final compound V which is azetidinone alkyl carboxylic acid. Structure V, wherein $R^1$ is preferably a beta-methyl group, is an intermediate useful in production of 1-beta methyl carbapenem antibiotic reagents as described hereinbefore. Specific and general reaction conditions and parameters are discussed in detail below.

The novelty of the subject process illustrated above resides in the fact that it has been found that reaction of the particular azetidinone and the chiral enol ether leads to resulting intermediate structure II, in which hydrogen at the C-4 azetidinone position is selectively in the alpha configuration and the $R^1$ substituent immediately adjacent to that on the alkyl chain can selectively be chosen to be in the alpha or beta position depending upon substituents $R^4$ and $R^5$ on the chiral oxazolidinone ring and the specific enolating agent used. A bulky alkyl, aralkyl or aryl substituent which is sterically larger by comparison, in the $R^4$ position, with $R^5$ being hydrogen or sterically smaller alkyl, aralkyl or aryl, results in $R^1$ being in the beta configuration which is the most highly desired and preferred configuration. The reverse situation prevails when $R^4=H$, and $R^5$ is the bulky substituent wherein the resulting azetidinone 1-alkyl product is in the alpha configuration.

Any $R^4$ group which is chemically inert under the reaction conditions, and is sterically larger in size or volume than $R^5$, also being chemically inert, will direct the condensation course toward the beta isomer under the reaction conditions described herein.

The same description also applies to $R^6$, when other than H, generally chosen in tandem with $R^5$, on the same face of the 5 membered heterocyclic ring, is chemically inert under the reaction conditions, and tends to act in concert with $R^5$ to aid in the stereoselectivity.

The resulting stereochemistry and facial selectivity described above is generally applicable when using boron or silicon-based enolating agents in the process, e.g. dialkylboron triflate or trialkylsilyl triflate. That is, when $R^5$ is H and $R^4$ a sterically larger substituent on the oxazolidinone ring system, the resulting condensation product contains $R^1$ in the beta configuration, and vice versa. Use of the other enolating agents as described herein will selectively yield either the alpha or beta isomers upon condensation with the azetidinone to yield products within the scope of the subject composition described herein, but may exhibit slightly different courses of stereoselectivity. If the enolating agent selected, together with a specific chiral enol ether (e.g. $R^4$=isopropyl, $R^5$=H) yields the alpha isomer, under the conditions described herein, then it will be obvious to one skilled in the art to repeat the reaction under the same conditions, without undue experimentation, utilizing instead the mirror image form of the chiral enol ether (eg. $R^4$=H, $R^5$=isopropyl) to obtain the desired beta isomer.

Thus, the results from one reaction will yield the total information required to selectively derive either the alpha or beta isomer from any one given set of reaction conditions and reactant materials.

A further novelty of the overall process of the instant invention is a modified and simplified hydrolysis step of structure II to structure V utilizing basic hydrolysis conditions, preferably lithium hydroxide reagent alone in solvent, to achieve hydrolysis of the amide II to the resulting carboxylic acid V in which chirality is preserved and in which the chiral oxazolidinone can be recycled for use in Step (a).

Step (a) is generally carried out by first forming the enolate compound IV by reacting the corresponding chiral compound, e.g. N-acyl oxazolidinone (VII), with an appropriate enolating agent $R^8X$ (VIII) and base:

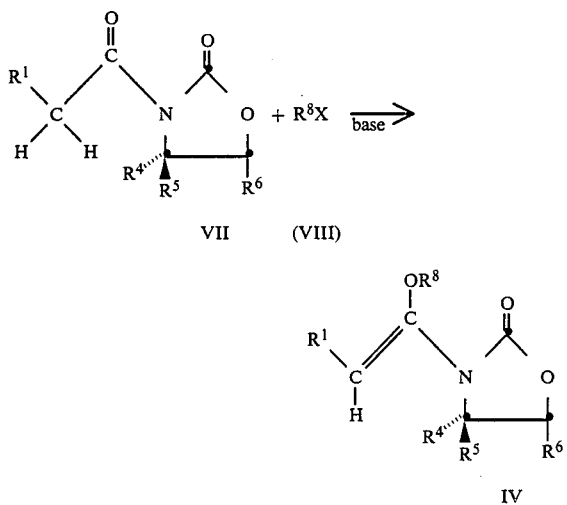

where $R^8X$ can be trimethylsilyl triflate, boron trifluoride etherate, di-n-butylboron triflate, and the like, as described herein, and the base can be an organic nitrogen base to neutralize produced organic acid from the reaction, including trialkylnitrogen or heterocyclic nitrogen compounds, e.g. trimethylamine, triethylamine, pyridine, diisopropylethylamine and the like. Preferred is diisopropylethylamine.

Generally, a 1.1 to 1.0 molar ratio or greater of enolating agent $R^8X$ to N-acyl oxazolidinone (VII) is used, coupled with a 1.2 to 1.0 molar ratio, or greater, of organic nitrogen base to N-acyl oxazolidinone, to effect substantially complete enolate formation.

When utilizing a dialkylboryl enolating agent, e.g. di-n-butylboryl triflate, it is found advantageous to utilize at least a 1.1/1.0 molar ratio of the boryl agent to the N-acyl oxazolidinone together with about at least a 1.2/1.0 molar ratio of organic nitrogen base to the oxazolidinone and allow enolate formation to proceed to completion. After formation of the "Z" enolate is complete, the Lewis acid is added, in about a 1:1 to 3:1 equivalent ratio to the enolate, followed by the azetidinone which is, in a 1:1 molar ratio based on the oxazolidinone together with another 1.1 equivalents of boron enolating agent and 1.2 eqivalents of base. The excess boryl enolating agents is found to maximize the yield of condensation product and is thought to be operating as a protecting-blocking agent involving the ring azetidinone amide nitrogen atom, where the beta lactam ring nitrogen is unsubstituted. Where the N atom is blocked, the excess enolating agent is generally not required.

The enolate can also be formed in situ by the addition of Structure VII, enolating agent, base, azetidinone, and Lewis acid in a one step-one pot sequence.

Generally, this step is performed at −78° C., or at room temperature, in the same solvent used for the condensation step, e.g. methylene chloride and is also generally conducted under dry, inert atmosphere, preferably at atmospheric pressure, usually dry nitrogen gas. Generally, the solution is stirred at −78° C. for a brief period, e.g. 15-30 minutes, allowed to warm to about 0° for 1-2 hours, prior to reaction of the formed enolate with azetidinone Compound III.

After the enolate has been formed, and additional enolating agent added if desired, the azetidinone is added subsequently to the Lewis acid catalyst and the mixture stirred under nitrogen at 0°-25° C., preferably 20°-25° C. for 1-2 hours at room temperature. In cases where the Lewis acid is only partially soluble, methylene chloride can be added to improve the solution.

The Lewis acid catalyst used in Step (a) include zinc halides, including zinc iodide, zinc chloride, and zinc bromide; boron trifluoride etherate; magnesium halide, i.e. chloride; $RAlCl_2$ where R is $C_{1-4}$ alkyl, $TiX_3$ or $TiX_4$, where X is halo, preferably Cl; $SnCl_4$; $SnCl_2$; stannous triflate; $FeCl_3$; trialkylsilyl sulfonates, eg. trimethylsilyl triflate; dialkylboron sulfonates, eg. diethylboron triflate; and the like.

Preferred Lewis acid catalyst in the reaction is zinc bromide and boron trifluoride etherate.

A preferred mode of operation for preforming the enolate in Step (a) is to preferably conduct the reaction at either −78° C., or at room temperature. By so doing, the "Z" isomer, rather than the "E" isomer of the enolate is preferentially formed. The terms "Z" and "E" isomer are well-known in the art and refer to the configurations of the substituents about the double bond where the cis-trans system of nomenclature is inadequate. See for example, "Organic Chemistry" by Alan S. Wingrove and Robert L. Cant, Harper B. Row Publishers, New York, 1981, p. 250. In general, the higher the yield of the desired "Z" enolate isomer during enolate formation, the higher the yield of the condensation product in Step (a). Conducting the reaction at temperatures intermediate between −78° to 25° C. results in mixtures of Z and E isomers, which still allows the novel invention process to be carried out, but however resulting slightly reduced beta/alpha isomeric ratios.

Also in a preferred mode of operation, it is found beneficial to operate at molar ratios of about 2.2:1, of the enolating agent to the N-acyloxazolidinone, where the enolating agent is preferably a dialkylboron triflate, particuarly preferred being diethylboron triflate, and where preferably the N-propionyloxazolidone VII contains $R^4$ as isopropyl and $R^5$ as H. Utilizing this amount of boron enolating agent is found to result in increased yields, presumably due to additional complexing behavior between the enolating agent and the azetidinone.

Further, use of a proportionately larger amount of organic nitrogen base, preferably diisopropylethylamine, results in an increased amount of condensation product.

It should be noted that the dialkylboron triflate enolating agent can be prepared independently or can be generated in situ, for example, the reaction of 1 mole of triethylboron and 1 mole triflic acid, e.g. trifluoromethanesulfonic acid; i.e.,

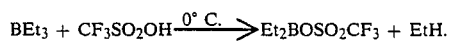

Generally, the reaction can be carried out at 0° C. resulting in about a quantitative yield of enolating agent.

Following formation of the enolate, the condensation step of Step (a) is carried out.

Reaction conditions for Step (a) include the use of a dry aprotic solvent. Representative examples of suitable solvents include aliphatic hydrocarbons including pentanes, hexanes, heptanes, aromatic hydrocarbons including benzene, toluene and halogenated hydrocarbons including chlorobenzene, carbon tetrachloride, methylene chloride and the like. A preferred solvent is methylene chloride.

Typical concentrations of the azetidinone III and the initially formed chiral enol ether IV used in Step (a) are usually in the range of 0.1 to 1.0 Molar and preferably 0.1 to 0.2 Molar.

The temperature used during the condensation of III and IV in Step (a) is normally carried out in a temperature range of 0° to 25° C. and preferably in the region of 20° to 25° C.

Step (a) of the process is generally carried out at atmospheric pressure in a dry atmosphere preferably in a nitrogen or argon atmosphere.

Time of the reaction is normally in the range of 0.5 to 10 hours being sufficient to achieve yields in the range of 80 to 95%.

A preferred mode of carried out Step (a) in addendum to the preferred mode of preforming the enolate, described above, is to conduct the condensation at room temperature with a substantially pure solution of "Z" isomer, utilizing an azetidinone III having $R^9=H$ and $R^2=$ protected hydroxy $OR^8$, where $R^8=$ trialkylsilyl blocking group, preferably dimethyl-t-butylsilyl, in a molar ratio of about 1:1 based on the amount of starting chiral N-acyloxazolidinone. Particularly preferred is where the chiral oxazolidinone moiety has $R^4=$ isopropyl and $R^5=H$.

Further, following the condensation step, an oxidizing agent, such as 30% $H_2O_2$, may be added to convert excess boron organics to boric acid as an aid in reducing the number of side products preceding the subsequent basic hydrolysis step.

The separation, isolation, and purification of resulting structure II in the reaction is generally carried out by techniques known in the art particularly involving crystallization and chromatography.

The starting azetidinone of Structure III is known in the art and can be prepared by several procedures including that described in the hereby incorporated by reference of Paul J. Reider and Edward J. Grabowski in *Tetrahedron Letters*, Vol. 23, pp. 2293–2296 (1982) starting with L-aspartic acid resulting in structure III, where $R^2$ is 1-hydroxyethyl, and $R^9$ is H, by a lead acetate oxidation of the corresponding 4-carboxy azetidinone in DMF-HOAc media. This is particularly a preferred method for synthesis of structure III in which different alkylation reagents can be used to derive, via known methods, all of the $R^2$ and $R^9$ substituents included within the scope of the disclosed composition II.

Another reference disclosing the starting azetidinone 4-acetate is *Tetrahedron*, Vol. 40, No. 10, pp. 1795–1802 (1984) hereby incorporated by reference for this purpose.

A further method is described in the reference *Tetrahedron*, Vol. 39, No. 15, pp. 2505–2513 (1983) hereby incorporated by reference also for this particular purpose.

The following synthetic scheme taken from the above-cited *Tetrahedron*, Vol. 39 reference, is presented below for illustration purposes, and is also a convenient methodology for readily obtaining all of the structures encompassed by the scope of Structure III, incorporating different hydroxy and alkyl species for $R^2$, starting with 6-aminopenicillanic acid:

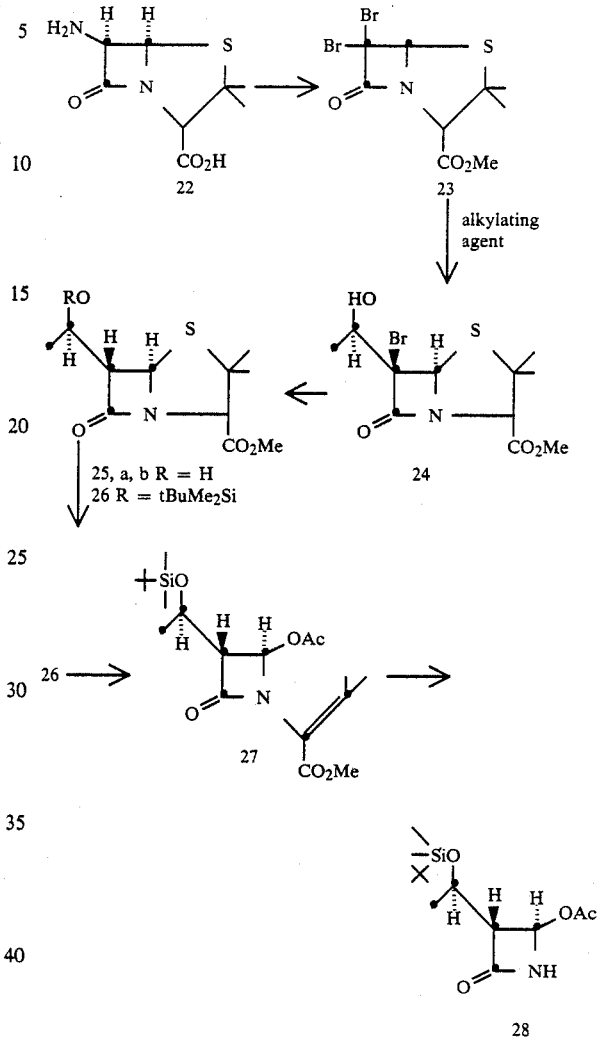

As is seen, methyl 6,6-dibromopenicillanate (23) is readily obtained from 22 (6-aminopenicillanic acid) by diazotization-bromination at 5° C. using $Br_2$, $NaNO_2$, $H_2SO_4$, $H_2O-CH_2Cl_2$, followed by esterification of the crude dibromo acid. 23 underwent metal-halogen exchange with methylmagnesium bromide in THF at −78° C. to give an enolate intermediate, which on quenching with excess acetaldehyde, affords a mixture of hydroxyethyl products in high yield. At this point, use of acetaldehyde leads to the 1-hydroxyethyl analog, whereas use of the following alkylating agents, including aldehydes and ketones, leads to the corresponding alkyl, fluoroalkyl and hydroxyalkyl products:

| Alkylating Agent | $R^2$ or $R^9$ Product |
| --- | --- |
| $CH_2O$ | $HOCH_2-$ |
| $(CH_3)_2CO$ | $(CH_3)_2CH(OH)-$ |
| $CH_3COCH_2CH_3$ | $CH_3C(OH)-CH_2CH_3$ |
| $CH_3CH_2CHO$ | $CH_3CH_2C(OH)-H$ |
| $CH_3CH_2CH_2CHO$ | $CH_3CH_2CH_2CH(OH)-$ |
| $(CH_3)_2CHCHO$ | $(CH_3)_2CH-CH(OH)-$ |
| $CH_3I$ | $CH_3-$ |
| $CH_3CH_2Br$ | $CH_3CH_2-$ |
| $(CH_3)_2CHBr$ | $(CH_3)_2CH-$ |
| $CF_3CHO$ | $CF_3CHOH-$ |

| Alkylating Agent | $R^2$ or $R^9$ Product |
|---|---|
| $CHF_2CHO$ | $CHF_2CHOH-$ |
| $CH_2FCHO$ | $FCH_2CHOH-$ |
| $F_2CHI$ | $F_2CH-$ |
| $F_3CI$ | $F_3C-$ |
| $CH_3CF_2I$ | $CH_3CF_2-$ |
| $(CH_2)_2C=O$ | $(CH_2)_2COH-$ |

These reagents, useful in alkylating the azetidinone ring are described in U.S. Pat. No. 4,383,946, hereby incorporated by reference for this particular purpose.

The major bromohydrin 24 having the desired R configuration at the OH-bearing carbon can be isolated by a combination of chromatography and crystallization. Stirring 24 with 3 molar equivalents of zinc in a mixture of diethyl ether and aqueous ammonium acetate at room temperature affords a 91:9 mixture of trans and cis isomers 25a, b. The mixture of alcohols is converted to the corresponding mixtures of t-butyldimethylsilyl derivatives 26a and 26b by reaction with t-butyldimethylchlorosilane in DMF with imidazole base at room temperature and the thiazolidine ring is then disrupted by the use of $Hg(OAc)_2$ in HOAc at 90° C. to yield 27, being the major isomer. Oxidation of the mixture with a catalytic amount of potassium permanganate and sodium periodate in buffered acetone removes the N-isopropylidine-acetate group to produce a mixture of azetidinones in which the major isomer is isolated to result in 28.

Further defining the structure of III, $R_2$ and $R^9$ are independently hydrogen, $C_{1-4}$ linear, branched or cyclic alkyl, unsubstituted or substituted with fluoro, hydroxy, or protected hydroxy with the proviso that both $R^2$ and $R^9$ are not unsubstituted alkyl, which situation generally leads to compounds of marginal antibiotic activity.

Representative examples of $R^2$ groups include H, $HO-CH_2-$, $CH_3CHOH-$, $(CH_3)_2COH-$, $(CH_2)_2COH-$, $CH_3CH_2CH(OH)-$, $CH_3CH_2CH_2CH(OH)-$, $$CH_3CH_2CH(OH)-, \quad CH_3-CH-CH(OH)-, \\ \phantom{CH_3CH_2CH(OH)-,\;}CH_3 \phantom{CH_3-CH-}CH_3$$

$CH_3-$, $CH_3CH_2-$, $(CH_3)_2CH-$, $CH_3CH_2CH_2CH_2-$, $CF_3CHOH-$, $CHF_2CHOH-$, $FCH_2CHOH-$, $CH_3CHF-$, $F_2CH-$, $F_3C-$, $CH_3CF_2-$ and the like. Preferred $R^2$ group is $CH_3CHOH-$, i.e., 1-hydroxyethyl, and a preferred $R^9$ group is H, preferably a beta H in position 3 of the azetidinone ring.

The protected hydroxy is known in the antibiotic art and refers to a hydroxyl group protected by a suitable radical rendering it inactive during chemical reaction. The chemical reaction in the instant case of the azetidinone with the chelated enolate followed by hydrolysis of the resulting 2-oxo-1,3-oxazolidinone moiety to the corresponding carboxylic acid in the presence of LiOH under hydrolysis conditions. Suitable protecting groups which are known include p- or o-nitrobenzoxycarbonyl produced for example by treating the hydroxy compound with 1.5 eq. of p-nitrobenzoxycarbonyl chloride and 2.0 eq. of p-dimethylaminopyridine in a solvent such as DMF at room temperature for 30 minutes to 6 hours to yield the protected hydroxy product.

Alternatively, the protecting group can be organosilyl group, e.g. trimethylsilyl, phenyldimethylsilyl, isopropyldimethylsilyl or t-butyldimethylsilyl, formed by treating the hydroxy compound in DMF with for example, t-butyldimethylchlorosilane and imidazole as the base at room temperature for about 2 hours.

The protecting groups described above can then be easily removed by acid hydrolysis, for example HCl in aqueous methanol at room temperature for about one hour.

A preferred protecting group is t-butyldimethylsilyl.

Leaving group L, in structure III is generally a nucleophile which can easily be displaced by the nucleophilic chiral enol ether IV.

Representative examples of suitable leaving groups L include acetate, benzoate, trifluoroacetate, tosylate, mesylate, brosylate, halide, including Cl, Br, I; $C_1-C_4$ ether, $C_1-C_4$ alkylthioether, $C_1-C_4$ alkyl sulfone, $C_1-C_4$ alkyl sulfoxide, and the like. Preferred leaving group L in the subject process is acetate.

$R^3$ can be H or an N-protecting group selected generally from protecting groups known in the art which employ hydrogenation, oxidation or acid hydrolysis for removal.

Representative protecting groups $R^3$ include the silyl groups described above and further including benzyl, p-nitrobenzyl, p-nitrobenzoylmethyl, benzhydryl, p-methoxybenzyl, 2,4-dimethoxybenzyl, and the like. A preferred protecting group if utilized is silyl, described above.

Preferably $R^3$ is H in the process to avoid unnecessary process steps.

Representative examples of structure III useful in the overall process are given in the following Table I:

TABLE I

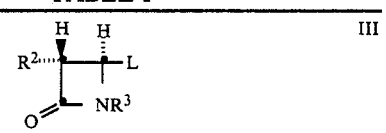

| Compound | $R_2$ | $R_3$ | L |
|---|---|---|---|
| 1 | $HOCH_2-$ | H | $OCOCH_3$ |
| 2 | $CH_3CHOH-$ | H | $OCOCH_3$ |
| 3 | $(CH_3)_2COH-$ | H | $OCOCH_3$ |
| 4 | $CH_3CH(O-DMTBS)-$ | H | $OCOCH_3$ |
| 5 | $CH_3CH(O-TMS)-$ | H | $OCOCH_3$ |
| 6 | $CH_3CH(O-Bz)-$ | H | $OCOCH_3$ |
| 7 | $CH_3CH(O-PNB)-$ | H | $OCOCH_3$ |
| 8 | $CH_3CH(O-PNBC)-$ | H | $OCOCH_3$ |
| 9 | $CH_3CH_2\underset{\underset{H}{\vert}}{C}(OH)-$ | H | $OCOCH_3$ |
| 10 | $CH_3CH_2CH_2CH(OH)-$ | H | $OCOCH_3$ |
| 11 | $CH_3CH-\underset{\underset{CH_3}{\vert}}{CH}(OH)-$ | H | $OCOCH_3$ |
| 12 | $CH_3CH_2-\underset{\underset{CH_3}{\vert}}{C}(OH)-$ | H | $OCOCH_3$ |
| 13 | $HOCH_2$ | H | $OCOPh$ |
| 14 | $CH_3CHOH$ | H | $OCOPh$ |
| 15 | $(CH_3)_2COH$ | H | $OCOPh$ |
| 16 | $CH_3CH_2CH(OH)-$ | H | $OCOPh$ |
| 17 | $CH_3CH_2CH_2CH(OH)-$ | H | $OCOPh$ |
| 18 | $CH_3-\underset{\underset{CH_3}{\vert}}{CH}-CH(OH)-$ | H | $OCOPh$ |

TABLE I-continued

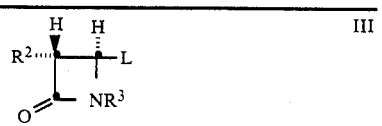

| Compound | R2 | R3 | L |
|---|---|---|---|
| 19 | CH₃CH₂—C(OH)(CH₃)— | H | OCOPh |
| 20 | CH₃CH(O—DMTBS) | H | OCOPh |
| 21 | CH₃CH(O—TMS) | H | OCOPh |
| 22 | CH₃CH(O—Bz) | H | OCOPh |
| 23 | CH₃CH(O—PNB) | H | OCOPh |
| 24 | CH₃CH(O—PNBC) | H | OCOPh |
| 25 | CH₃CH(O—DPTBS) | H | OCOPh |
| 26 | CH₃CH(O—TPS) | H | OCOPh |
| 27 | CH₃CH(O—TPDMS) | H | OCOPh |
| 28 | H | DMTBS | OSO₂PhMe |
| 29 | CH₃CHOH | DMTBS | OSO₂PhMe |
| 30 | (CH₃)₂COH | DMTBS | OSO₂PhMe |
| 31 | CH₃CH₂CH(OH)— | TMS | OSO₂PhMe |
| 32 | CH₃CH₂CH₂CH(OH) | TMS | OSO₂PhMe |
| 33 | CH₃—CH(CH₃)—CH(OH)— | TMS | OSO₂PhMe |
| 34 | CH₃CH₂—C(OH)(CH₃)— | DPTBS | OSO₂PhMe |
| 35 | CH₃CH(O—DMTBS) | DPTBS | OSO₂PhMe |
| 36 | (CH₃)₂C(O—PNB) | DPTBS | OSO₂PhMe |
| 37 | CH₃CH₂CH(O—DPTBS) | TPS | OSO₂PhMe |
| 38 | CH₃CH₂C(CH₃)—(O—IPDMS) | TPS | OSO₂PhMe |
| 39 | (PNBC—O)CH₂ | TPS | OSO₂PhMe |
| 40 | HOCH₂ | PNBC | OSO₂Me |
| 41 | CH₃CHOH— | PNBC | OSO₂Me |
| 42 | (CH₃)₂COH | PNBC | OSO₂Me |
| 43 | CH₃CH₂CH(OH)— | PNBC | OSO₂PhBr |
| 44 | CH₃CH₂CH₂CH(OH)— | PNBC | OSO₂PhBr |
| 45 | CH₃CH(CH₃)—CH(OH)— | PNBC | OSO₂PhBr |
| 46 | CH₃CH₂—C(OH)(CH₃)— | H | OSO₂PhBr |
| 47 | CH₃CH(O—DMTBS) | H | Br |
| 48 | (TMS—O)CH₂ | H | Br |
| 49 | (CH₃)₂C(O—Bz) | H | Cl |
| 50 | CH₃CH₂CH(O—PNB) | H | Cl |
| 51 | CH₃CH₂CH(O—PNBC) | PNBC | OSO₂PhNO₂ |
| 52 | CH₃CH₂CH₂CH(O—DPTBS) | PNBC | OSO₂PhNO₂ |
| 53 | CH₃—CH(CH₃)—CH(O—TPS) | PNBC | OSO₂PhNO₂ |
| 54 | CH₃—CH₂—C(CH₃)(O—IPDMS) | PNBC | OSO₂PhNO₂ |

Abbreviations used in the table:
DMTBS = dimethyl-t-butylsilyl
TMS = trimethylsilyl
Bz = benzyl
PNB = p-nitrobenzyl
PNBC = p-nitrobenzylcarbonyl
DPTBS = diphenyl-t-butylsilyl
IPDMS = isopropyldimethylsilyl
Ph = phenyl
Me = methyl
PhBr = p-bromophenyl
PhNO₂ = p-nitrophenyl
PhMe = p-tolyl The structures and formulas representative of Structure III given in the above Table are not meant to be limiting and other combinations of R², R³ and L and their resulting species of Structure III, which will be obvious to one skilled in the art from this disclosure, are also deemed to be included within the scope of this invention.

A preferred azetidinone structure III useful in the process is

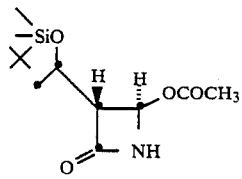

The starting chiral enol ether of structure IV ring system A, can be conveniently prepared for example by the process described in the above-cited reference of Evans et al., JACS 1981, 103, pp. 2127–2129 and JACS 1982, 104, pp. 1737, hereby incorporated by reference for this particular purpose.

Synthesis of structure IV where $X^1$ and X are O, $R^4$ is isopropyl and $R^5$ is H can be accomplished by reacting an aminoalcohol, eq. L-valinol, with a bridging-cyclization reagent such as liquid diethylcarbonate at 110° C., for 5–15 hours, until ethanol distillation ceases, to effect bridging-cyclization. In this case, the reaction yields 4-(S)isopropyl-2-oxo-1,3-oxazolidinone.

Other amino alcohols which can also be utilized are L-phenylalanine leading to 4(S)-4-benzyl-2-oxo-1,3-oxazolidinone, L-norephedrine, L-alanine, L-valine, L-leucine, L-isoleucine, L-phenylalanine, L-tyrosine, L-serine, L-threonine, L-cysteine, L-methionine, and the like. Use of the naturally occurring L-amino acids, followed by reduction, such as by BH₃.SMe₂, BH₃.THF, LiAlH4 or NaBH4.EtOH (via ethylester.HCl salt) in THF, Et₂O solvents, 35°–70° C., for a period of 10–15 hours leads to the L-amino alcohol precursor to the structure IVA in which $R^4$ is alkyl or aryl and $R^5$ is H, thus favoring beta methyl configuration after condensation when using boron or silyl enolating agents. Utilizing the analogous D-amino acids will result in the opposite form of Structure IVA which will subsequently favor alpha-methyl formation during their condensation. These reduction methods are described in *Tetrahedron Letters,* No. 40, pp. 3527–3528 (1977), hereby incorporated by reference for this purpose. The reduction methods can be carried out with very little accompanying racemization.

A preferred amino alcohol in the process L-valinol.

Other bridging-cyclization agents include diphenyl carbonate, diethyl carbonate (see Homeyer, A. H., U.S. Pat. No. 2,399,118 and *Chem. Abstr.* (1946) Vol. 40, 4084, both hereby incorporated by reference for this purpose; phosgene (see Close, W. J., *J. Org. Chem.,* 1950, Vol. 15, 1131–34, hereby incorporated by reference for this purpose; and the like. Preferred is diethyl carbonate.

The other ring systems B, C and D of the chiral enol ether are also made by known methods in the art.

The method of *Bull. Soc. Chim. Bel.,* 87, 223, 229, 293 and 299 (1978) can be used to make ring system C, and additionally using L-valinol, it can be prepared for example:

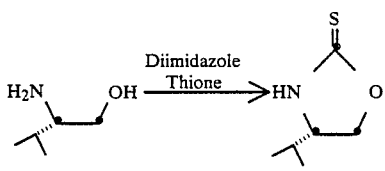

described by the methods in H. A. Staab and G. Walter, *Ann.,* 657, 98, 104 (1962), *Carbohydrate Res.* Vol. 3, p. 205 (1966), and *Angew. Chem.* 97, 292 (1967), hereby incorporated by reference for this particular purpose.

Likewise, ring system B can be made for example by the method of Fujita et al. in *J. Am. Chem. Soc.* 1982, Vol. 104, pp. 2079–81,

hereby incorporated by reference for this particular purpose.

Likewise, ring system D can be made for example, from the thiol-amine by the method described above using diethyl carbonate:

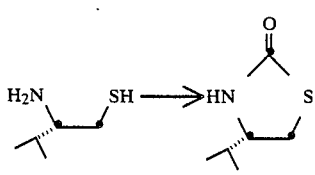

hereby incorporated by reference to this particular purpose.

Methods for preparing the starting thiol-amine are well known if the art, e.g.

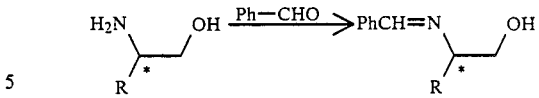

See A. I. Meyers, et al., *J. Org. Chem.* 43, 892 (1978)

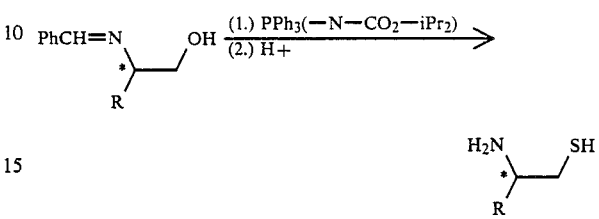

R. P. Volante, *Tet. Lett.* 3119 (1981)

Preferred are ring systems A, being, oxazolidinone; and B, being thiazolidinethione, both preferably containing a 4-isopropyl substituent, resulting in the corresponding condensation products containing a beta-methyl substituent.

Following the cyclization reaction, the formed oxazolidinone is N-acylated to form the nucleophilic precursor of the molecule. The oxazolidinone is reacted with butyllithium in hexane, to form the conjugate base and then reacted with an acyl halide such as propionyl chloride at −71° C., for 0.5–1 hour to yield the N-propionyloxazolidinone.

Other acylating agents include n-butanoyl chloride, n-pivaloyl bromide, acetyl choride, and the like. Preferred is n-propionyl chloride.

The initial step in Step (a) of the process is to convert the N-acyl oxazolidinone structure to the chiral enol ether by reaction with suitable enolating or chelating agent. For example, the N-acyl-4(s)-isopropyloxazolidinone is reacted with the enolating-protecting compound, such as trimethylsilyltriflate, in $CH_2Cl_2$ solvent, at −78° C., in the presence of diisopropylethylamine proton acceptor, for 15–30 minutes, then for 1–2 hours at 0° C. to obtain the O-trimethylsilyl enol ether.

Representative enolating groups $R^8$ are described hereinbelow with their particular structures.

$R^8$ is also an easily removable protecting group for the chiral enol ether which will stabilize the compound in the enol structure. The protecting group can simply be a hydroxy-protecting group such as derived from a triorganosilicon compound, eg. trimethylsilyl (TMS), formed by reacting the oxazolidinone with for example, lithium diisopropylamide and trimethylsilyl chloride in THF, solvent, at −78° C. for ½ to 2 hours to form the TMS derivative.

By the term "easily removable protecting group", as used herein, is meant that the $R^8$ group is removed, presumably through the action of the Lewis acid during the condensation step without affecting the stability of the enol moiety or its positional influence on the resulting stereochemistry.

As is evident from this discussion, the function of the $R^8$ group is twofold: first, it serves as a stabilizing force on the enol moiety, which is the reactive center for alkylation attack on the 4-position of the azetidinone ring: and secondly, it "anchors" the enol into the "Z" enol isomer configuration, rather than the "E", which leads to the desired product stereochemistry in the condensation product. Thus, it simultaneously serves as a protecting group, in addition to being easily removable, and thus facilitating the condensation reaction.

Also the protecting group can have the ability to complex the keto group of the oxazolidinone moiety thus more firmly positioning the molecule for the nucleophilic attack on the azetidinone structure.

Representative examples of this type enolating agent include the above-described dialkylboryl groups, such as di-n-butylboryl, formed for example by reacting the oxazolidinone with di-n-butylboryltriflate in $CH_2Cl_2$ solvent, $-78°$ C., 1 hour time to form the di-n-butylboryl derivative.

Representative examples of $R^8$ groups useful in the subject process include the radicals trialkylsilyl, including trimethylsilyl, dimethyl-t-butylsilyl; dialkylboryl, including di-n-butylboryl, dimethylboryl, diethylboryl; lithium; MgX; ZnX; $AlX_2$; $BR_2$; $BX_2$, particularly $BF_2$; SnX; $ZrXR_2$; where X is halo, i.e., Cl, Br, I, F, preferably F, or triflate and R is $C_1$-$C_4$ alkyl or aryl, preferably methyl or ethyl, and the like, which can be derived for example from their respective salts, e.g. triflates or halides.

Preferred $R^8$ groups in the process are difluoroboryl, di-n-butylboryl, diethylboryl, trimethylsilyl, and stannus monotriflate.

The lithium salt can advantageous be used as an intermediate in forming the other enolating structures. For example, reacting the N-propionyl oxazolidinone with LDA under enol forming conditions, resulting Li salt, can be reacted for example with magnesium chloride to form the corresponding magnesium halide enol-complex, which can be subsequently utilized in the condensation step.

A particularly preferred mode of carrying out the subject process involves the use of $R^8=BF_2$ as the enol protecting group in the structure IVA, particularly where $X^1$, $X^2$ are oxygen.

Use of $BF_2$ as $R^8$ avoids the use of triflate ($CF_3SOO^-$) chemistry which is extremely expensive, air and moisture sensitive, and results in substantially the same yields and beta/alpha ratios and eliminates the need for a separate Lewis acid since the $BF_2$ enolate can be readily formed from other enol protected forms of IVA, including trimethylsilyl, dialkylboryl i.e., diethylboryl and the like, by treatment with $BF_3$ etherate, in excess, which acts as the Lewis acid. Further, the boron difluoride enolate can be formed directly from N-alkanoyloxazolidinone itself by treatment with $BF_3$ etherate.

The $BF_2$ enolate of Structure IVA can be readily identified in situ on the basis of its $^{19}F$ and $^{13}C$ NMR spectra discussed in the Examples 13 and 14 which will be readily appreciated by one skilled in the art for preparing and identifying the $BF_2$ enolate. The $BF_2$ enolate is substantially stable in solution.

Also a subject of this invention is a compound of the formula:

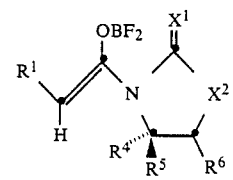

wherein $X^1$ and $X^2$ are independently O or S, $R^1$ is $C_1$-$C_4$ lower alkyl or alkoxyl, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —$OR^{10}$, —SH, $SR^{10}$, where $R^{10}$ is $C_1$-$C_4$ alkyl, with the proviso that $R^4$ and $R^5$ are not identical. Particularly preferred are where $X^1$, $X^2$ are oxygen, $R^1$ is methyl, $R^5$ is H, $R^4$ is isopropyl or phenyl, and $R^6$ is respectively, hydrogen or methyl.

$R^1$ in structure IV is $C_1$-$C_4$ alkyl or alkoxyl and includes methyl, ethyl, propyl, isopropyl, n-butyl, isobutyl, sec-butyl, t-butyl, methoxy, ethoxy, propoxy, isopropoxy, n-butoxy, isobutoxy, sec-butoxy, t-butoxy, which can also contain substituents such as halogens, e.g. F, Cl, and heteroatoms, e.g. —O—, which are inert under the reaction conditions of the subject process. Preferred $R^1$ is methyl.

The remaining groups on the oxazolidinone nucleus $R^4$, $R^5$ and $R^6$ are selected from H, $C_1$-$C_4$ alkyl, $C_7$-$C_{10}$ aralkyl, $C_6$-$C_{10}$ aryl, $C_7$-$C_{10}$ alkaryl, which $R^4$, $R^5$ and $R^6$ groups can be substituted with —OH, $OR^{10}$, —SH, —$SR^{10}$, wherein $R^{10}$ is $C_1$-$C_4$ alkyl, preferably methyl, with the proviso that $R^4$ and $R^5$ are not identical.

The rationale for this proviso is that the position of the substituent has been found to directly affect the stereochemistry of the resulting intermediate. Thus, when utilizing boron or silicon based enolating agents, if $R^1$ is methyl, and $R^4$ is preferably alkyl and $R^5$ is H, the resulting stereochemistry in structure II will predominantly be the beta-methyl configuration. Conversely, if $R^4$ is H and $R^5$ is alkyl, then the resulting stereochemistry of structure II will predominantly be alpha-methyl configuration. If both $R^4$ and $R^5$ are alkyl, then the resulting product will tend to be a mixture of both epimers, unless one alkyl is substantially sterically larger than the other, e.g., if $R^4$ is t-butyl and $R^5$ is methyl, $R^1$ will tend to be of beta configuration.

Representative examples of $R^4$, $R^5$ and $R^6$ groups include H, methyl, ethyl, propyl, isopropyl, n-butyl, isobutyl, sec-butyl, t-butyl, benzyl, 1-phenethyl, 2-phenethyl, 2,4-dimethylphenyl, and the like.

Preferred in the process is where $R^5$ (beta substituent) is H and $R^4$ (alpha substituent) is $C_1$-$C_4$ alkyl, preferably isopropyl, for structures IIA and IVA, where $X^1$ and $X^2$ are either both O or S (ring structures A or B, respectively).

Representative examples of structure IV which are utilized in the present subject process include those in the following Table II:

TABLE II

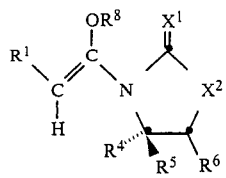

IVA

| Compound | R¹ | R⁴(S) | R⁵(R) | X¹ | X² | R⁶ | R⁸ |
|---|---|---|---|---|---|---|---|
| 1 | CH₃ | CH₃ | H | O | O | H | BF₂ |
| 2 | CH₃ | CH₃CH₂ | H | O | O | H | BF₂ |
| 3 | CH₃ | (CH₃)₂CH | H | O | O | H | BF₂ |
| 4 | CH₃ | CH₃CH₂CH₂ | H | O | O | H | BF₂ |
| 5 | CH₃ | CH₃CH₂CH₂CH₂ | H | O | O | H | BF₂ |
| 6 | CH₃ | (CH₃)₂CH—CH₂ | H | O | O | H | BF₂ |
| 7 | CH₃ | CH₃CH₂CH(CH₃)— | H | O | O | H | DEB |
| 8 | CH₃ | Ph—CH₂ | CH₃ | O | O | H | DEB |
| 9 | CH₃ | p-CH₃—Ph—CH₂ | H | O | O | H | DEB |
| 10 | CH₃ | 2,4-di-CH₃Ph—CH₂ | CH₃ | O | O | H | DEB |
| 11 | CH₃ | 2,4,5-triCH₃PhCH₂ | H | O | O | H | DEB |
| 12 | CH₃ | 2,4,6-triCH₃PhCH₂ | H | O | O | H | DEB |
| 13 | CH₃ | Ph | H | O | O | H | DEB |
| 14 | CH₃ | CH₃ | H | O | O | Ph | TMS |
| 15 | OCH₃ | CH₃ | HO | O | O | H | TMS |
| 16 | OCH₃ | CH₂CH₂ | H | O | O | H | TMS |
| 17 | OCH₃ | (CH₃)₂CH | H | O | O | H | TMS |
| 18 | OCH₃ | CH₃CH₂CH₂ | H | O | O | H | MST |
| 19 | OCH₃ | CH₃CH₂CH₂CH₂ | H | O | O | H | MST |
| 20 | OCH₃ | (CH₃)₂CHCH₂ | H | O | O | H | MST |
| 21 | OCH₃ | CH₃CH₂CH(CH₃)— | H | O | O | H | MST |
| 22 | OCH₃ | PhCH₂ | H | O | O | H | MST |
| 23 | OCH₃ | p-CH₃PhCH₂ | H | O | O | H | MST |
| 24 | OCH₃ | 2,4-diCH₃PhCH₂ | CH₃ | O | O | H | TMS |
| 25 | OCH₃ | 2,4-5-triCH₃PhCH₂ | CH₃ | O | O | H | TMS |
| 26 | OCH₃ | 2,4,6-triCH₃PhCH₂ | CH₃ | O | O | H | TMS |
| 27 | OCH₃ | Ph | H | O | O | H | TMS |
| 28 | OCH₃ | CH₃ | H | O | O | Ph | TMS |
| 28 | OCH₃ | CH₃ | H | O | O | Ph | TMS |
| 29 | CH₃ | CH₃ | H | O | O | H | DBB |
| 30 | CH₃ | CH₃CH₂ | H | O | O | H | DBB |
| 31 | CH₃ | (CH₃)₂CH | H | O | O | H | DBB |
| 32 | CH₃ | CH₃CH₂CH₂ | H | O | O | H | DBB |
| 33 | CH₃ | CH₃CH₂CH₂CH₂ | H | O | O | H | DBB |
| 34 | CH₃ | (CH₃)₂CH—CH₂ | H | O | O | H | DBB |
| 35 | CH₃ | CH₃CH₂CH(CH₃)— | H | O | O | H | DBB |
| 36 | CH₃ | Ph—CH₂ | H | O | O | H | DBB |
| 37 | CH₃ | p-CH₃—Ph—CH₂ | H | O | O | H | DBB |
| 38 | CH₃ | 2,4-diCH₃PhCH₂ | H | O | O | H | DBB |
| 39 | CH₃ | 2,4,5-triCH₂PhCH₂ | H | O | O | H | DBB |
| 40 | CH₃ | 2,4,6-triCH₃PhCH₂ | H | O | O | H | DBB |
| 41 | CH₃ | Ph | H | O | O | CH₃ | DBB |
| 42 | CH₃CH₂ | H | CH₃ | O | O | CH₃ | TMS |
| 43 | CH₃CH₂CH₂ | H | Ph | O | O | CH₃ | TMS |
| 44 | (CH₃)₂CH | H | (CH₃)₂CH | O | O | CH₃ | TMS |
| 45 | CH₃CH₂CH₂CH₂ | H | (CH₃)₂CHCH₂ | O | O | CH₃ | TMS |
| 46 | CH₃CH(CH₃)CH₂ | H | CH₃CH₂CH(CH₃)— | O | O | CH₃ | TMS |
| 47 | CH₃CH₂CH(CH₃)— | H | PhCH₂ | O | O | CH₃ | TMS |
| 48 | CH₃CH₂O | (CH₃)₂CH | H | O | O | CH₃ | DEB |
| 49 | CH₃CH₂CH₂O | (CH₃)₂CH | H | O | O | CH₃ | DEB |
| 50 | (CH₃)₂CHO | (CH₃)₂CH | H | O | O | CH₃ | DEB |
| 51 | CH₃CH(CH₃)CHO— | (CH₃)₂CH | H | O | O | CH₃ | DEB |
| 52 | CH₃CH₂CH(CH₃)O— | (CH₃)₂CH | H | O | O | CH₃ | DEB |
| 53 | CH₃ | CH₃ | H | S | S | H | TMS |
| 54 | CH₃ | CH₃CH₂ | H | S | S | H | TMS |
| 55 | CH₃ | (CH₃)₂CH | H | S | S | H | TMS |
| 56 | CH₃ | CH₃CH₂CH₂ | H | S | S | H | TMS |
| 57 | CH₃ | CH₃CH₂CH₂CH₂ | H | S | S | H | TMS |
| 58 | CH₃ | (CH₃)₂CH—CH₂ | H | S | S | H | TMS |
| 59 | CH₃ | CH₃CH₂CH(CH₃)— | H | S | S | H | DEB |
| 60 | CH₃ | Ph—CH₂ | CH₃ | S | S | H | DEB |
| 61 | CH₃ | p-CH₃—Ph—CH₂ | H | S | S | H | DEB |
| 62 | CH₃ | 2,4-di-CH₃Ph—CH₂ | CH₃ | S | S | H | DEB |
| 63 | CH₃ | 2,4,5-triCH₃PhCH₂ | H | S | S | H | DEB |
| 64 | CH₃ | 2,4,6-triCH₃PhCH₂ | H | S | S | H | DEB |
| 65 | CH₃ | Ph | H | S | S | H | DEB |
| 66 | CH₃ | CH₃ | H | S | S | Ph | TMS |
| 67 | OCH₃ | CH₃ | HO | S | S | H | TMS |
| 68 | OCH₃ | CH₂CH₂ | H | S | S | H | TMS |
| 69 | OCH₃ | (CH₃)₂CH | H | S | S | H | TMS |
| 70 | OCH₃ | CH₃CH₂CH₂ | H | S | S | H | MST |

TABLE II-continued

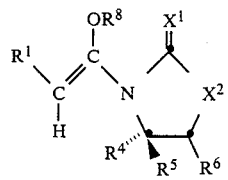

IVA

| Compound | R¹ | R⁴(S) | R⁵(R) | X¹ | X² | R⁶ | R⁸ |
|---|---|---|---|---|---|---|---|
| 71 | OCH₃ | CH₃CH₂CH₂CH₂ | H | S | S | H | MST |
| 72 | OCH₃ | (CH₃)₂CHCH₂ | H | S | S | H | MST |
| 73 | OCH₃ | CH₃CH₂CH(CH₃)— | H | S | S | H | MST |
| 74 | OCH₃ | PhCH₂ | H | S | S | H | MST |
| 75 | OCH₃ | p-CH₃PhCH₂ | H | S | S | H | MST |
| 76 | OCH₃ | 2,4-diCH₃PhCH₂ | CH₃ | S | S | H | TMS |
| 77 | OCH₃ | 2,4-5-triCH₃PhCH₂ | CH₃ | S | S | H | TMS |
| 78 | OCH₃ | 2,4,6-triCH₃PhCH₂ | CH₃ | S | S | H | TMS |
| 79 | OCH₃ | Ph | H | S | S | H | TMS |
| 80 | OCH₃ | CH₃ | H | S | S | Ph | TMS |
| 81 | OCH₃ | CH₃ | H | S | S | Ph | TMS |
| 82 | CH₃ | CH₃ | H | S | S | H | DBB |
| 83 | CH₃ | CH₃CH₂ | H | S | S | H | DBB |
| 84 | CH₃ | (CH₃)₂CH | H | S | S | H | DBB |
| 85 | CH₃ | CH₃CH₂CH₂ | H | S | S | H | DBB |
| 86 | CH₃ | CH₃CH₂CH₂CH₂ | H | S | S | H | DBB |
| 87 | CH₃ | (CH₃)₂CH—CH₂ | H | S | S | H | DBB |
| 88 | CH₃ | CH₃CH₂CH(CH₃)— | H | S | S | H | DBB |
| 89 | CH₃ | Ph—CH₂ | H | S | S | H | DBB |
| 90 | CH₃ | p-CH₃—Ph—CH₂ | H | S | S | H | DBB |
| 91 | CH₃ | 2,4-diCH₃PhCH₂ | H | S | S | H | DBB |
| 92 | CH₃ | 2,4,5-triCH₃PhCH₂ | H | S | S | H | DBB |
| 93 | CH₃ | 2,4,6-triCH₃PhCH₂ | H | S | S | H | DBB |
| 94 | CH₃ | Ph | H | S | S | CH₃ | DBB |
| 95 | CH₃CH₂ | H | CH₃ | S | S | CH₃ | TMS |
| 96 | CH₃CH₂CH₂ | H | Ph | S | S | CH₃ | TMS |
| 97 | (CH₃)₂CH | H | (CH₃)₂CH | S | S | CH₃ | TMS |
| 98 | CH₃CH₂CH₂CH₂ | H | (CH₃)₂CHCH₂ | S | S | CH₃ | TMS |
| 99 | CH₃CH(CH₃)CH₂ | H | CH₃CH₂CH(CH₃)— | S | S | CH₃ | TMS |
| 100 | CH₃CH₂CH(CH₃)— | H | PhCH₂ | S | S | CH₃ | TMS |
| 101 | CH₃CH₂O | (CH₃)₂CH | H | S | S | CH₃ | DEB |
| 102 | CH₃CH₂CH₂O | (CH₃)₂CH | H | S | S | CH₃ | DEB |
| 103 | (CH₃)₂CHO | (CH₃)₂CH | H | S | S | CH₃ | DEB |
| 104 | CH₃CH(CH₃)CHO— | (CH₃)₂CH | H | S | S | CH₃ | DEB |
| 105 | CH₃CH₂CH(CH₃)O— | (CH₃)₂CH | H | S | S | CH₃ | DEB |
| 106 | CH₃ | CH₃ | H | O | S | H | TMS |
| 107 | CH₃ | CH₃CH₂ | H | O | S | H | TMS |
| 108 | CH₃ | (CH₃)₂CH | H | O | S | H | TMS |
| 109 | CH₃ | CH₃CH₂CH₂ | H | O | S | H | TMS |
| 110 | CH₃ | CH₃CH₂CH₂CH₂ | H | O | S | H | TMS |
| 111 | CH₃ | (CH₃)₂CH—CH | H | O | S | H | TMS |
| 112 | CH₃ | CH₃CH₂CH(CH₃)— | H | O | S | H | DEB |
| 113 | CH₃ | Ph—CH₂ | CH₃ | O | S | H | DEB |
| 114 | CH₃ | p-CH₃—Ph—CH₂ | H | O | S | H | DEB |
| 115 | CH₃ | 2,4-di-CH₃Ph—CH₂ | CH₃ | O | S | H | DEB |
| 116 | CH₃ | 2,4,5-triCH₃PhCH₂ | H | O | S | H | DEB |
| 117 | CH₃ | 2,4,6-triCH₃PhCH₂ | H | O | S | H | DEB |
| 118 | CH₃ | Ph | H | O | S | H | DEB |
| 119 | CH₃ | CH₃ | H | O | S | Ph | TMS |
| 120 | OCH₃ | CH₃ | HO | O | S | H | TMS |
| 121 | OCH₃ | CH₂CH₂ | H | O | S | H | TMS |
| 122 | OCH₃ | (CH₃)₂CH | H | O | S | H | TMS |
| 123 | OCH₃ | CH₃CH₂CH₂ | H | O | S | H | MST |
| 124 | OCH₃ | CH₃CH₂CH₂CH₂ | H | O | S | H | MST |
| 125 | OCH₃ | (CH₃)₂CHCH₂ | H | O | S | H | MST |
| 126 | OCH₃ | CH₃CH₂CH(CH₃)— | H | O | S | H | MST |
| 127 | OCH₃ | PhCH₂ | H | O | S | H | MST |
| 128 | OCH₃ | p-CH₃PhCH₂ | H | O | S | H | MST |
| 129 | OCH₃ | 2,4-diCH₃PhCH₃ | CH₃ | O | S | H | TMS |
| 130 | OCH₃ | 2,4-5-triCH₃PhCH₂ | CH₃ | O | S | H | TMS |
| 131 | OCH₃ | 2,4,6-CH₃PhCH₂ | CH₃ | O | S | H | TMS |
| 132 | OCH₃ | Ph | H | O | S | H | TMS |
| 133 | OCH₃ | CH₃ | H | O | S | Ph | TMS |
| 134 | OCH₃ | CH₃ | H | O | S | Ph | TMS |
| 135 | CH₃ | CH₃ | H | O | S | H | DBB |
| 136 | CH₃ | CH₃CH₂ | H | O | S | H | DBB |
| 137 | CH₃ | (CH₃)₂CH | H | O | S | H | DBB |
| 138 | CH₃ | CH₃CH₂CH₂ | H | O | S | H | DBB |
| 139 | CH₃ | CH₃CH₂CH₂CH₂ | H | O | S | H | DBB |
| 140 | CH₃ | (CH₃)₂CH—CH₂ | H | O | S | H | DBB |
| 141 | CH₃ | CH₃CH₂CH(CH₃)— | H | O | S | H | DBB |

TABLE II-continued

IVA $$\begin{array}{c} \text{R}^1\text{-CH=C(OR}^8)\text{-N(ring with R}^4, \text{R}^5, \text{R}^6, \text{X}^2)\text{-C(=X}^1)\text{CH}_3 \end{array}$$

| Compound | R¹ | R⁴(S) | R⁵(R) | X¹ | X² | R⁶ | R⁸ |
|---|---|---|---|---|---|---|---|
| 142 | CH₃ | Ph—CH₂ | H | O | S | H | DBB |
| 143 | CH₃ | p-CH₃—Ph—CH₂ | H | O | S | H | DBB |
| 144 | CH₃ | 2,4-diCH₃PhCH₂ | H | O | S | H | DBB |
| 145 | CH₃ | 2,4,5-triCH₃PhCH₂ | H | O | S | H | DBB |
| 146 | CH₃ | 2,4,6-triCH₃PhCH₂ | H | O | S | H | DBB |
| 147 | CH₃ | Ph | H | O | S | CH₃ | DBB |
| 148 | CH₃CH₂ | H | CH₃ | O | S | CH₃ | TMS |
| 149 | CH₃CH₂CH₂ | H | Ph | O | S | CH₃ | TMS |
| 150 | (CH₃)₂CH | H | (CH₃)₂CH | O | S | CH₃ | TMS |
| 151 | CH₃CH₂CH₂CH₂ | H | (CH₃)₂CHCH₂ | O | S | CH₃ | TMS |
| 152 | CH₃CH(CH₃)CH₂ | H | CH₃CH₂CH(CH₃)— | O | S | CH₃ | TMS |
| 153 | CH₃CH₂CH(CH₃)— | H | PhCH₂ | O | S | CH₃ | TMS |
| 154 | CH₃CH₂O | (CH₃)₂CH | H | O | S | CH₃ | DEB |
| 155 | CH₃CH₂CH₂O | (CH₃)₂CH | H | O | S | CH₃ | DEB |
| 156 | (CH₃)₂CHO | (CH₃)₂CH | H | O | S | CH₃ | DEB |
| 157 | CH₃CH(CH₃)CHO— | (CH₃)₂CH | H | O | S | CH₃ | DEB |
| 158 | CH₃CH₂CH(CH₃)O— | (CH₃)₂CH | H | O | S | CH₃ | DEB |
| 159 | CH₃ | CH₃ | H | S | O | H | TMS |
| 160 | CH₃ | CH₃CH₂ | H | S | O | H | TMS |
| 161 | CH₃ | (CH₃)₂CH | H | S | O | H | TMS |
| 162 | CH₃ | CH₃CH₂CH₂ | H | S | O | H | TMS |
| 163 | CH₃ | CH₃CH₂CH₂CH₂ | H | S | O | H | TMS |
| 164 | CH₃ | (CH₃)₂CH—CH₂ | H | S | O | H | TMS |
| 165 | CH₃ | CH₃CH₂CH(CH₃)— | H | S | O | H | DEB |
| 166 | CH₃ | Ph—CH₂ | CH₃ | S | O | H | DEB |
| 167 | CH₃ | p-CH₃—Ph—CH₂ | H | S | O | H | DEB |
| 168 | CH₃ | 2,4-di-CH₃Ph—CH₂ | CH₃ | S | O | H | DEB |
| 169 | CH₃ | 2,4,5-triCH₃PhCH₂ | H | S | O | H | DEB |
| 170 | CH₃ | 2,4,6-triCH₃PhCH₂ | H | S | O | H | DEB |
| 171 | CH₃ | Ph | H | S | O | H | DEB |
| 172 | CH₃ | CH₃ | H | S | O | Ph | TMS |
| 173 | OCH₃ | CH₃ | HO | S | O | H | TMS |
| 174 | OCH₃ | CH₂CH₂ | H | S | O | H | TMS |
| 175 | OCH₃ | (CH₃)₂CH | H | S | O | H | TMS |
| 176 | OCH₃ | CH₃CH₂CH₂ | H | S | O | H | MST |
| 177 | OCH₃ | CH₃CH₂CH₂CH₂ | H | S | O | H | MST |
| 178 | OCH₃ | (CH₃)₂CHCH₂ | H | S | O | H | MST |
| 179 | OCH₃ | CH₃CH₂CH(CH₃)— | H | S | O | H | MST |
| 180 | OCH₃ | PhCH₂ | H | S | O | H | MST |
| 181 | OCH₃ | p-CH₃PhCH₂ | H | S | O | H | MST |
| 182 | OCH₃ | 2,4-diCH₃PhCH₂ | CH₃ | S | O | H | TMS |
| 183 | OCH₃ | 2,4-5-triCH₃PhCH₂ | CH₃ | S | O | H | TMS |
| 184 | OCH₃ | 2,4,6-triCH₃PhCH₂ | CH₃ | S | O | H | TMS |
| 185 | OCH₃ | Ph | H | S | O | H | TMS |
| 186 | OCH₃ | CH₃ | H | S | O | Ph | TMS |
| 187 | OCH₃ | CH₃ | H | S | O | Ph | TMS |
| 188 | CH₃ | CH₃ | H | S | O | H | DBB |
| 189 | CH₃ | CH₃CH₂ | H | S | O | H | DBB |
| 190 | CH₃ | (CH₃)₂CH | H | S | O | H | DBB |
| 191 | CH₃ | CH₃CH₂CH₂ | H | S | O | H | DBB |
| 192 | CH₃ | CH₃CH₂CH₂CH₂ | H | S | O | H | DBB |
| 193 | CH₃ | (CH₃)₂CH—CH₂ | H | S | O | H | DBB |
| 194 | CH₃ | CH₃CH₂CH(CH₃)— | H | S | O | H | DBB |
| 195 | CH₃ | Ph—CH₂ | H | S | O | H | DBB |
| 196 | CH₃ | p-CH₃—Ph—CH₂ | H | S | O | H | DBB |
| 197 | CH₃ | 2,4-diCH₃PhCH₂ | H | S | O | H | DBB |
| 198 | CH₃ | 2,4,5-triCH₃PhCH₂ | H | S | O | H | DBB |
| 199 | CH₃ | 2,4,6-triCH₃PhCH₂ | H | S | O | H | DBB |
| 200 | CH₃ | Ph | H | S | O | CH₃ | DBB |
| 201 | CH₃CH₂ | H | CH₃ | S | O | CH₃ | TMS |
| 202 | CH₃CH₂CH₂ | H | Ph | S | O | CH₃ | TMS |
| 203 | (CH₃)₂CH | H | (CH₃)₂CH | S | O | CH₃ | TMS |
| 204 | CH₃CH₂CH₂CH₂ | H | (CH₃)₂CHCH₂ | S | O | CH₃ | TMS |
| 205 | CH₃CH(CH₃)CH₂ | H | CH₃CH₂CH(CH₃)— | S | O | CH₃ | TMS |
| 206 | CH₃CH₂CH(CH₃)— | H | PhCH₂ | S | O | CH₃ | TMS |
| 207 | CH₃CH₂O | (CH₃)₂CH | H | S | O | CH₃ | DEB |
| 208 | CH₃CH₂CH₂O | (CH₃)₂CH | H | S | O | CH₃ | DEB |
| 209 | (CH₃)₂CHO | (CH₃)₂CH | H | S | O | CH₃ | DEB |
| 210 | CH₃CH(CH₃)CHO— | (CH₃)₂CH | H | S | O | CH₃ | DEB |

TABLE II-continued

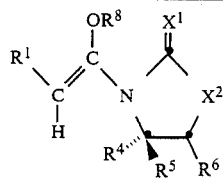
IVA

| Compound | $R^1$ | $R^4(S)$ | $R^5(R)$ | $X^1$ | $X^2$ | $R^6$ | $R^8$ |
|---|---|---|---|---|---|---|---|
| 211 | $CH_3CH_2CH(CH_3)O-$ | $(CH_3)_2CH$ | H | S | O | $CH_3$ | DEB |

Abbreviations used in the Table:
TMS = trimethylsilyl
DEB = diethylboryl
DBB = di-n-butylboryl
Ph = phenyl
MST = $-Sn(II)(CF_3SO_2O)$ [Mono stannous triflate]

The structures and formulas representative of Structure IV in the above Table are not meant to be limiting and other combinations of $R^1$, $R^4$, $R^5$, $R^6$ and $R^8$ not specifically recited herein, which will be obvious to one skilled in the art from the disclosure are also deemed to be included within the scope of this invention.

Preferred examples of structure IVA which are useful in the instant process invention particularly involving a recycle step are

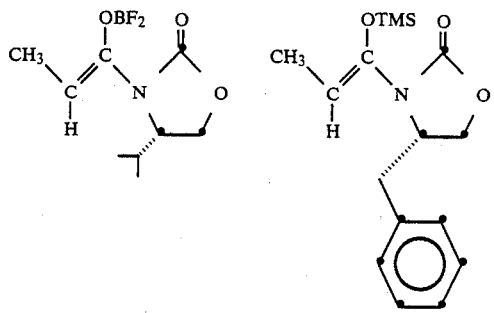

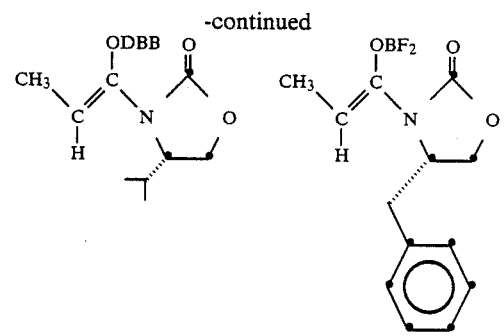

The novel intermediate azetidinone amides of structure II which are also subject compositions in the instant invention include those where $R_1$, $R_2$, $R_3$, $R_4$, $R_5$, $R_6$, $R_7$, and $R_8$ are as herein described above. Several different diastereoisomers of Structure II are included within the scope of this invention, specifically, the trans isomers,

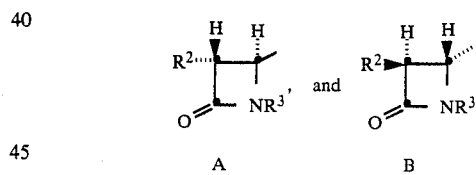

A      B

However, the compounds of Structure A are highly preferred in the practice of the instant invention. Representative examples thereof are given in the Table III below.

TABLE III

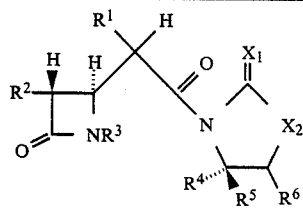
IIA

| Compound | $R^1$ | $R^2$ | $R^3$ | $R^4$ | $R^5$ | $X^1$ | $X^2$ | $R^6$ |
|---|---|---|---|---|---|---|---|---|
| 1 | b-$CH_3$ | HO—$CH_2$ | H | $CH(CH_3)_2$ | H | O | O | H |
| 2 | b-$CH_3$ | $CH_3$—CHOH | H | $CH(CH_3)_2$ | H | O | O | H |
| 3 | b-$CH_3$ | $(CH_3)_2$COH— | H | $CH(CH_3)_2$ | H | O | O | H |
| 4 | b-$CH_3$ | $CH_3CH(O-DMTBS)$ | DMTBS | $CH(CH_3)_2$ | H | O | O | H |
| 5 | b-$CH_3$ | $CH_3CH(O-TMS)$ | H | $CH(CH_3)_2$ | H | O | O | H |
| 6 | b-$CH_3$ | $CH_3CH(O-Bz)$ | H | $CH(CH_3)_2$ | H | O | O | H |
| 7 | b-$CH_3$ | $CH_3CH(O-PNB)$ | H | $CH(CH_3)_2$ | H | O | O | H |

TABLE III-continued

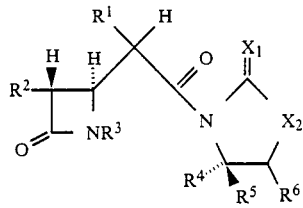

IIA

| Compound | R¹ | R² | R³ | R⁴ | R⁵ | X¹ | X² | R⁶ |
|---|---|---|---|---|---|---|---|---|
| 8 | b-CH₃ | CH₃CH(O—PNBC) | H | CH(CH₃)₂ | H | O | O | H |
| 9 | b-CH₃ | CH₃CH₂CH(OH)— | H | CH(CH₃)₂ | H | O | O | H |
| 10 | b-CH₃ | CH₃CH₂CH₂CH(OH)— | H | CH(CH₃)₂ | H | O | O | H |
| 11 | b-CH₃ | (CH₃)₂CH—CH(OH) | H | CH(CH₃)₂ | H | O | O | H |
| 12 | b-CH₃ | CH₃CH₂C(CH₃)(OH) | H | CH(CH₃)₂ | H | O | O | H |
| 13 | b-CH₃ | HOCH₂ | H | PhCH₂ | H | O | O | H |
| 14 | b-CH₃ | CH₃CHF | TMS | PhCH₂ | H | O | O | H |
| 15 | b-CH₃ | (CH₃)₂COH | H | PhCH₂ | H | O | O | H |
| 16 | b-CH₃ | CH₃CH(O—DMTBS) | H | PhCH₂ | H | O | O | H |
| 17 | b-CH₃ | CH₃CH(O—TMS) | H | PhCH₂ | H | O | O | H |
| 18 | b-CH₃ | CH₃CH(O—Bz) | H | PhCH₂ | H | O | O | H |
| 19 | b-CH₃ | CH₃CH(O—PNB) | H | PhCH₂ | H | O | O | H |
| 20 | b-CH₃ | CH₃CH(O—PNBC) | H | PhCH₂ | H | O | O | H |
| 21 | b-CH₃ | CH₃CH(O—DPTBS) | H | PhCH₂ | H | O | O | H |
| 22 | b-CH₃ | CH₃CH(O—TPS) | H | PhCH₂ | H | O | O | H |
| 23 | b-CH₃ | CH₃CH(O—IPDMS) | H | PhCH₂ | H | O | O | H |
| 24 | b-CH₃ | CH₃CH₂CH(OH) | H | PhCH₂ | H | O | O | H |
| 25 | b-CH₃ | CH₃CH₂CH₂CH(OH) | H | PhCH₂ | H | O | O | H |
| 26 | b-CH₃ | (CH₃)₂CHCH(OH) | H | PhCH₂ | H | O | O | H |
| 27 | b-CH₃ | CH₃CH₂(CH₃)C(OH) | H | PhCH₂ | H | O | O | H |
| 28 | b-CH₃ | (CH₃)₂C(O—PNB) | H | PhCH₂ | H | O | O | H |
| 29 | b-CH₃ | CH₃CH₂CH(O—DPTBS) | H | PhCH₂ | H | O | O | H |
| 30 | b-CH₃ | HOCH₂ | H | (CH₃)₂CHCH₂ | H | O | O | H |
| 31 | b-CH₃ | FH₂CHOH | H | (CH₃)₂CHCH₂ | H | O | O | H |
| 32 | b-CH₃ | (CH₃)₂COH | H | (CH₃)₂CHCH₂ | H | O | O | H |
| 33 | b-CH₃ | CH₃CH(O—DMTBS) | H | (CH₃)₂CHCH₂ | H | O | O | H |
| 34 | b-CH₃ | CH₃CH(O—TMS) | H | (CH₃)₂CHCH₂ | H | O | O | H |
| 35 | b-CH₃ | CH₃CH(O—Bz) | H | (CH₃)₂CHCH₂ | H | O | O | H |
| 36 | b-CH₃ | CH₃CH(O—PNB) | H | (CH₃)₂CHCH₂ | H | O | O | H |
| 37 | b-CH₃ | CH₃CH(O—PNCB) | H | (CH₃)₂CHCH₂ | H | O | O | H |
| 38 | b-CH₃ | CH₃CH(O—DPTBS) | H | (CH₃)₂CHCH₂ | H | O | O | H |
| 39 | b-CH₃ | CH₃CH(O—TPS) | H | (CH₃)₂CHCH₂ | H | O | O | H |
| 40 | b-CH₃ | CH₃CH(O—IPDMS) | H | (CH₃)₂CHCH₂ | H | O | O | H |
| 41 | b-CH₃ | CH₃CH₂CH(OH) | H | (CH₃)₂CHCH₂ | H | O | O | H |
| 42 | b-CH₃ | CH₃CH₂CH₂CH(OH) | H | (CH₃)₂CHCH₂ | H | O | O | H |
| 43 | b-CH₃ | (CH₃)₂CHCH(OH) | H | (CH₃)₂CHCH₂ | H | O | O | H |
| 44 | b-CH₃ | CH₃CH₂(CH₃)C(OH) | H | (CH₃)₂CHCH₂ | H | O | O | H |
| 45 | b-CH₃ | (CH₃)₂C(O—PNB) | H | (CH₃)₂CHCH₂ | H | O | O | H |
| 46 | b-CH₃ | CH₃CH₂CH(O—DPTBS) | H | (CH₃)₂CHCH₂ | H | O | O | H |
| 47 | b-CH₃ | HOCH₂ | H | CH₃CH₂(CH₃)CH— | H | O | O | H |
| 48 | b-CH₃ | CH₃CHOH | H | CH₃CH₂(CH₃)CH— | H | O | O | H |
| 49 | b-CH₃ | (CH₃)₂COH | H | CH₃CH₂(CH₃)CH— | H | O | O | H |
| 50 | b-CH₃ | CH₃CH(O—DMTBS) | H | CH₃CH₂(CH₃)CH— | H | O | O | H |
| 51 | b-CH₃ | CH₃CH(O—TMS) | H | CH₃CH₂(CH₃)CH— | H | O | O | H |
| 52 | b-CH₃ | CH₃CH(O—Bz) | H | CH₃CH₂(CH₃)CH— | H | O | O | H |
| 53 | b-CH₃ | CH₃CH(O—PNB) | H | CH₃CH₂(CH₃)CH— | H | O | O | H |
| 54 | b-CH₃ | CH₃CH(O—PNCB) | H | CH₃CH₂(CH₃)CH— | H | O | O | H |
| 55 | b-CH₃ | CH₃CH(O—DPTBS) | H | CH₃CH₂(CH₃)CH— | H | O | O | H |
| 56 | b-CH₃ | CH₃CH(O—TPS) | H | CH₃CH₂(CH₃)CH— | H | O | O | H |
| 57 | b-CH₃ | CH₃CH(O—IPDMS) | H | CH₃CH₂(CH₃)CH— | H | O | O | H |
| 58 | b-CH₃ | CH₃CH₂CH(OH) | H | CH₃CH₂(CH₃)CH— | H | O | O | H |
| 59 | b-CH₃ | CH₃CH₂CH₂CH(OH) | H | CH₃CH₂(CH₃)CH— | H | O | O | H |
| 60 | b-CH₃ | (CH₃)₂CHCH(OH) | H | CH₃CH₂(CH₃)CH— | H | O | O | H |
| 61 | b-CH₃ | CH₃CH₂(CH₃)C(OH) | H | CH₃CH₂(CH₃)CH— | H | O | O | H |
| 62 | b-CH₃ | (CH₃)₂C(O—PNB) | H | CH₃CH₂(CH₃)CH— | H | O | O | H |
| 63 | b-CH₃ | CH₃CH₂CH(O—DPTBS) | H | CH₃CH₂(CH₃)CH— | H | O | O | H |
| 64 | b-CH₃ | HOCH₂ | H | CH₃ | H | O | O | a-Ph |
| 65 | b-CH₃ | CH₃CHOH | H | CH₃ | H | O | O | a-Ph |
| 66 | b-CH₃ | (CH₃)₂COH | H | CH₃ | H | O | O | a-Ph |
| 67 | b-CH₃ | CH₃CH(O—DMTBS) | H | CH₃ | H | O | O | a-Ph |
| 68 | b-CH₃ | CH₃CH(O—TMS) | H | CH₃ | H | O | O | a-Ph |
| 69 | b-CH₃ | CH₃CH(O—Bz) | H | CH₃ | H | O | O | a-Ph |
| 70 | b-CH₃ | CH₃CH(O—PNB) | H | CH₃ | H | O | O | a-Ph |
| 71 | b-CH₃ | CH₃CH(O—PNCB) | H | CH₃ | H | O | O | a-Ph |
| 72 | b-CH₃ | CH₃CH(O—DPTBS) | H | CH₃ | H | O | O | a-Ph |
| 73 | b-CH₃ | CH₃CH(O—TPS) | H | CH₃ | H | O | O | a-Ph |
| 74 | b-CH₃ | CH₃CH(O—IPDMS) | H | CH₃ | H | O | O | a-Ph |
| 75 | b-CH₃ | CH₃CH₂CH(OH) | H | CH₃ | H | O | O | a-Ph |
| 76 | b-CH₃ | CH₃CH₂CH₂CH(OH) | H | CH₃ | H | O | O | a-Ph |
| 77 | b-CH₃ | (CH₃)₂CHCH(OH) | H | CH₃ | H | O | O | a-Ph |

TABLE III-continued

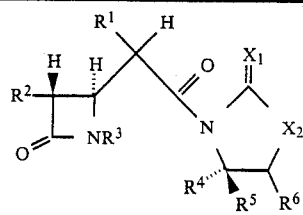

IIA

| Compound | R¹ | R² | R³ | R⁴ | R⁵ | X¹ | X² | R⁶ |
|---|---|---|---|---|---|---|---|---|
| 78 | b-CH₃ | CH₃CH₂(CH₃)C(OH) | H | CH₃ | H | O | O | a-Ph |
| 79 | b-CH₃ | (CH₃)₂C(O—PNB) | H | CH₃ | H | O | O | a-Ph |
| 80 | b-CH₃ | CH₃CH₂CH(O—DPTBS) | H | CH₃ | H | O | O | a-Ph |
| 81 | a-CH₃ | CH₃CH(O—DMTBS) | PNBC | H | CH(CH₃)₂ | O | O | H |
| 82 | a-CH₃ | CH₃CH(O—DMTBS) | PNBC | H | CH(CH₃)₂ | O | O | H |
| 83 | a-CH₃ | CH₃CH(O—DMTBS) | PNBC | H | CH(CH₃)₂ | O | O | H |
| 84 | b-CH₃CH₂ | CH₃CH(O—DMTBS) | DMTBS | PhCH₂ | H | O | O | H |
| 85 | b-CH₃CH₂ | CH₃CH(O—DMTBS) | DMTBS | PhCH₂ | H | O | O | H |
| 86 | b-CH₃CH₂ | CH₃CH(O—DMTBS) | DMTBS | PhCH₂ | H | O | O | H |
| 87 | a-CH(CH₃)₂ | CH₃CH(O—DMTBS) | Bz | H | CH₃ | O | O | b-Ph |
| 88 | a-CH(CH₃)₂ | CH₃CH(O—DMTBS) | Bz | H | CH₃ | O | O | b-Ph |
| 89 | a-CH(CH₃)₂ | CH₃CH(O—DMTBS) | Bz | H | CH₃ | O | O | b-Ph |
| 90 | b-OCH₃ | CH₃CH(O—DMTBS) | PNB | (CH₃)₂CHCH— | H | O | O | H |
| 91 | b-OCH₃ | CH₃CH(O—DMTBS) | PNB | (CH₃)₂CHCH— | H | O | O | H |
| 92 | b-OCH₃ | CH₃CH(O—DMTBS) | PNB | (CH₃)₂CHCH— | H | O | O | H |
| 93 | a-OCH₂CH₃ | CH₃CH(O—DMTBS) | PNB | H | CH₃CH₂(CH₃CH— | O | O | H |
| 94 | a-OCH₂CH₃ | CH₃CH(O—DMTBS) | PNB | H | CH₃CH₂(CH₃CH— | O | O | H |
| 95 | a-OCH₂CH₃ | CH₃CH(O—DMTBS) | PNB | H | CH₃CH₂(CH₃CH— | O | O | H |
| 96 | a-OCH₂CH₂CH₃ | CH₃CH(O—DMTBS) | PNB | H | Ph | O | O | H |
| 97 | a-OCH₂CH₂CH₃ | CH₃CH(O—DMTBS) | PNB | H | Ph | O | O | H |
| 98 | a-OCH₂CH₂CH₃ | CH₃CH(O—DMTBS) | PNB | H | Ph | O | O | H |
| 99 | a-CH₃CH₂ | CH₃CH(O—DMTBS) | PNB | H | CH₃ | O | O | H |
| 100 | a-CH₃CH₂ | CH₃CH(O—DMTBS) | PNB | H | CH₃ | O | O | H |
| 101 | a-CH₃CH₂ | CH₃CH(O—DMTBS) | PNB | H | CH₃ | O | O | H |
| 102 | a-OCH₃ | CH₃CH(O—DMTBS) | PNB | H | CH₃ | O | O | H |
| 103 | a-OCH₃ | CH₃CH(O—DMTBS) | PNB | H | CH₃ | O | O | H |
| 104 | b-CH₃ | HO—CH₂ | H | CH(CH₃)₂ | H | S | S | H |
| 105 | b-CH₃ | CH₃—CHOH | H | CH(CH₃)₂ | H | S | S | H |
| 106 | b-CH₃ | (CH₃)₂COH— | H | CH(CH₃)₂ | H | S | S | H |
| 107 | b-CH₃ | CH₃CH(O—DMTBS) | DMTBS | CH(CH₃)₂ | H | S | S | H |
| 108 | b-CH₃ | CH₃CH(O—TMS) | H | CH(CH₃)₂ | H | S | S | H |
| 109 | b-CH₃ | CH₃CH(O—Bz) | H | CH(CH₃)₂ | H | S | S | H |
| 110 | b-CH₃ | CH₃CH(O—PNB) | H | CH(CH₃)₂ | H | S | S | H |
| 111 | b-CH₃ | CH₃CH(O—PNBC) | H | CH(CH₃)₂ | H | S | S | H |
| 112 | b-CH₃ | CH₃CH₂CH(OH)— | H | CH(CH₃)₂ | H | S | S | H |
| 113 | b-CH₃ | CH₃CH₂CH₂CH(OH)— | H | CH(CH₃)₂ | H | S | S | H |
| 114 | b-CH₃ | (CH₃)₂CH—CH(OH) | H | CH(CH₃)₂ | H | S | S | H |
| 115 | b-CH₃ | CH₃CH₂C(CH₃)(OH) | H | CH(CH₃)₂ | H | S | S | H |
| 116 | b-CH₃ | HOCH₂ | H | PhCH₂ | H | S | S | H |
| 117 | b-CH₃ | CH₃CHF | TMS | PhCH₂ | H | S | S | H |
| 118 | b-CH₃ | (CH₃)₂COH | H | PhCH₂ | H | S | S | H |
| 119 | b-CH₃ | CH₃CH(O—DMTBS) | H | PhCH₂ | H | S | S | H |
| 120 | b-CH₃ | CH₃CH(O—TMS) | H | PhCH₂ | H | S | S | H |
| 121 | b-CH₃ | CH₃CH(O—Bz) | H | PhCH₂ | H | S | S | H |
| 122 | b-CH₃ | CH₃CH(O—PNB) | H | PhCH₂ | H | S | S | H |
| 123 | b-CH₃ | CH₃CH(O—PNBC) | H | PhCH₂ | H | S | S | H |
| 124 | b-CH₃ | CH₃CH(O—DPTBS) | H | PhCH₂ | H | S | S | H |
| 125 | b-CH₃ | CH₃CH(O—TPS) | H | PhCH₂ | H | S | S | H |
| 126 | b-CH₃ | CH₃CH(O—IPDMS) | H | PhCH₂ | H | S | S | H |
| 127 | b-CH₃ | CH₃CH₂CH(OH) | H | PhCH₂ | H | S | S | H |
| 128 | b-CH₃ | CH₃CH₂CH₂CH(OH) | H | PhCH₃ | H | S | S | H |
| 129 | b-CH₃ | (CH₃)₂CHCH(OH) | H | PhCH₂ | H | S | S | H |
| 130 | b-CH₃ | CH₃CH₂(CH₃)C(OH) | H | PhCH₂ | H | S | S | H |
| 131 | b-CH₃ | (CH₃)₂C(O—PNB) | H | PhCH₂ | H | S | S | H |
| 132 | b-CH₃ | CH₃CH₂CH(O—DPTBS) | H | PhCH₂ | H | S | S | H |
| 133 | b-CH₃ | HOCH₂ | H | (CH₃)₂CHCH₂ | H | S | S | H |
| 134 | b-CH₃ | FH₂CHOH | H | (CH₃)₂CHCH₂ | H | S | S | H |
| 135 | b-CH₃ | (CH₃)₂COH | H | (CH₃)₂CHCH₂ | H | S | S | H |
| 136 | b-CH₃ | CH₃CH(O—DMTBS) | H | (CH₃)₂CHCH₂ | H | S | S | H |
| 137 | b-CH₃ | CH₃CH(O—TMS) | H | (CH₃)₂CHCH₂ | H | S | S | H |
| 138 | b-CH₃ | CH₃CH(O—Bz) | H | (CH₃)₂CHCH₂ | H | S | S | H |
| 139 | b-CH₃ | CH₃CH(O—PNB) | H | (CH₃)₂CHCH₂ | H | S | S | H |
| 140 | b-CH₃ | CH₃CH(O—PNCB) | H | (CH₃)₂CHCH₂ | H | S | S | H |
| 141 | b-CH₃ | CH₃CH(O—DPTBS) | H | (CH₃)₂CHCH₂ | H | S | S | H |
| 142 | b-CH₃ | CH₃CH(O—TPS) | H | (CH₃)₂CHCH₂ | H | S | S | H |
| 143 | b-CH₃ | CH₃CH(O—IPDMS) | H | (CH₃)₂CHCH₂ | H | S | S | H |
| 144 | b-CH₃ | CH₃CH₂CH(OH) | H | (CH₃)₂CHCH₂ | H | S | S | H |
| 145 | b-CH₃ | CH₃CH₂CH₂CH(OH) | H | (CH₃)₂CHCH₂ | H | S | S | H |
| 146 | b-CH₃ | (CH₃)₂CHCH(OH) | H | (CH₃)₂CHCH₂ | H | S | S | H |
| 147 | b-CH₃ | CH₃CH₂(CH₃)C(OH) | H | (CH₃)₂CHCH₂ | H | S | S | H |

TABLE III-continued

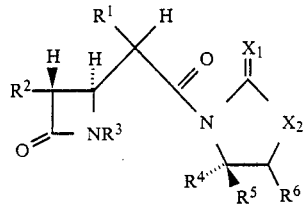

IIA

| Compound | R¹ | R² | R³ | R⁴ | R⁵ | X¹ | X² | R⁶ |
|---|---|---|---|---|---|---|---|---|
| 148 | b-$CH_3$ | $(CH_3)_2C(O-PNB)$ | H | $(CH_3)_2CHCH_2$ | H | S | S | H |
| 149 | b-$CH_3$ | $CH_3CH_2CH(O-DPTBS)$ | H | $(CH_3)_2CHCH_2$ | H | S | S | H |
| 150 | b-$CH_3$ | $HOCH_2$ | H | $CH_3CH_2(CH_3)CH-$ | H | S | S | H |
| 151 | b-$CH_3$ | $CH_3CHOH$ | H | $CH_3CH_2(CH_3)CH-$ | H | S | S | H |
| 152 | b-$CH_3$ | $(CH_3)_2COH$ | H | $CH_3CH_2(CH_3)CH-$ | H | S | S | H |
| 153 | b-$CH_3$ | $CH_3CH(O-DMTBS)$ | H | $CH_3CH_2(CH_3)CH-$ | H | S | S | H |
| 154 | b-$CH_3$ | $CH_3CH(O-TMS)$ | H | $CH_3CH_2(CH_3)CH-$ | H | S | S | H |
| 155 | b-$CH_3$ | $CH_3CH(O-Bz)$ | H | $CH_3CH_2(CH_3)CH-$ | H | S | S | H |
| 156 | b-$CH_3$ | $CH_3CH(O-PNB)$ | H | $CH_3CH_2(CH_3)CH-$ | H | S | S | H |
| 157 | b-$CH_3$ | $CH_3CH(O-PNCB)$ | H | $CH_3CH_2(CH_3)CH-$ | H | S | S | H |
| 158 | b-$CH_3$ | $CH_3CH(O-DPTBS)$ | H | $CH_3CH_2(CH_3)CH-$ | H | S | S | H |
| 159 | b-$CH_3$ | $CH_3CH(O-TPS)$ | H | $CH_3CH_2(CH_3)CH-$ | H | S | S | H |
| 160 | b-$CH_3$ | $CH_3CH(O-IPDMS)$ | H | $CH_3CH_2(CH_3)CH-$ | H | S | S | H |
| 161 | b-$CH_3$ | $CH_3CH_2CH(OH)$ | H | $CH_3CH_2(CH_3)CH-$ | H | S | S | H |
| 162 | b-$CH_3$ | $CH_3CH_2CH_2CH(OH)$ | H | $CH_3CH_2(CH_3)CH-$ | H | S | S | H |
| 163 | b-$CH_3$ | $(CH_3)_2CHCH(OH)$ | H | $CH_3CH_2(CH_3)CH-$ | H | S | S | H |
| 164 | b-$CH_3$ | $CH_3CH_2(CH_3)C(OH)$ | H | $CH_3CH_2(CH_3)CH-$ | H | S | S | H |
| 165 | b-$CH_3$ | $(CH_3)_2C(O-PNB)$ | H | $CH_3CH_2(CH_3)CH-$ | H | S | S | H |
| 166 | b-$CH_3$ | $CH_3CH_2CH(O-DPTBS)$ | H | $CH_3CH_2(CH_3)CH-$ | H | S | S | H |
| 167 | b-$CH_3$ | $HOCH_2$ | H | $CH_3$ | H | S | S | a-Ph |
| 168 | b-$CH_3$ | $CH_3CHOH$ | H | $CH_3$ | H | S | S | a-Ph |
| 169 | b-$CH_3$ | $(CH_3)_2COH$ | H | $CH_3$ | H | S | S | a-Ph |
| 170 | b-$CH_3$ | $CH_3CH(O-DMTBS)$ | H | $CH_3$ | H | S | S | a-Ph |
| 171 | b-$CH_3$ | $CH_3CH(O-TMS)$ | H | $CH_3$ | H | S | S | a-Ph |
| 172 | b-$CH_3$ | $CH_3CH(O-Bz)$ | H | $CH_3$ | H | S | S | a-Ph |
| 173 | b-$CH_3$ | $CH_3CH(O-PNB)$ | H | $CH_3$ | H | S | S | a-Ph |
| 174 | b-$CH_3$ | $CH_3CH(O-PNCB)$ | H | $CH_3$ | H | S | S | a-Ph |
| 175 | b-$CH_3$ | $CH_3CH(O-DPTBS)$ | H | $CH_3$ | H | S | S | a-Ph |
| 176 | b-$CH_3$ | $CH_3CH(O-TPS)$ | H | $CH_3$ | H | S | S | a-Ph |
| 177 | b-$CH_3$ | $CH_3CH(O-IPDMS)$ | H | $CH_3$ | H | S | S | a-Ph |
| 178 | b-$CH_3$ | $CH_3CH_2CH(OH)$ | H | $CH_3$ | H | S | S | a-Ph |
| 179 | b-$CH_3$ | $CH_3CH_2CH_2CH(OH)$ | H | $CH_3$ | H | S | S | a-Ph |
| 180 | b-$CH_3$ | $(CH_3)_2CHCH(OH)$ | H | $CH_3$ | H | S | S | a-Ph |
| 181 | b-$CH_3$ | $CH_3CH_2(CH_3)C(OH)$ | H | $CH_3$ | H | S | S | a-Ph |
| 182 | b-$CH_3$ | $(CH_3)_2C(O-PNB)$ | H | $CH_3$ | H | S | S | a-Ph |
| 183 | b-$CH_3$ | $CH_3CH_2CH(O-DPTBS)$ | H | $CH_3$ | H | S | S | a-Ph |
| 184 | a-$CH_3$ | $CH_3CH(O-DMTBS)$ | PNBC | H | $CH(CH_3)_2$ | S | S | H |
| 185 | a-$CH_3$ | $CH_3CH(O-DMTBS)$ | PNBC | H | $CH(CH_3)_2$ | S | S | H |
| 186 | a-$CH_3$ | $CH_3CH(O-DMTBS)$ | PNBC | H | $CH(CH_3)_2$ | S | S | H |
| 187 | b-$CH_3CH_2$ | $CH_3CH(O-DMTBS)$ | DMTBS | $PhCH_2$ | H | S | S | H |
| 188 | b-$CH_3CH_2$ | $CH_3CH(O-DMTBS)$ | DMTBS | $PhCH_2$ | H | S | S | H |
| 189 | b-$CH_3CH_2$ | $CH_3CH(O-DMTBS)$ | DMTBS | $PhCH_2$ | H | S | S | H |
| 190 | a-$CH(CH_3)_2$ | $CH_3CH(O-DMTBS)$ | Bz | H | $CH_3$ | S | S | b-Ph |
| 191 | a-$CH(CH_3)_2$ | $CH_3CH(O-DMTBS)$ | Bz | H | $CH_3$ | S | S | b-Ph |
| 192 | a-$CH(CH_3)_2$ | $CH_3CH(O-DMTBS)$ | Bz | H | $CH_3$ | S | S | b-Ph |
| 193 | b-$OCH_3$ | $CH_3CH(O-DMTBS)$ | PNB | $(CH_3)_2CHCH-$ | H | S | S | H |
| 194 | b-$OCH_3$ | $CH_3CH(O-DMTBS)$ | PNB | $(CH_3)_2CHCH-$ | H | S | S | H |
| 195 | b-$OCH_3$ | $CH_3CH(O-DMTBS)$ | PNB | $(CH_3)_2CHCH-$ | H | S | S | H |
| 196 | a-$OCH_2CH_3$ | $CH_3CH(O-DMTBS)$ | PNB | H | $CH_3CH_2(CH_3CH-$ | S | S | H |
| 197 | a-$OCH_2CH_3$ | $CH_3CH(O-DMTBS)$ | PNB | H | $CH_3CH_2(CH_3CH-$ | S | S | H |
| 198 | a-$OCH_2CH_3$ | $CH_3CH(O-DMTBS)$ | PNB | H | $CH_3CH_2(CH_3CH-$ | S | S | H |
| 199 | a-$OCH_2CH_2CH_3$ | $CH_3CH(O-DMTBS)$ | PNB | H | Ph | S | S | H |
| 200 | a-$OCH_2CH_2CH_3$ | $CH_3CH(O-DMTBS)$ | PNB | H | Ph | S | S | H |
| 201 | a-$OCH_2CH_2CH_3$ | $CH_3CH(O-DMTBS)$ | PNB | H | Ph | S | S | H |
| 202 | a-$CH_3CH_2$ | $CH_3CH(O-DMTBS)$ | PNB | H | $CH_3$ | S | S | H |
| 203 | a-$CH_3CH_2$ | $CH_3CH(O-DMTBS)$ | PNB | H | $CH_3$ | S | S | H |
| 204 | a-$CH_3CH_2$ | $CH_3CH(O-DMTBS)$ | PNB | H | $CH_3$ | S | S | H |
| 205 | a-$OCH_3$ | $CH_3CH(O-DMTBS)$ | PNB | H | $CH_3$ | S | S | H |
| 206 | a-$OCH_3$ | $CH_3CH(O-DMTBS)$ | PNB | H | $CH_3$ | S | S | H |
| 207 | b-$CH_3$ | $HO-CH_2$ | H | $CH(CH_3)_2$ | H | O | S | H |
| 208 | b-$CH_3$ | $CH_3-CHOH$ | H | $CH(CH_3)_2$ | H | O | S | H |
| 209 | b-$CH_3$ | $(CH_3)_2COH-$ | H | $CH(CH_3)_2$ | H | O | S | H |
| 210 | b-$CH_3$ | $CH_3CH(O-DMTBS)$ | DMTBS | $CH(CH_3)_2$ | H | O | S | H |
| 211 | b-$CH_3$ | $CH_3CH(O-TMS)$ | H | $CH(CH_3)_2$ | H | O | S | H |
| 212 | b-$CH_3$ | $CH_3CH(O-Bz)$ | H | $CH(CH_3)_2$ | H | O | S | H |
| 213 | b-$CH_3$ | $CH_3CH(O-PNB)$ | H | $CH(CH_3)_2$ | H | O | S | H |
| 214 | b-$CH_3$ | $CH_3CH(O-PNBC)$ | H | $CH(CH_3)_2$ | H | O | S | H |
| 215 | b-$CH_3$ | $CH_3CH_2CH(OH)-$ | H | $CH(CH_3)_2$ | H | O | S | H |
| 216 | b-$CH_3$ | $CH_3CH_2CH_2CH(OH)-$ | H | $CH(CH_3)_2$ | H | O | S | H |
| 217 | b-$CH_3$ | $(CH_3)_2CH-CH(OH)$ | H | $CH(CH_3)_2$ | H | O | S | H |

TABLE III-continued

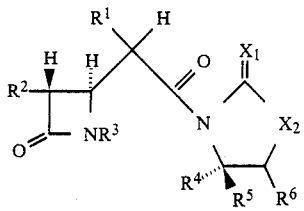

IIA

| Compound | R$^1$ | R$^2$ | R$^3$ | R$^4$ | R$^5$ | X$^1$ | X$^2$ | R$^6$ |
|---|---|---|---|---|---|---|---|---|
| 218 | b-CH$_3$ | CH$_3$CH$_2$C(CH$_3$)(OH) | H | CH(CH$_3$)$_2$ | H | O | S | H |
| 219 | b-CH$_3$ | HOCH$_2$ | H | PhCH$_2$ | H | O | S | H |
| 220 | b-CH$_3$ | CH$_3$CHF | TMS | PhCH$_2$ | H | O | S | H |
| 221 | b-CH$_3$ | (CH$_3$)$_2$COH | H | PhCH$_2$ | H | O | S | H |
| 222 | b-CH$_3$ | CH$_3$CH(O—DMTBS) | H | PhCH$_2$ | H | O | S | H |
| 223 | b-CH$_3$ | CH$_3$CH(O—TMS) | H | PhCH$_2$ | H | O | S | H |
| 224 | b-CH$_3$ | CH$_3$CH(O—Bz) | H | PhCH$_2$ | H | O | S | H |
| 225 | b-CH$_3$ | CH$_3$CH(O—PNB) | H | PhCH$_2$ | H | O | S | H |
| 226 | b-CH$_3$ | CH$_3$CH(O—PNBC) | H | PhCH$_2$ | H | O | S | H |
| 227 | b-CH$_3$ | CH$_3$CH(O—DPTBS) | H | PhCH$_2$ | H | O | S | H |
| 228 | b-CH$_3$ | CH$_3$CH(O—TPS) | H | PhCH$_2$ | H | O | S | H |
| 229 | b-CH$_3$ | CH$_3$CH(O—IPDMS) | H | PhCH$_2$ | H | O | S | H |
| 230 | b-CH$_3$ | CH$_3$CH$_2$CH(OH) | H | PhCH$_2$ | H | O | S | H |
| 231 | b-CH$_3$ | CH$_3$CH$_2$CH$_2$CH(OH) | H | PhCH$_2$ | H | O | S | H |
| 232 | b-CH$_3$ | (CH$_3$)$_2$CHCH(OH) | H | PhCH$_2$ | H | O | S | H |
| 233 | b-CH$_3$ | CH$_3$CH$_2$(CH$_3$)C(OH) | H | PhCH$_2$ | H | O | S | H |
| 234 | b-CH$_3$ | (CH$_3$)$_2$C(O—PNB) | H | PhCH$_2$ | H | O | S | H |
| 235 | b-CH$_3$ | CH$_3$CH$_2$CH(O—DPTBS) | H | PhCH$_2$ | H | O | S | H |
| 236 | b-CH$_3$ | HOCH$_2$ | H | (CH$_3$)$_2$CHCH$_2$ | H | O | S | H |
| 237 | b-CH$_3$ | FH$_2$CHOH | H | (CH$_3$)$_2$CHCH$_2$ | H | O | S | H |
| 238 | b-CH$_3$ | (CH$_3$)$_2$COH | H | (CH$_3$)$_2$CHCH$_2$ | H | O | S | H |
| 239 | b-CH$_3$ | CH$_3$CH(O—DMTBS) | H | (CH$_3$)$_2$CHCH$_2$ | H | O | S | H |
| 240 | b-CH$_3$ | CH$_3$CH(O—TMS) | H | (CH$_3$)$_2$CHCH$_2$ | H | O | S | H |
| 241 | b-CH$_3$ | CH$_3$CH(O—Bz) | H | (CH$_3$)$_2$CHCH$_2$ | H | O | S | H |
| 242 | b-CH$_3$ | CH$_3$CH(O—PNB) | H | (CH$_3$)$_2$CHCH$_2$ | H | O | S | H |
| 243 | b-CH$_3$ | CH$_3$CH(O—PNCB) | H | (CH$_3$)$_2$CHCH$_2$ | H | O | S | H |
| 244 | b-CH$_3$ | CH$_3$CH(O—DPTBS) | H | (CH$_3$)$_2$CHCH$_2$ | H | O | S | H |
| 245 | b-CH$_3$ | CH$_3$CH(O—TPS) | H | (CH$_3$)$_2$CHCH$_2$ | H | O | S | H |
| 246 | b-CH$_3$ | CH$_3$CH(O—IPDMS) | H | (CH$_3$)$_2$CHCH$_2$ | H | O | S | H |
| 247 | b-CH$_3$ | CH$_3$CH$_2$CH(OH) | H | (CH$_3$)$_2$CHCH$_2$ | H | O | S | H |
| 248 | b-CH$_3$ | CH$_3$CH$_2$CH$_2$CH(OH) | H | (CH$_3$)$_2$CHCH$_2$ | H | O | S | H |
| 249 | b-CH$_3$ | (CH$_3$)$_2$CHCH(OH) | H | (CH$_3$)$_2$CHCH$_2$ | H | O | S | H |
| 250 | b-CH$_3$ | CH$_3$CH$_2$(CH$_3$)C(OH) | H | (CH$_3$)$_2$CHCH$_2$ | H | O | S | H |
| 251 | b-CH$_3$ | (CH$_3$)$_2$C(O—PNB) | H | (CH$_3$)$_2$CHCH$_2$ | H | O | S | H |
| 252 | b-CH$_3$ | CH$_3$CH$_2$CH(O—DPTBS) | H | (CH$_3$)$_2$CHCH$_2$ | H | O | S | H |
| 253 | b-CH$_3$ | HOCH$_2$ | H | CH$_3$CH$_2$(CH$_3$)CH— | H | O | S | H |
| 254 | b-CH$_3$ | CH$_3$CHOH | H | CH$_3$CH$_2$(CH$_3$)CH— | H | O | S | H |
| 255 | b-CH$_3$ | (CH$_3$)$_2$COH | H | CH$_3$CH$_2$(CH$_3$)CH— | H | O | S | H |
| 256 | b-CH$_3$ | CH$_3$CH(O—DMTBS) | H | CH$_3$CH$_2$(CH$_3$)CH— | H | O | S | H |
| 257 | b-CH$_3$ | CH$_3$CH(O—TMS) | H | CH$_3$CH$_2$(CH$_3$)CH— | H | O | S | H |
| 258 | b-CH$_3$ | CH$_3$CH(O—Bz) | H | CH$_3$CH$_2$(CH$_3$)CH— | H | O | S | H |
| 259 | b-CH$_3$ | CH$_3$CH(O—PNB) | H | CH$_3$CH$_2$(CH$_3$)CH— | H | O | S | H |
| 260 | b-CH$_3$ | CH$_3$CH(O—PNCB) | H | CH$_3$CH$_2$(CH$_3$)CH— | H | O | S | H |
| 261 | b-CH$_3$ | CH$_3$CH(O—DPTBS) | H | CH$_3$CH$_2$(CH$_3$)CH— | H | O | S | H |
| 262 | b-CH$_3$ | CH$_3$CH(O—TPS) | H | CH$_3$CH$_2$(CH$_3$)CH— | H | O | S | H |
| 263 | b-CH$_3$ | CH$_3$CH(O—IPDMS) | H | CH$_3$CH$_2$(CH$_3$)CH— | H | O | S | H |
| 264 | b-CH$_3$ | CH$_3$CH$_2$CH(OH) | H | CH$_3$CH$_2$(CH$_3$)CH— | H | O | S | H |
| 265 | b-CH$_3$ | CH$_3$CH$_2$CH$_2$CH(OH) | H | CH$_3$CH$_2$(CH$_3$)CH— | H | O | S | H |
| 266 | b-CH$_3$ | (CH$_3$)$_2$CHCH(OH) | H | CH$_3$CH$_2$(CH$_3$)CH— | H | O | S | H |
| 267 | b-CH$_3$ | CH$_3$CH$_2$(CH$_3$)C(OH) | H | CH$_3$CH$_2$(CH$_3$)CH— | H | O | S | H |
| 268 | b-CH$_3$ | (CH$_3$)$_2$C(O—PNB) | H | CH$_3$CH$_2$(CH$_3$)CH— | H | O | S | H |
| 269 | b-CH$_3$ | CH$_3$CH$_2$CH(O—DPTBS) | H | CH$_3$CH$_2$(CH$_3$)CH— | H | O | S | H |
| 270 | b-CH$_3$ | HOCH$_2$ | H | CH$_3$ | H | O | S | a-Ph |
| 271 | b-CH$_3$ | CH$_3$CHOH | H | CH$_3$ | H | O | S | a-Ph |
| 272 | b-CH$_3$ | (CH$_3$)$_2$COH | H | CH$_3$ | H | O | S | a-Ph |
| 273 | b-CH$_3$ | CH$_3$CH(O—DMTBS) | H | CH$_3$ | H | O | S | a-Ph |
| 274 | b-CH$_3$ | CH$_3$CH(O—TMS) | H | CH$_3$ | H | O | S | a-Ph |
| 275 | b-CH$_3$ | CH$_3$CH(O—Bz) | H | CH$_3$ | H | O | S | a-Ph |
| 276 | b-CH$_3$ | CH$_3$CH(O—PNB) | H | CH$_3$ | H | O | S | a-Ph |
| 277 | b-CH$_3$ | CH$_3$CH(O—PNCB) | H | CH$_3$ | H | O | S | a-Ph |
| 278 | b-CH$_3$ | CH$_3$CH(O—DPTBS) | H | CH$_3$ | H | O | S | a-Ph |
| 279 | b-CH$_3$ | CH$_3$CH(O—TPS) | H | CH$_3$ | H | O | S | a-Ph |
| 280 | b-CH$_3$ | CH$_3$CH(O—IPDMS) | H | CH$_3$ | H | O | S | a-Ph |
| 281 | b-CH$_3$ | CH$_3$CH$_2$CH(OH) | H | CH$_3$ | H | O | S | a-Ph |
| 282 | b-CH$_3$ | CH$_3$CH$_2$CH$_2$CH(OH) | H | CH$_3$ | H | O | S | a-Ph |
| 283 | b-CH$_3$ | (CH$_3$)$_2$CHCH(OH) | H | CH$_3$ | H | O | S | a-Ph |
| 284 | b-CH$_3$ | CH$_3$CH$_2$(CH$_3$)C(OH) | H | CH$_3$ | H | O | S | a-Ph |
| 285 | b-CH$_3$ | (CH$_3$)$_2$C(O—PNB) | H | CH$_3$ | H | O | S | a-Ph |
| 286 | b-CH$_3$ | CH$_3$CH$_2$CH(O—DPTBS) | H | CH$_3$ | H | O | S | a-Ph |
| 287 | a-CH$_3$ | CH$_3$CH(O—DMTBS) | PNBC | H | CH(CH$_3$)$_2$ | O | S | H |

TABLE III-continued

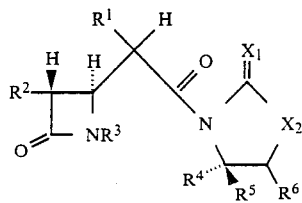

IIA

| Compound | R¹ | R² | R³ | R⁴ | R⁵ | X¹ | X² | R⁶ |
|---|---|---|---|---|---|---|---|---|
| 288 | a-CH₃ | CH₃CH(O—DMTBS) | PNBC | H | CH(CH₃)₂ | O | S | H |
| 289 | a-CH₃ | CH₃CH(O—DMTBS) | PNBC | H | CH(CH₃)₂ | O | S | H |
| 290 | b-CH₃CH₂ | CH₃CH(O—DMTBS) | DMTBS | PhCH₂ | H | O | S | H |
| 291 | b-CH₃CH₂ | CH₃CH(O—DMTBS) | DMTBS | PhCH₂ | H | O | S | H |
| 292 | b-CH₃CH₂ | CH₃CH(O—DMTBS) | DMTBS | PhCH₂ | H | O | S | H |
| 293 | a-CH(CH₃)₂ | CH₃CH(O—DMTBS) | Bz | H | CH₃ | O | S | b-Ph |
| 294 | a-CH(CH₃)₂ | CH₃CH(O—DMTBS) | Bz | H | CH₃ | O | S | b-Ph |
| 295 | a-CH(CH₃)₂ | CH₃CH(O—DMTBS) | Bz | H | CH₃ | O | S | b-Ph |
| 296 | b-OCH₃ | CH₃CH(O—DMTBS) | PNB | (CH₃)₂CHCH— | H | O | S | H |
| 297 | b-OCH₃ | CH₃CH(O—DMTBS) | PNB | (CH₃)₂CHCH— | H | O | S | H |
| 298 | b-OCH₃ | CH₃CH(O—DMTBS) | PNB | (CH₃)₂CHCH— | H | O | S | H |
| 299 | a-OCH₂CH₃ | CH₃CH(O—DMTBS) | PNB | H | CH₃CH₂(CH₃CH— | O | S | H |
| 300 | a-OCH₂CH₃ | CH₃CH(O—DMTBS) | PNB | H | CH₃CH₂(CH₃CH— | O | S | H |
| 301 | a-OCH₂CH₃ | CH₃CH(O—DMTBS) | PNB | H | CH₃CH₂(CH₃CH— | O | S | H |
| 302 | a-OCH₂CH₂CH₃ | CH₃CH(O—DMTBS) | PNB | H | Ph | O | S | H |
| 303 | a-OCH₂CH₂CH₃ | CH₃CH(O—DMTBS) | PNB | H | Ph | O | S | H |
| 304 | a-OCH₂CH₂CH₃ | CH₃CH(O—DMTBS) | PNB | H | Ph | O | S | H |
| 305 | a-CH₃CH₂ | CH₃CH(O—DMTBS) | PNB | H | CH₃ | O | S | H |
| 306 | a-CH₃CH₂ | CH₃CH(O—DMTBS) | PNB | H | CH₃ | O | S | H |
| 307 | a-CH₃CH₂ | CH₃CH(O—DMTBS) | PNB | H | CH₃ | O | S | H |
| 308 | a-OCH₃ | CH₃CH(O—DMTBS) | PNB | H | CH₃ | O | S | H |
| 309 | a-OCH₃ | CH₃CH(O—DMTBS) | PNB | H | CH₃ | O | S | H |
| 310 | b-CH₃ | HO—CH₂ | H | CH(CH₃)₂ | H | S | O | H |
| 311 | b-CH₃ | CH₃—CHOH | H | CH(CH₃)₂ | H | S | O | H |
| 312 | b-CH₃ | (CH₃)₂COH— | H | CH(CH₃)₂ | H | S | O | H |
| 313 | b-CH₃ | CH₃CH(O—DMTBS) | DMTBS | CH(CH₃)₂ | H | S | O | H |
| 314 | b-CH₃ | CH₃CH(O—TMS) | H | CH(CH₃)₂ | H | S | O | H |
| 315 | b-CH₃ | CH₃CH(O—Bz) | H | CH(CH₃)₂ | H | S | O | H |
| 316 | b-CH₃ | CH₃CH(O—PNB) | H | CH(CH₃)₂ | H | S | O | H |
| 317 | b-CH₃ | CH₃CH(O—PNBC) | H | CH(CH₃)₂ | H | S | O | H |
| 318 | b-CH₃ | CH₃CH₂CH(OH)— | H | CH(CH₃)₂ | H | S | O | H |
| 319 | b-CH₃ | CH₃CH₂CH₂CH(OH)— | H | CH(CH₃)₂ | H | S | O | H |
| 320 | b-CH₃ | (CH₃)₂CH—CH(OH) | H | CH(CH₃)₂ | H | S | O | H |
| 321 | b-CH₃ | CH₃CH₂C(CH₃)(OH) | H | CH(CH₃)₂ | H | S | O | H |
| 322 | b-CH₃ | HOCH₂ | H | PhCH₂ | H | S | O | H |
| 323 | b-CH₃ | CH₃CHF | TMS | PhCH₂ | H | S | O | H |
| 324 | b-CH₃ | (CH₃)₂COH | H | PhCH₂ | H | S | O | H |
| 325 | b-CH₃ | CH₃CH(O—DMTBS) | H | PhCH₂ | H | S | O | H |
| 326 | b-CH₃ | CH₃CH(O—TMS) | H | PhCH₂ | H | S | O | H |
| 327 | b-CH₃ | CH₃CH(O—Bz) | H | PhCH₂ | H | S | O | H |
| 328 | b-CH₃ | CH₃CH(O—PNB) | H | PhCH₂ | H | S | O | H |
| 329 | b-CH₃ | CH₃CH(O—PNBC) | H | PhCH₂ | H | S | O | H |
| 330 | b-CH₃ | CH₃CH(O—DPTBS) | H | PhCH₂ | H | S | O | H |
| 331 | b-CH₃ | CH₃CH(O—TPS) | H | PhCH₂ | H | S | O | H |
| 332 | b-CH₃ | CH₃CH(O—IPDMS) | H | PhCH₂ | H | S | O | H |
| 333 | b-CH₃ | CH₃CH₂CH(OH) | H | PhCH₂ | H | S | O | H |
| 334 | b-CH₃ | CH₃CH₂CH₂CH(OH) | H | PhCH₂ | H | S | O | H |
| 335 | b-CH₃ | (CH₃)₂CHCH(OH) | H | PhCH₂ | H | S | O | H |
| 336 | b-CH₃ | CH₃CH₂(CH₃)C(OH) | H | PhCH₂ | H | S | O | H |
| 337 | b-CH₃ | (CH₃)₂C(O—PNB) | H | PhCH₂ | H | S | O | H |
| 338 | b-CH₃ | CH₃CH₂CH(O—DPTBS) | H | PhCH₂ | H | S | O | H |
| 339 | b-CH₃ | HOCH₂ | H | (CH₃)₂CHCH₂ | H | S | O | H |
| 340 | b-CH₃ | FH₂CHOH | H | (CH₃)₂CHCH₂ | H | S | O | H |
| 341 | b-CH₃ | (CH₃)₂COH | H | (CH₃)₂CHCH₂ | H | S | O | H |
| 342 | b-CH₃ | CH₃CH(O—DMTBS) | H | (CH₃)₂CHCH₂ | H | S | O | H |
| 343 | b-CH₃ | CH₃CH(O—TMS) | H | (CH₃)₂CHCH₂ | H | S | O | H |
| 344 | b-CH₃ | CH₃CH(O—Bz) | H | (CH₃)₂CHCH₂ | H | S | O | H |
| 345 | b-CH₃ | CH₃CH(O—PNB) | H | (CH₃)₂CHCH₂ | H | S | O | H |
| 346 | b-CH₃ | CH₃CH(O—PNCB) | H | (CH₃)₂CHCH₂ | H | S | O | H |
| 347 | b-CH₃ | CH₃CH(O—DPTBS) | H | (CH₃)₂CHCH₂ | H | S | O | H |
| 348 | b-CH₃ | CH₃CH(O—TPS) | H | (CH₃)₂CHCH₂ | H | S | O | H |
| 349 | b-CH₃ | CH₃CH(O—IPDMS) | H | (CH₃)₂CHCH₂ | H | S | O | H |
| 350 | b-CH₃ | CH₃CH₂CH(OH) | H | (CH₃)₂CHCH₂ | H | S | O | H |
| 351 | b-CH₃ | CH₃CH₂CH₂CH(OH) | H | (CH₃)₂CHCH₂ | H | S | O | H |
| 352 | b-CH₃ | (CH₃)₂CHCH(OH) | H | (CH₃)₂CHCH₂ | H | S | O | H |
| 353 | b-CH₃ | CH₃CH₂(CH₃)C(OH) | H | (CH₃)₂CHCH₂ | H | S | O | H |
| 354 | b-CH₃ | (CH₃)₂C(O—PNB) | H | (CH₃)₂CHCH₂ | H | S | O | H |
| 355 | b-CH₃ | CH₃CH₂CH(O—DPTBS) | H | (CH₃)₂CHCH₂ | H | S | O | H |
| 356 | b-CH₃ | HOCH₂ | H | CH₃CH₂(CH₃)CH— | H | S | O | H |
| 357 | b-CH₃ | CH₃CHOH | H | CH₃CH₂(CH₃)CH— | H | S | O | H |

TABLE III-continued

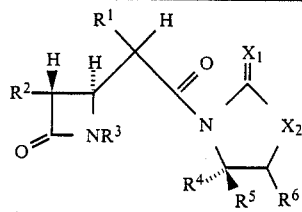

IIA

| Compound | R¹ | R² | R³ | R⁴ | R⁵ | X¹ | X² | R⁶ |
|---|---|---|---|---|---|---|---|---|
| 358 | b-CH₃ | (CH₃)₂COH | H | CH₃CH₂(CH₃)CH— | H | S | O | H |
| 359 | b-CH₃ | CH₃CH(O—DMTBS) | H | CH₃CH₂(CH₃)CH— | H | S | O | H |
| 360 | b-CH₃ | CH₃CH(O—TMS) | H | CH₃CH₂(CH₃)CH— | H | S | O | H |
| 361 | b-CH₃ | CH₃CH(O—Bz) | H | CH₃CH₂(CH₃)CH— | H | S | O | H |
| 362 | b-CH₃ | CH₃CH(O—PNB) | H | CH₃CH₂(CH₃)CH— | H | S | O | H |
| 363 | b-CH₃ | CH₃CH(O—PNCB) | H | CH₃CH₂(CH₃)CH— | H | S | O | H |
| 364 | b-CH₃ | CH₃CH(O—DPTBS) | H | CH₃CH₂(CH₃)CH— | H | S | O | H |
| 365 | b-CH₃ | CH₃CH(O—TPS) | H | CH₃CH₂(CH₃)CH— | H | S | O | H |
| 366 | b-CH₃ | CH₃CH(O—IPDMS) | H | CH₃CH₂(CH₃)CH— | H | S | O | H |
| 367 | b-CH₃ | CH₃CH₂CH(OH) | H | CH₃CH₂(CH₃)CH— | H | S | O | H |
| 368 | b-CH₃ | CH₃CH₂CH₂CH(OH) | H | CH₃CH₂(CH₃)CH— | H | S | O | H |
| 369 | b-CH₃ | (CH₃)₂CHCH(OH) | H | CH₃CH₂(CH₃)CH— | H | S | O | H |
| 370 | b-CH₃ | CH₃CH₂(CH₃)C(OH) | H | CH₃CH₂(CH₃)CH— | H | S | O | H |
| 371 | b-CH₃ | (CH₃)₂C(O—PNB) | H | CH₃CH₂(CH₃)CH— | H | S | O | H |
| 372 | b-CH₃ | CH₃CH₂CH(O—DPTBS) | H | CH₃CH₂(CH₃)CH— | H | S | O | H |
| 373 | b-CH₃ | HOCH₂ | H | CH₃ | H | S | O | a-Ph |
| 374 | b-CH₃ | CH₃CHOH | H | CH₃ | H | S | O | a-Ph |
| 375 | b-CH₃ | (CH₃)₂COH | H | CH₃ | H | S | O | a-Ph |
| 376 | b-CH₃ | CH₃CH(O—DMTBS) | H | CH₃ | H | S | O | a-Ph |
| 377 | b-CH₃ | CH₃CH(O—TMS) | H | CH₃ | H | S | O | a-Ph |
| 378 | b-CH₃ | CH₃CH(O—Bz) | H | CH₃ | H | S | O | a-Ph |
| 379 | b-CH₃ | CH₃CH(O—PNB) | H | CH₃ | H | S | O | a-Ph |
| 380 | b-CH₃ | CH₃CH(O—PNCB) | H | CH₃ | H | S | O | a-Ph |
| 381 | b-CH₃ | CH₃CH(O—DPTBS) | H | CH₃ | H | S | O | a-Ph |
| 382 | b-CH₃ | CH₃CH(O—TPS) | H | CH₃ | H | S | O | a-Ph |
| 383 | b-CH₃ | CH₃CH(O—IPDMS) | H | CH₃ | H | S | O | a-Ph |
| 384 | b-CH₃ | CH₃CH₂CH(OH) | H | CH₃ | H | S | O | a-Ph |
| 385 | b-CH₃ | CH₃CH₂CH₂CH(OH) | H | CH₃ | H | S | O | a-Ph |
| 386 | b-CH₃ | (CH₃)₂CHCH(OH) | H | CH₃ | H | S | O | a-Ph |
| 387 | b-CH₃ | CH₃CH₂(CH₃)C(OH) | H | CH₃ | H | S | O | a-Ph |
| 388 | b-CH₃ | (CH₃)₂C(O—PNB) | H | CH₃ | H | S | O | a-Ph |
| 389 | b-CH₃ | CH₃CH₂CH(O—DPTBS) | H | CH₃ | H | S | O | a-Ph |
| 390 | a-CH₃ | CH₃CH(O—DMTBS) | PNBC | H | CH(CH₃)₂ | S | O | H |
| 391 | a-CH₃ | CH₃CH(O—DMTBS) | PNBC | H | CH(CH₃)₂ | S | O | H |
| 392 | a-CH₃ | CH₃CH(O—DMTBS) | PNBC | H | CH(CH₃)₂ | S | O | H |
| 393 | b-CH₃CH₂ | CH₃CH(O—DMTBS) | DMTBS | PhCH₂ | H | S | O | H |
| 394 | b-CH₃CH₂ | CH₃CH(O—DMTBS) | DMTBS | PhCH₂ | H | S | O | H |
| 395 | b-CH₃CH₂ | CH₃CH(O—DMTBS) | DMTBS | PhCH₂ | H | S | O | H |
| 396 | a-CH(CH₃)₂ | CH₃CH(O—DMTBS) | Bz | H | CH₃ | S | O | b-Ph |
| 397 | a-CH(CH₃)₂ | CH₃CH(O—DMTBS) | Bz | H | CH₃ | S | O | b-Ph |
| 398 | a-CH(CH₃)₂ | CH₃CH(O—DMTBS) | Bz | H | CH₃ | S | O | b-Ph |
| 399 | b-OCH₃ | CH₃CH(O—DMTBS) | PNB | (CH₃)₂CHCH— | H | S | O | H |
| 400 | b-OCH₃ | CH₃CH(O—DMTBS) | PNB | (CH₃)₂CHCH— | H | S | O | H |
| 401 | b-OCH₃ | CH₃CH(O—DMTBS) | PNB | (CH₃)₂CHCH— | H | S | O | H |
| 402 | a-OCH₂CH₃ | CH₃CH(O—DMTBS) | PNB | H | CH₃CH₂(CH₃CH— | S | O | H |
| 403 | a-OCH₂CH₃ | CH₃CH(O—DMTBS) | PNB | H | CH₃CH₂(CH₃CH— | S | O | H |
| 404 | a-OCH₂CH₃ | CH₃CH(O—DMTBS) | PNB | H | CH₃CH₂(CH₃CH— | S | O | H |
| 405 | a-OCH₂CH₂CH₃ | CH₃CH(O—DMTBS) | PNB | H | Ph | S | O | H |
| 406 | a-OCH₂CH₂CH₃ | CH₃CH(O—DMTBS) | PNB | H | Ph | S | O | H |
| 407 | a-OCH₂CH₂CH₃ | CH₃CH(O—DMTBS) | PNB | H | Ph | S | O | H |
| 408 | a-CH₃CH₂ | CH₃CH(O—DMTBS) | PNB | H | CH₃ | S | O | H |
| 409 | a-CH₃CH₂ | CH₃CH(O—DMTBS) | PNB | H | CH₃ | S | O | H |
| 410 | a-CH₃CH₂ | CH₃CH(O—DMTBS) | PNB | H | CH₃ | S | O | H |
| 411 | a-OCH₃ | CH₃CH(O—DMTBS) | PNB | H | CH₃ | S | O | H |
| 412 | a-OCH₃ | CH₃CH(O—DMTBS) | PNB | H | CH₃ | S | O | H |

Abbreviations used in the Table are:
DMTBS = dimethyl-t-butylsilyl
TMS = trimethylsilyl
Bz = benzyl
PNB = p-nitrobenzyl
PNBC = p-nitrobenzylcarbonyl(oxy?)
Ph = phenyl
a-CH₃ = alpha-CH₃
b-CH₃ = beta-CH₃
TPS = triphenylsilyl
IPBMS = isopropyldimethylsilyl The above recited structures and formulas for Structure II are illustrative and not meant to be limiting and other combinations of R¹, R², R³, R⁴, R⁵ and R⁶ resulting in other species of Structure II in light of this disclosure, not specifically recited herein, are deemed to be included within the scope of this invention.

Preferred compounds of structure II include the following compounds:
where
$R^1$ is beta-methyl;
$R^2$ is protected 1-hydroxyethyl; preferably protected with DMTBS;
$R^3$ is hydrogen;
$R^4$ is isopropyl, isobutyl, sec-butyl, benzyl or methyl;
$R^5$ is hydrogen;
$R^6$ is hydrogen, and where $R^4$ is methyl, $R^6$ is phenyl.
where $X^1$ and $X^2$ are both O; and
where $X^1$ and $X^2$ are both S.

The hydrolysis of Structures II to Structure V labeled Step (b), in the above-illustrated process can be carried out according to conventional procedure in the overall process and can also be individually carried out by the novel modified process claimed herein of utilizing a basic agent, preferably lithium hydroxide, as the sole basic hydrolyzing agent.

The reference of Evans et al. *JACS*, 1982, Vol. 104, (6) pp. 1737–1739 hereinabove describes a general procedure for utilizing a benzyl alcohol-lithium benzolate mixture in order to achieve hydrolysis accompanied by very little racemization leading to benzyl esters. It has been discovered that lithium hydroxide by itself is a very suitable hydrolysis agent, in the absence of benzyl alcohol, for directly producing the acid without significant attendant racemization. It has also been found that sodium hydroxide, and potassium hydroxide are also effective hydrolysis agents for the beta isomer, if the base is sufficiently solubilized during the reaction, for example, by the addition of crown ether agents, and the like, but that use of NaOH leads to degradation of the alpha epimer.

In general the hydrolysis reaction conditions include the use of a polar solvent, in admixture with $H_2O$, having suitable solubility for LiOH and Structure II. Representative examples include $THF-H_2O$, and $Et_2O-H_2O$ and $DMF-H_2O$. Preferred is $THF-H_2O$.

The concentration of structure II and lithium hydroxide reagents in the hydrolysis medium are in a range of 0.5 to 1.5 molar and preferably 1.0 to 1.2 molar.

The temperature of the hydrolysis step is normally carried out in the reaction range of 0° to 25° C. and preferably in a temperature range of 20° to 25° C.

The pressure that the process is conducted under is generally at atmospheric.

Time for conducting Step (b) is normally in a range of about 3 to 5 hours thereby achieving hydrolysis yields in the range of 90 to 95%.

Workup of the product carboxylic acid V including isolation and purification involve conventional techniques such as acid-base extraction and crystallization to yield the carboxylic acids.

In a preferred embodiment, the process also includes the step of recovering an oxazolidinone of the formula:

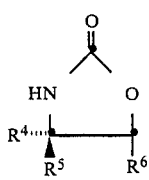

wherein $R^4$, $R^5$ and $R^6$ are described herein, which is formed as a byproduct from the hydrolysis Step (b), and converting to the following N-acyl compound by reaction with $R^1-CH_2COX$; wherein $R^1$ is described herein, and X is halo, eg. Br, Cl;

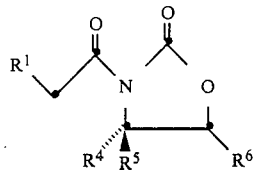

and reacting said compound with an enolating agent containing $R^8$ functionality described herein, to yield:

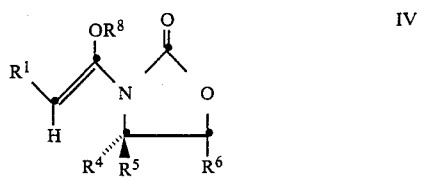

which is recycled for use to Step (a).

In a specific embodiment, following the hydrolysis step, the water-soluble lithium salt of the beta-methyl azetidinone acid V is recovered by acidification of the aqueous layer, following organic solvent extraction of the resulting hydrolysis mixture.

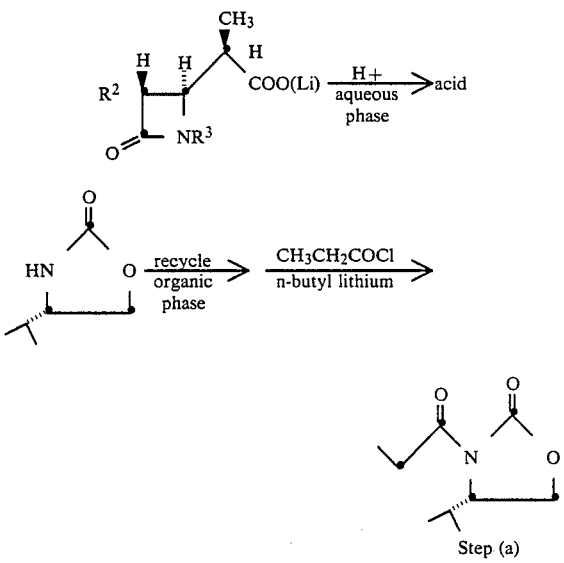

Step (a)

The resulting organic phase, containing the organic extracts, for example methylene chloride, also contains recovered chiral oxazolidone which remains stable and retains its original chirality throughout the hydrolysis process. Advantage is taken of this fact by recycling the organic phase back to Step (a) in which the organic layer is dried, concentrated and then treated with an acyl chloride, e.g. propionyl chloride and base, e.g. n-butyllithium, to regenerate the starting N-acyl oxazolidinone in Step (a).

Suitable apparatus for carrying out this process is conventional and will be obvious to one skilled in the art.

The resulting alkyl carboxylic acids are presented in the following Table IV of representative examples:

TABLE IV

V

| Compound | R¹ | R² | R³ |
|---|---|---|---|
| 1 | b-CH₃ | HOCH₂ | H |
| 2 | b-CH₃ | CH₃CHOH | H |
| 3 | b-CH₃ | (CH₃)₂COH | H |
| 4 | b-CH₃ | CH₃CH(O—DMTBS) | H |
| 5 | b-CH₃ | CH₃CH(O—TMS) | TMS |
| 6 | b-CH₃ | CH₃CH(O—Bz) | H |
| 7 | b-CH₃ | CH₂CH(O—PNB) | H |
| 8 | b-CH₃ | CH₃CH(O—PNBC) | H |
| 9 | b-CH₃ | CH₃CH(O—DPTBS) | DPTBS |
| 10 | b-CH₃ | CH₂CH(O—TPS) | TPS |
| 11 | b-CH₃ | CH₃CH(O—IPDMS) | IPDMS |
| 12 | b-CH₃ | CH₃CH₂CH(OH) | H |
| 13 | b-CH₃ | CH₃CH₂CH₂CH(OH) | H |
| 14 | b-CH₃ | (CH₃)₂CHCH(OH) | H |
| 15 | b-CH₃ | CH₃CH₂(CH₃)C(OH) | H |
| 16 | b-CH₃ | (CH₃)₂C(O—PNB) | H |
| 17 | b-CH₃ | CH₃CH₂CH(O—DPTBS) | DPTBS |
| 18 | b-OCH₃ | HOCH₂ | H |
| 19 | b-OCH₃ | CH₃CHOH | H |
| 20 | b-OCH₃ | (CH₃)₂OH | H |
| 21 | b-OCH₃ | CH₃CH(O—DMTBS) | DMTBS |
| 22 | b-OCH₃ | CH₃CH(O—TMS) | TMS |
| 23 | b-OCH₃ | CH₃CH(O—Bz) | H |
| 24 | b-OCH₃ | CH₃CH(O—PNB) | H |
| 25 | b-OCH₃ | CH₃CH(O—PNCB) | H |
| 26 | b-OCH₃ | CH₃CH(O—DPTBS) | H |
| 27 | b-OCH₃ | CH₃CH(O—TPS) | H |
| 28 | b-OCH₃ | CH₃CH(O—IPDMS) | H |
| 29 | b-OCH₃ | CH₃CH₂CH(OH) | H |
| 30 | b-OCH₃ | CH₃CH₂CH₂CH(OH) | H |
| 31 | b-OCH₃ | (CH₃)₂CHCH(OH) | H |
| 32 | b-OCH₃ | CH₃CH₂(CH₂)C(OH) | H |
| 33 | b-OCH₃ | (CH₃)₂C(P—PNB) | H |
| 34 | b-OCH₃ | CH₃CH₂CH(O—DPTBS) | H |
| 35 | a-CH₃ | CH₃CH(O—DMTBS) | DMTBS |
| 36 | a-CH₃ | CH₃CH(O—DMTBS) | H |
| 37 | a-CH₃CH₂ | CH₃CH(O—DMTBS) | H |
| 38 | a-OCH₃ | CH₃CHOH | PNBC |
| 39 | a-OCH₂CH₃ | CH₃CHOH | PNBC |
| 40 | a-OCH₂CH₃ | CH₃CHOH | H |
| 41 | b-CH₃CH₂ | CH₃CH(O—IPDMS) | H |
| 42 | b-CH₃CH₂ | CH₃CH(O—IPDMS) | PNBC |
| 43 | b-CH₃CH₂ | HOCH₂ | PNBC |
| 44 | b-O—CH(CH₃)₂ | CH₃CH(O—TMS) | H |
| 45 | b-O—CH(CH₃)₂ | CH₃CH(O—TMS) | PNBC |
| 46 | b-OCH₂CH₂CH₃ | CH₃CH(O—TMS) | PNBC |
| 47 | b-CH(CH₃)₂ | CH₃CH(O—PNBC) | Bz |
| 48 | b-CH(CH₃)₂ | CH₃CH(O—PNBC) | H |
| 49 | b-CH₂CH₂CH₂CH₃ | CH₃CH(O—PNBC) | H |
| 50 | b-CH₂CH₂CH₂CH₃ | CH₃CH(O—PNBC) | PNBC |

The above abbreviations are the same as previously used and described herein.

The above-recited structures and formulas for Structure II are illustrative and not meant to be limiting and other combinations of R¹, R² and R³ not specifically recited herein, but obvious to one skilled in the art from this disclosure, are deemed to be incorporated herein.

Preferred product alkyl carboxylic acids produced by the subject process include the following compounds:

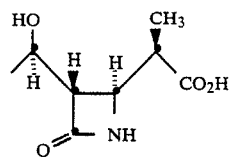

-continued

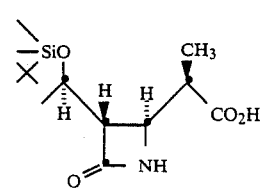

The following examples are illustrative of the best mode of carrying out the instant invention as contemplated by us and should not be construed to be limitations on the spirit or scope of the instant invention.

For convenience, the following abbreviations generally known in the art are used in the Examples, as tabulated below, with their respective meanings:

TABLE V

| Abbreviation | Meaning |
| --- | --- |
| RT | room temperature |
| NMR | nuclear magnetic resonance |
| MHz | megahertz |
| THF | tetrahydrofuran |
| n-BuLi | n-butyllithium |
| g | grams |
| mmole | millimole |
| equiv. | equivalent |
| bp | boiling point |
| mp | melting point |
| DMF | dimethylformamide |
| Et | ethyl |
| Et$_2$O | diethylether |
| X | times |
| TMS, Me$_3$Si | trimethylsilyl |
| n-Bu$_2$BOTf | di-n-butylboryltriflate |
| OAc | acetate |
| HPLC | high pressure liquid chromatography |
| TLC | thin layer chromatography |
| IPA | isopropanol |
| EtOAc | ethylacetate |
| OX | oxazolidinone |
| LDA | lithium diisopropylamide |
| OTf | triflate |

PREPARATION OF STARTING MATERIALS

1. Preparation of (4S)-4-(1-Methylethyl)-2-Oxazolidinone (A)

Reaction:

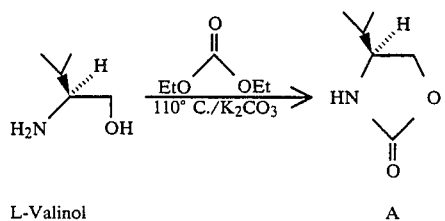

L-Valinol                A

Procedure:

Into a dry 100 mg single-necked flask equipped with magnetic stirrer and a short path distillation head is placed 12.4978 g (96% pure, Aldrich, 0.1162 mmole) of (2S)-2-amino-3-methyl butanol (L-Valinol), 17 ml of diethylcarbonate (bp 126°–8° C., d. 0.975) and about 1 g. of anh. K$_2$CO$_3$. The reaction mixture is heated in an oil bath pre-equilibrated to 110° C. Heating is continued until ethanol distillation ceases (ca. 14 h). Upon cooling to RT (room temp.), the contents of the flask are solidified. The reaction product is dissolved in CH$_2$Cl$_2$, filtered through a Celite pad, and concentrated in vacuo to give a colorless solid. Recrystallization from diethyl ether affords 9.22 g (61.4%) of the oxazolidone A as a white crystalline solid, mp 71°–2° C. Proton NMR (200 MHz) in CDCl$_3$ shows:

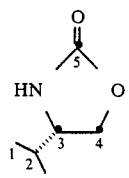

6.15 (broad s, 1H, N$\underline{H}$); 4.44 (t, J=8.6 Hz, C$_5$-$\underline{H}$); 4.09 (ddd, J=8.6 Hz, J=6.2 Hz, C$_5$-$\underline{H}$); 3.59 (q, 1H, J=7.0 Hz, C$_4$-$\underline{H}$); 1.71 (m, 1H, C$_2$-$\underline{H}$); 0.94, 0.88 (d, 6H, J=8.49 Hz, J=7.65 Hz, C$_1$-$\underline{H}$).

2. Preparation of (4S)-3-(1-Oxopropyl)-4-(1-Methylethyl)-2-oxazolidinone (B)

Reaction:

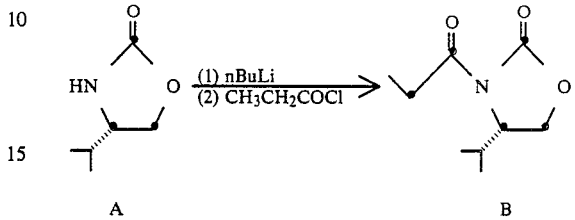

Procedure:

To a cooled solution (−78° C.) of 1.5910 g (12.316 mmole of (+)-(4S)-3-(1-oxopropyl)-4-(1-methylethyl)-2-oxoazolidinone (A) in 20 ml of THF under N$_2$ atmosphere is added 5.80 ml of 2.32M n-BuLi in hexane (13.55 mmole, 1.1 equiv.) to form the conjugate base. The milky slurry is stirred for 1 hour before 1.11 ml (1.1852 g, 12.81 mmoles, 1.04 equiv., mwt 92.53, bp 77°–9° C., d 1.065) of propionyl chloride is added in one portion. The slurry dissolves instantly to a clear orange solution. After stirring an additional 15 min. at −78° C., the reaction is quenched with 20 ml sat. NH$_4$Cl, and the THF is removed in vacuo at RT (room temp). The resultant concentrate is taken up in ether and extracted successively with aq. NaHCO$_3$, water, brine and dried over anh. Na$_2$SO$_4$. Evaporation of the solvent followed by flash chromatography affords 1.82 g (80%) of purified product B as a viscous yellow oil. Proton NMR (200 MHz) in CDCl$_3$ shows:

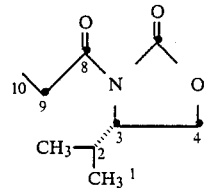

4.41 (d of t, 1H, J=7.6 Hz, J=3.6 Hz, C$_3$-$\underline{H}$); 4.22 (m, 2H, $^2$J=5.4 Hz, C$_4$-$\underline{H}$); 2.92 (q of d, 2H, J=7.7 Hz, J=4.0 Hz, C$_9$-$\underline{H}$); 2.35 (m, 1H, J=7.0 Hz, J=3.9 Hz, C$_2$-$\underline{H}$); 1.14 (t, 3H, J=7.7 Hz, C$_{10}$-$\underline{H}$); 0.89, 0.85 (d, 6H, J=7.0 Hz, C$_1$-$\underline{H}$).

Anal. for C$_9$H$_{15}$NO$_3$: Calc'd: C, 58.36; H, 8.18; N, 7.56; Found: C, 60.15; H, 8.40; N, 6.80.

3. Preparation of Silyl Protected Hydroxy Azetidinone-4-Acetate (1)

Reaction:

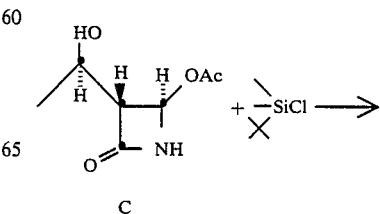

C

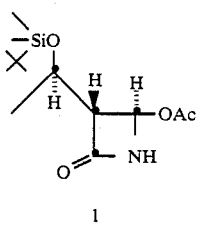

1

To a solution of the unprotected acetoxy compound C in 20 ml of sieve-dried DMF (dimethylformamide) in a 100 ml 1-neck r.b. (round bottom) flask at 5°–10° C. is added a solution of 1.1 eq. of t-BDMSCl (t-butyl-dimethylchlorosilane) in 10 ml DMF followed by 1.1 eq. of imidazole. The resulting solution is partitioned between 300 ml H$_2$O and 100 ml Et$_2$O. The aqueous portion is extracted twice more with 100 ml Et$_2$O, and the ether extracts, combined and dried (Na$_2$SO$_4$), are filtered through a pad of 60-200 mesh silica gel and washed 3x with Et$_2$O (product moves at solvent front on Et$_2$O). The ether layer is concentrated and dried to give 2.43 g (85%) 1. Proton NMR shows:

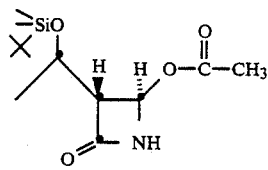

(250 MHz, CDCl$_3$) 6.45 (broad s, 1H, N-H); 5.82 (d, 1H, J=1.1 Hz, C$_4$-H); 4.21 (d of q, 1H, J=6.4 Hz, J=3.4 Hz, C$_5$-H); 3.17 (d of d, 1H, J=3.4, J=1.1 Hz, C$_3$-H); 2.09 (s, 3H, —OCOCH$_3$); 1.24 (d, 3H, J=6.4 Hz, C$_6$-H); 0.85 (s, 9H, tBuMe$_2$Si); 0.05, 0.03 (s, 6H, tBuMe$_2$Si).

EXAMPLE 1

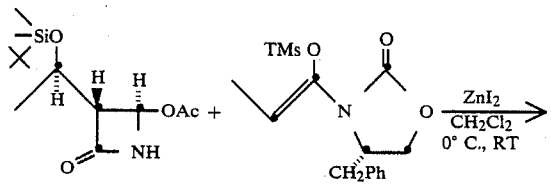

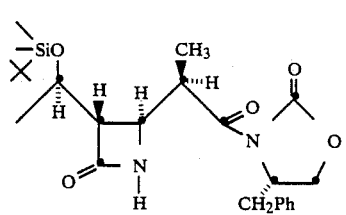

+ α-CH$_3$ isomer 5

A solution of the trimethylsilyl (TMS) enol ether 3 (153 mg, 0.50 mmol), prepared by reacting B and trimethylchlorosilane (in THF in the presence of lithium diisopropylamide at −78° C. and warmed to room temperature), and the 4-acetoxyazetidinone 1 (72 mg, 0.25 mmol) in 1.5 ml of dry CH$_2$Cl$_2$ is added via syringe to a rapidly stirring suspension of anhydrous zinc iodide (100 mg) in 2.5 ml of dry CH$_2$Cl$_2$ at 0° C. The ice bath is removed after 5 minutes and the mixture is allowed to stir at RT (room temperature) for 3 hours. During this time all materials dissolve into solution. The reaction mixture is diluted with ether (50 ml), washed with sat. aq. NaHCO$_3$ solution, water and brine, and dried over MgSO$_4$. Removal of solvents in vacuo gives a white foam which is chromatographed with ether on two 1000 micron silica gel GF plates. Two major bands are isolated and structural assignments are made on the basis of their TLC ether R$_f$ values as indicated below; and by analogy to the corresponding alpha- and beta-methyl azetidinone propionic esters described in Table VII.

| 1. | R$_f$ = 0.72 | 82.0 mg = β | isomer 3 - | 73% |
|---|---|---|---|---|
| 2. | R$_f$ = 0.44 | 22.5 mg = α | isomer 4 - | 20% |
|  |  | 104.5 mg |  | 93% |

TABLE VI

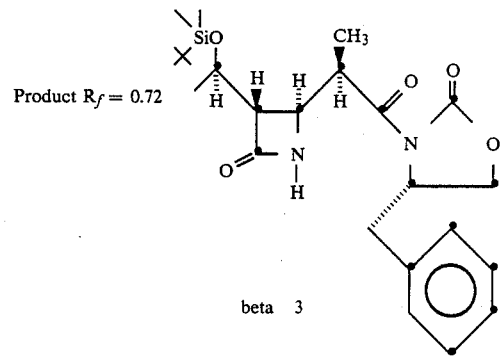

Product R$_f$ = 0.72 beta 3

200 MHz = CDCl$_3$

| | #Protons | Multiplicity | Coupling | Interpretative |
|---|---|---|---|---|
| 0.08 | 6 | s | | Si(CH$_3$)$_2$ |
| 0.88 | 9 | s | | SitBu |
| 1.23 | 3 | d | | CH$_3$CH— |
| 1.25 | 3 | d | | CH$_3$CH—H |
| 2.69 | 1 | dd | J = 13, 10 | φCH— |
| 3.08 | 1 | dd | J = 4.3, 2.1 | H6*H |
| 3.32 | 1 | dd | J = 13, 3.5 | φCH— |
| 3.98 | 1 | dd | J = 4.2, 2.1 | H5* |
| 4.1–4.3 | 4 | m | | H8*, H1*, CH$_2$O |
| 4.68 | 1 | dddd | | φCH$_2$CH— |
| 6.13 | 1 | br.s | | —NH |
| 7.2–7.4 | 5 | m | | aromatic |

*bicyclic numbering; i.e.

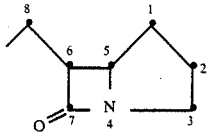

TABLE VII

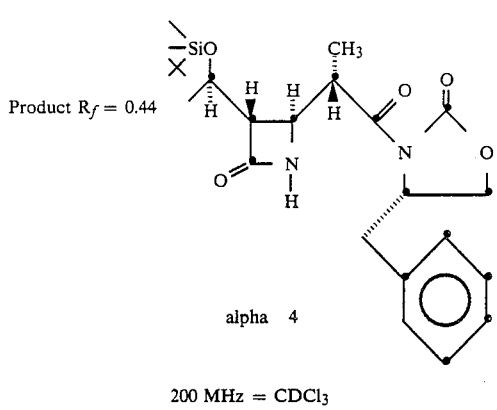

Product R$_f$ = 0.44 alpha 4

200 MHz = CDCl$_3$

| #Protons | Multiplicity | Coupling | Interpretative |
|---|---|---|---|
| 0.09 | 6 | 2 singlets | Si(C$\underline{H}$$_3$)$_2$ |
| 0.90 | 9 | s | Sit$\underline{Bu}$ |
| 1.27 | 3 | d | CH$_3$CH— |
| 1.35 | 3 | d | CH$_3$CH— |
| 2.83 | 1 | dd | J = 13, 9.5 | φCH— (H) |
| 2.85 | 1 | dd | J = 5.2, 2.2 | H6* |
| 3.25 | 1 | dd | J = 13, 3.5 | φCH— (H) |
| 3.94 | 1 | dd | J = 10, 2.2 | H5* |
| 4.1–4.4 | 4 | m | | H8*, H1*, C$\underline{H}$$_2$O |
| 4.73 | 1 | dddd | | φCH$_2$C$\underline{H}$— |
| 6.02 | 1 | br.s | | —N$\underline{H}$ |
| 7.2–7.4 | 5 | m | | aromatic |

Note:
Assignments based on comparison to:

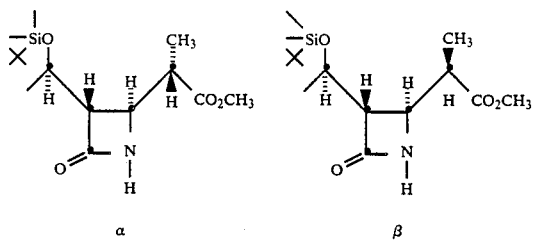

α          β

EXAMPLE 2

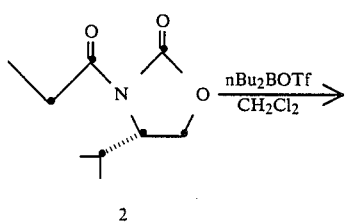

2

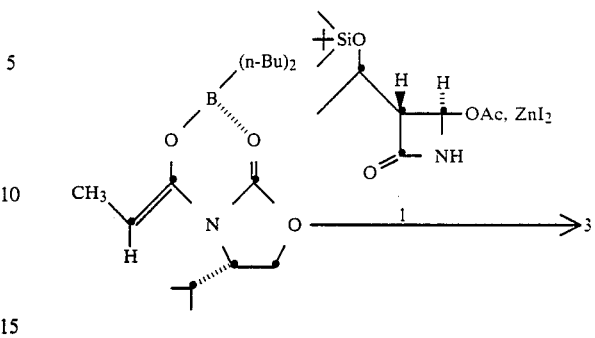

Into a dry, 2-necked flask equipped with a magnetic spinbar is placed 0.2947 g. (1.591 mmole) of (4S)-3-(1-oxopropyl)-4-(1-methylethyl)-2-oxazolidinone (2). The flask is flushed with N$_2$ and sealed with a rubber septum. Methylene chloride (3 mL) is added, and the solution cooled to −78° C. Di-n-butylboryl trifluoromethanesulfonate (1.75 mL, 1.750 mmole, 1.10 equiv., Aldrich) is added, followed immediately by 0.34 mL (0.2469 g., 1.20 equiv.) of diisopropylethylamine (Aldrich). The light yellow solution is stirred at −78° C. for 10 minutes and then 1 hour at 0° C. The solution is then cooled back to −78° C. and 1.446 mmole (0.4158 g) of the acetoxy compound 1 is added in one portion followed by 0.6103 (1.912 mmol) ZnI$_2$ (Ventron). Since ZnI$_2$ seems to be insoluble in CH$_2$Cl$_2$; 3.0 mL of THF is added to improve solubility. The reaction is stirred at −78° C. for 1 hour and slowly warmed up to room temperature overnight. To the reaction mixture at 0° C. is added 1.0 ml of pH 7 phosphate buffer to quench the reaction. Methanol (5 mL) is added then followed by 1.0 mL of 30% aqueous hydrogen peroxide and the mixture is stirred at 0° C. for 1 hour. The mixture is transferred to a separating funnel containing aq. NaHCO$_3$ and extracted with CH$_2$Cl$_2$ (3×20 mL). After drying the combined organic extracts over anh. MgSO$_4$ and evaporation of solvent in vacuo, the crude product is obtained as a yellow oil. Column chromatography using CH$_2$Cl$_2$ or silica gel affords the same composition of crude product, in which starting material is removed. This is confirmed by liquid chromatography (HPLC) and thin layer chromatography (TLC). Preparative TLC on 1500 microns silica gel using ether elution shows a major new spot which by 1H-NMR-(200 MHz) exhibits a spectrum identical to the beta-methyl isomer of Example 1. A rerun of the same procedure produces a crude mixture which by HPLC analysis using 3% IPA/Hexanes solvent, 2.0 ml/min. flow rate, normal phase procedure on an Altex column, shows a 91/9 β/α ratio which was confirmed by 250 MHz NMR. Purification of the crude using flash chromatography employing 250 ml CH$_2$Cl$_2$ followed by 50/50 EtOAc/Hexanes, affords 85.0 mg β isomer + 11.4 mg α isomer, representing an overall yield of 16% and a β/α ratio of 9/1.

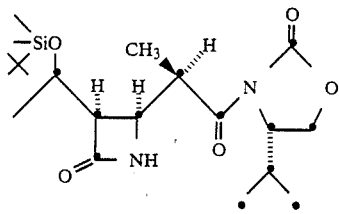

β-Me isomer

¹H-NMR (250 MHz, CDCl₃); 6.10 (broad s, 1H, N-H); 4.45 (d of t, 1H, J=7.6 Hz, J=3.4 Hz, C₃'-H); 4.24 (m, 4H, C₇-H, C₅-H, C₄'-H); 3.93 (d of d, 1H, J=4.1 Hz, J=2.2 Hz, C₄-H); 3.03 (d of d, 1H, J=2.9 Hz, J=2.2 Hz, C₃-H); 2.33 (m, 1H, C₂'-H); 1.22, 1.18 (d, 6H, J=7.0 Hz, J=6.3 Hz, C₅-CH₃, C₈-H); 0.87, 0.83 (d, 6H, J=7.1 Hz, J=6.3 Hz, C₁'-H); 0.82 (s, 9H, tBuMe₂Si); 0.03, 0.01 (d, 6H, tBuMe₂Si).

Anal. for C₂₀H₃₆N₂O₅Si: Calc'd: C, 58.22; H, 8.81; N, 6.79; Found: C, 58.49; H, 8.78; N, 6.58.

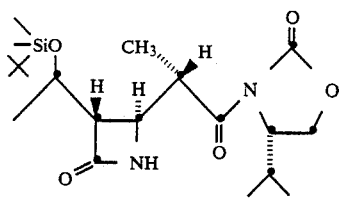

α-Me isomer

¹H-NMR (250 MHz, CDCl₃); 6.00 (broad s, 1H, N-H); 4.48 (d of t, 1H, J=7.4 Hz, J=3.4 Hz, C₃'-H); 4.31 (m, 3H, C₇-H, C₄'-H); 3.86 (d of d, 1H, J=9.8 Hz, J=2.0 Hz, C₄-H); 3.68 (d of q, 1H, J=9.7 Hz, J=7.0 Hz, C₅-H); 2.82 (d of d, 1H, J=5.4 Hz, J=1.7 Hz, C₃-H); 2.33 (m, 1H, C₂'-H); 1.31, 1.25 (d, 6H, J=7.0 Hz, J=6.3 Hz, C₅-CH₃, C₈-H); 0.87, 0.83 (d, 6H, J=7.1 Hz, J=6.3 Hz, C₁'-H); 0.82 (s, 9H, tBuMe₂Si); 0.03, 0.01 (s, 6H, tBuMe₂Si).

EXAMPLE 3

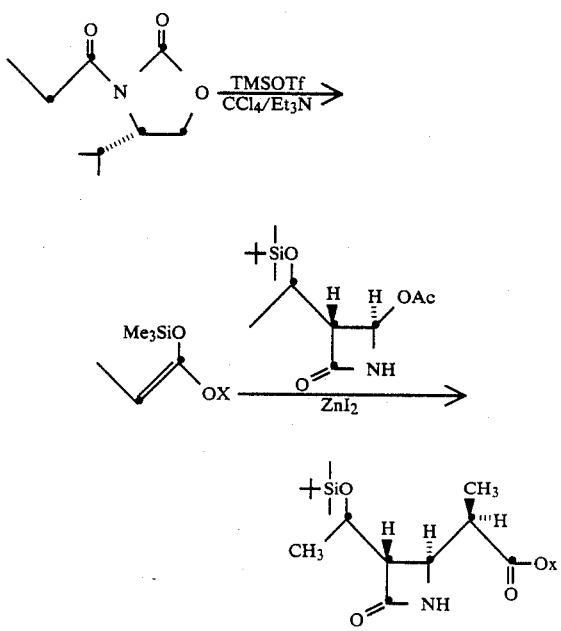

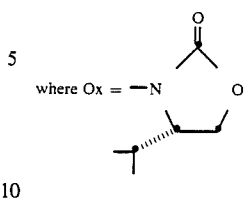

where Ox =

Into a dry, 2-necked flask equipped with a magnetic stirrer is weighed 197.2 mg (1.065 mmole) of the (4S)-3-(1-oxopropyl)-4-(1-methylethyl)-2-oxazolidinone. The flask is flushed with N₂ and sealed with a rubber septum. Carbon tetrachloride (5.0 ml) is added. Trimethylsilyltrifluoromethane sulfonate (0.31 ml, 0.3550 g, 1.600 mmole, Aldrich) is added, followed immediately by 0.30 ml (0.2160 g, 2.130 mmole, Aldrich) of triethylamine. The reaction mixture is stirred at room temperature for 1 hour. Two phases are observed. The reaction mixture is cooled to 0° C. and 10 ml of sat. NaHCO₃ is added. The organic layer is separated and the aqueous layer back extracted with 2×10 ml CH₂Cl₂. The combined organic layers are dried over MgSO₄. Evaporation of the solvent in vacuo affords 0.2452 g of crude material. A sample of 2.9 mg is used for ¹H-NMR-250 MHz enol ether assay which is fully described in Example 8. Enol ether ratio Z/E is 88:12 based on the ratio of the vinyl proton. Also starting material is observed. The enol ether is dissolved in (3 ml) methylene chloride and cooled to −78° C. The acetoxy azetidinone (0.311 mmol, 89.4 mg) is added followed by addition of 97.2 mg, (0.305 mmol) ZnI₂. The reaction mixture is stirred at −78° C. and slowly warmed up to room temperature overnight. The mixture is transferred to a separatory funnel containing 25 ml of sat. aqueous NaHCO₃ and extracted with (2×15 ml) CH₂Cl₂. After drying the combined organic layers over MgSO₄ and evaporation of the solvent in vacuo NMR and HPLC assay are performed. HPLC assay employing 30% IPA/Hexanes solvent, 2.0 ml/min. flow rate, after normal phase procedure, the column affords a β/α ratio of 74/26. The retention time of the β isomer is 21.6 min, and that of the α isomer, 26.8 min under these conditions. A ¹H-NMR-(250 MHz)-spectra of the crude exhibits a β/α ratio of 73/27 based on H-4 proton on the β-lactam. The crude product is purified by flash column chromatography. A 5″ diameter column packed with silica and using CH₂Cl₂ as the solvent, is eluted with 250 ml of CH₂CL₂ followed by 50% EtOAc.

Fractions 15–20 yield 74.1 mg of pure (250 MHz) β-isomer whose proton NMR spectrum is identical to that produced in Example 2;

Fractions 22–25, yield 36.3 mg of pure α-isomer, whose proton NMR (250 MHz) spectra is identical to that of Example 2.

The total isolated yield is 110.4 mg (86.0%) of combined β+α isomers.

EXAMPLE 4

Reaction:

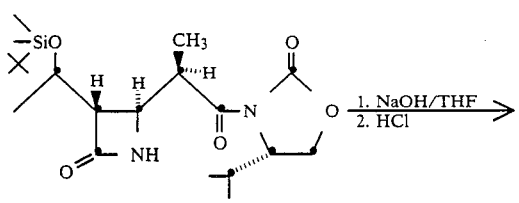

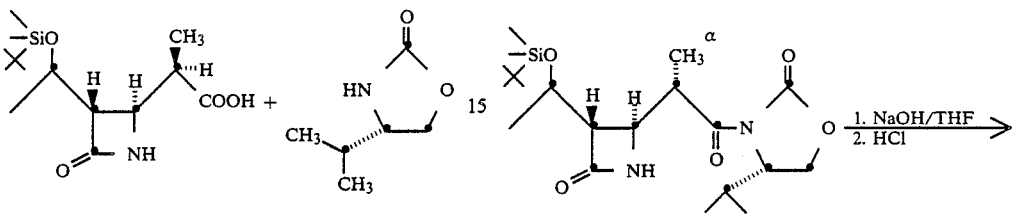

Seventy (70.0) mg (0.169 mmole) of the beta-methyl epimer from Example 3, is added at room temperature to 1 ml of 0.5N NaOH in (3 eq.) 1 ml of THF. The reaction is refluxed for 18 hours. The THF is removed and the residue dissolved in a small amount of water. The aqueous layer is extracted with $CH_2Cl_2$ (2×10 ml). The aqueous layer is acidified with HCl to pH 4 and the organic layer is back extracted with $CH_2Cl_2$/EtOAc. Proton NMR (250 MHz) analysis of the basic organic layer shows the following mixture having the proportionate molar ratios:

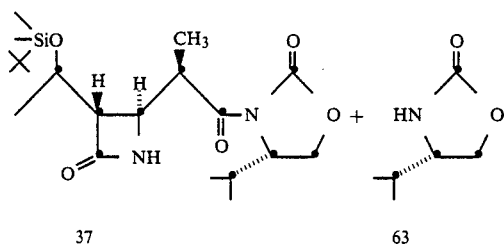

37                63

Proton NMR (250 MHz) analysis of the aqueous acid layer shows only the final beta epimer acid.

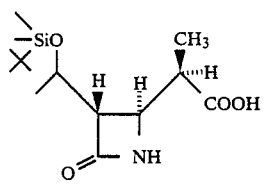

The calculated yield based on NMR data is 94%. The proton NMR shows:

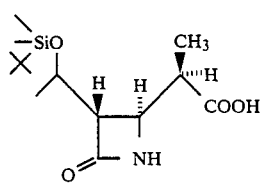

(250 MHz, $CDCl_3$) 6.26 (broad s, 1H NH); 4.19 (q of d, 1H, J=6.2 Hz, J=4.5 Hz, $C_7$-$\underline{H}$); 3.93 (d of d, 1H, J=5.0 Hz, J=2.2 Hz, $C_4$-$\underline{H}$); 3.01 (d of d, 1H, J=4.3 Hz, J=2.2 Hz, $C_3$-$\underline{H}$); 2.73 (q of d, 1H, J=7.0 Hz, J=5.0 Hz, $C_5$-$\underline{H}$); 1.26 (d, 3H, J=7.0 Hz, $C_5$-$CH_3$); 1.18 (d, 3H, J=6.2 Hz, $C_8$-$\underline{H}$); 0.86 (s, 9H, $tBuMe_2Si$); 0.06, 0.05 (s, 6H, $tBuMe_2Si$).

Calc'd for $C_{14}H_{27}NO_4Si$: Anal. C, 55.77; H, 9.04; N, 4.61 Found: C, 54.66; H, 8.90; N, 4.43.

EXAMPLE 5

Reaction:

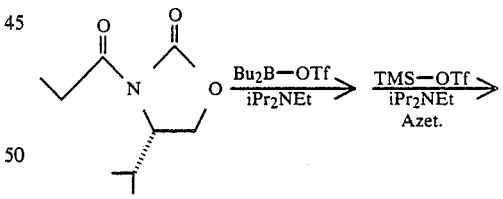

Twenty (20.0) mg (0.07 mmole) of pure alpha epimer from Example 3, is added at room temperature to 0.21 mmole (3 eq.), 0.4 ml of 0.5 NaOH in 0.5 ml of THF. The reaction is refluxed for 18 hours. The THF is removed in vacuo. The residue is taken up in a small amount of water. The aqueous layer is extracted with $CH_2Cl_2$ and acidified with HCl to pH=4. The organic layer is back extracted with $HOAc/CH_2Cl_2$. The residue from the organic basic layer, shows decomposition and the acid layer exhibits only trace of the alpha isomer by proton NMR spectroscopy.

EXAMPLE 6

Reaction:

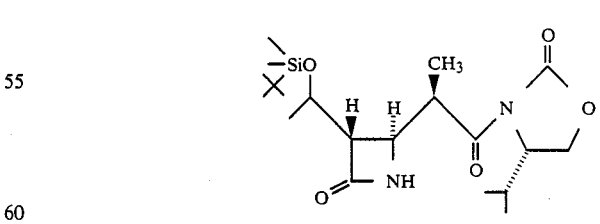

The (4S)-3-oxopropyl)-4-(1-methylethyl)-2-oxazolidinone (0.3821 g, 2.06 mmol) is dissolved in 2.0 mL of $CH_2Cl_2$ at −78° C. di-n-butylboryltriflate (Aldrich) (2.3 ml, 2.48 mmol) is added, followed by the $iPr_2NEt$ (Aldrich) (0.3205 g, 0.44 mL). After 10 min., the −78° C. bath is changed for a 0° C. bath. At 0° C., the azetidinone acetate (Azet.) compound (0.320 g, 1.11 mmol) is added via cannula to the boron enolate. Then, 5 equiv. of iPr₂NEt is added followed by the trimethylsilyl triflate. The course of the reaction is followed by HPLC (using 5% IPA/Hexane). After 5½ hr, 200 microliters of THS-OTf is added. To the reaction mixture is further added 5.0 ml saturated NaHCO₃ followed at 0° C. with 2 ml pH 7 buffer and 2 ml 30% H₂O₂ and stirred for a short period. The organic layer is extracted and the aqueous layer back extracted with (2×25 ml) CH₂Cl₂. The combined organic layers are dried over MgSO₄. LC assay after work up shows by 250 MHz proton NMR: a $\beta/\alpha$ ratio of 84/16 and a total conversion of 88%, based on starting azetidinone, the limiting reagent.

EXAMPLE 7

Reaction:

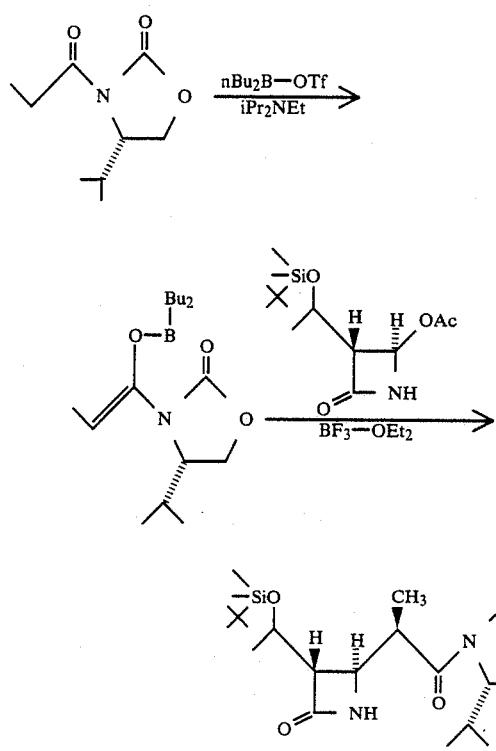

Following the general procedure of Example 6, but substituting BF₂.OEt₂ as the Lewis acid in place of trimethylsilyl triflate, a conversion of 92.5% to product and a $\beta/\alpha$ ratio of 68/32 is obtained as evidenced by 250 MHz proton NMR. To the crude mixture, is added 8 mL of 1.35M LiOH in H₂O in 8 mL of THF. The reaction temperature is raised to 80° C. for 1 hour and the crude concentrated and extracted with EtOAc. The $\beta/\alpha$ ratio of the resulting mixture of hydrolyzed acids of generalized Structure V, is 78/22 versus starting 68/32 of the crude evidencing an enrichment in the amount of beta isomer. The hydrolyzed oxazolidinone can be recovered from the EtOAc layer for use in recycle.

EXAMPLE 8

Stereoselective Generation of Boron and Silyl Enolates of 2-oxazolidinone Imides The general procedure for enolate formation involves reaction of 1.0 eq of Pr-Val-Ox 1 (the N-propionyl derivative of oxazolidinone prepared from L-valinol) and 1.10 eq of boryl triflate 2 in the presence of 1.20 eq of tertiary amine base in dry CH₂Cl₂ at temperature ranging from −78° to 25° C. (Table VIII).

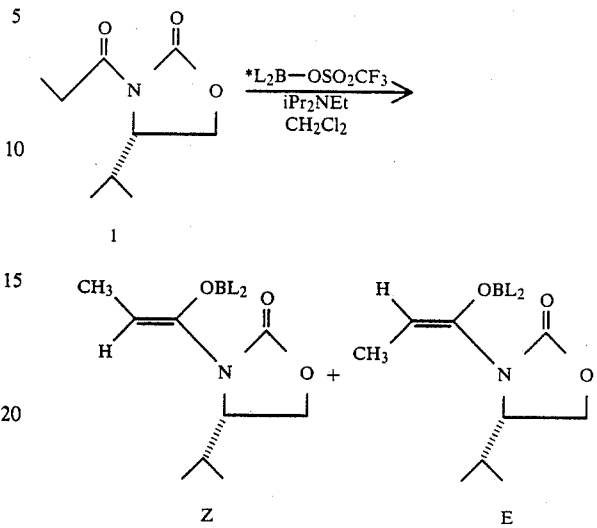

Note:
*L = nC₄H₉, C₂H₅

TABLE VIII

| Pr-Val-ox Enolate Formation | | |
|---|---|---|
| Boron or Silyl, Source | Conditions[a] | Ratios (Z/E)[b] |
| TMS—OTf | CCl₄, rt, Et₃N | 88/12 |
| TMS—Cl | THF, LDA, −78° C. | 99/1 |
| TMS—OTf | CCl₄, 0° C., Et₃N | 90/10 |
| nBu₂B—OTf[c] | iPr₂NEt, −78° C. | 89/11[d,e] |
| nBu₂B—OTf[c] | iPr₂NEt, rt | 88/12 |
| Et₂B—OTf | iPr₂NEt, −78° C. | 95/5[d] |
| Et₂B—OTf | iPr₂NEt, 0° C. | 90/10 |
| Et₂B—OTf | iPr₂NEt, −78° C. | 98/2[f] |
| Et₂B—OTf | iPr₂NEt, rt | 95/5 |

[a]All reactions carried out in CH₂Cl₂, except where noted.
[b]Enolate ratios determined by ¹³C NMR.
[c]1 M solution in CH₂Cl₂ from Aldrich.
[d]Z/E ratios constant up to R.T.
[e]Incomplete conversion (69%).
[f]Enolate ratio determined by ¹H NMR.

As is seen, in situ carbon-13 studies of enolate formation reveal complete conversion with greater than 95% stereoselectivity to the Z-isomer with enolate formation at −78° C., 0° C. or room temperature. No temperature dependance of the Z/E ratio is seen after complete generation. The boron enolate is found to be configurationally stable at 25° C. for up to 6 hours in the presence of iPr₂NEt.Tf/OH, TMS-OTf/iPr₂NEt/iPr₂NEt.Tf/OH and iPr₂NEt.Tf/OH/BF₃.OEt₂. Proton Nuclear Overhauser Effect (NOE) difference spectroscopy, sensitive to spatial proximity of nuclei independent of chemical bonding yields the spectral structure support confirming the Z configuration. Selective irradiation of the olefinic proton shows NOE transfer to the isopropyl methine at the oxazolidone C₄. Following this determination, carbon-13 NMR assignments are made for both boron enolate isomers as follows:

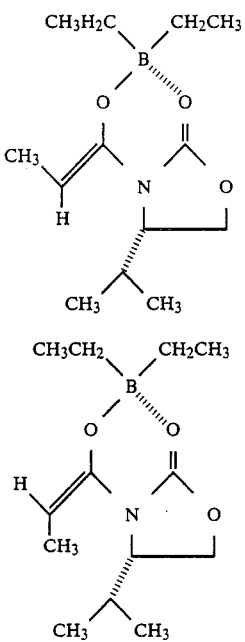

Z

E

'H-NMR assignments are made for both silyl end enol ether isomers as follows:

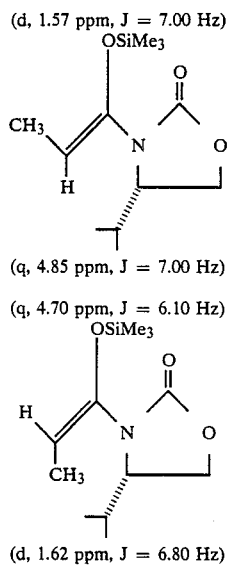

(d, 1.57 ppm, J = 7.00 Hz)

(q, 4.85 ppm, J = 7.00 Hz)

(q, 4.70 ppm, J = 6.10 Hz)

(d, 1.62 ppm, J = 6.80 Hz)

EXAMPLE 9

General Procedure for the Boron Enolate Condensation with 4-acetoxy-3-(1-t-butyl-dimethylsilyloxy)ethyl-2-azetidinone The condensations are run on a 0.5–10 mmol scale, with concentration of N-acyl oxazolidinone in methylene chloride of ca. 0.3M.

Into a dry, 3-necked flask equipped with a magnetic spin bar and thermometer is weighed 1.00 mmol of oxazolidinone. The flask is flushed with nitrogen and sealed with a rubber septum. Methylene chloride (3 ml) is added, and the solution cooled to −78° C. or at room temperature. Diethylboryl trifluoromethanesulfonate (2.20 mmole) is added, followed immediately by (2.40 mmole) of diisopropylethylamine. The solution is stirred for 30 minutes at 0° C., 1.0–2.0 equivalents of zinc bromide solution in tetrahydrofuran is added and stirred for 5 minutes followed by 1.00 mmole of the 4-acetoxy-3-(1-t-butyl-dimethylsilyloxy)ethyl-2-azetidinone in 10 ml of methylenechloride. After stirring the mixture for 6 hours at room temperature (T=20°–25° C.), at 0° C., pH=7 phosphate buffer (1 ml) is added followed by 1 ml of 30% hydrogen peroxide and the mixture is stirred for 15 minutes. The mixture is transferred to a separatory funnel containing aqueous sodium bicarbonate (5%) and is extracted with methylene chloride (3×10 ml). After drying the organic extracts over anhydrous magnesium sulfate and evaporation of the solvent in vacuo, a 95–100% mass recovery of products is obtained. The ratio of diastereomeric condensation adducts is determined by HPLC analysis of a sample of the crude product mixture as follows:

HPLC assay:

Altex Ultrasphere-octyl, 5μ, 25 cm×4.6 mm ID, acetonitrile:water:$H_3PO_4$, 70:30:0.1, v/v 1.1 ml/minute, 210 nm, sample injection volume:10 μl, sample concentration: 1 mg/component/ml. Retention times (min): Pr-Val-Ox, 4.32; β-Me-Ox, 12.01; α-Me-Ox, 16.42.

$^{13}C$ Assignments for β and α-Me oxazolidinone

β,α-Me-Ox

| Assignment | β ($^{13}C$ ppm) | α ($^{13}C$ ppm) |
|---|---|---|
| 2 | 167.8 | 168.00 |
| 3 | 60.9 | 63.00 |
| 4 | 54.7 | — |
| 5 | 51.8 | 52.3 |
| 6 | 174.3 | 175.0 |
| 7 | 65.0 | 65.5 |
| 8 | 22.5 | 22.7 |
| 5-CH$_3$ | 12.7 | 15.2 |
| 2' | 154.0 | 153.3 |
| 4' | 63.3 | 63.6 |
| 5' | 58.8 | 58.1 |
| 6' | 28.6 | 28.2 |
| 7'a | 14.4 | 14.7 |
| 7'b | 17.9 | 17.5 |
| (CH$_3$)$_3$C | 25.6 | 25.5 |
| (CH$_3$)$_3$C | 17.9 | 17.9 |

EXAMPLE 10

General Procedure for the Hydrolysis of Imides

To a solution of 1.00 mmole of imide in 1 ml of tetrahydrofuran is added 2 ml of a 1N aqueous LiOH solution. After stirring at room temperature for 3 hours, 5 ml of saturated brine is added. The solution is extracted (3×10 ml) with methylene chloride to remove the deacylated chiral oxazolidone (90% yield) which can be recovered for recycle. Acidification of the basic aqueous layer with 1N HCl to pH=4 and subsequent extraction with methylene chloride (3×10 ml) affords the desired acid in 70–85% yield. At pH=4, the acid precipitates and can be isolated via filtration.

EXAMPLE 11

Reaction:

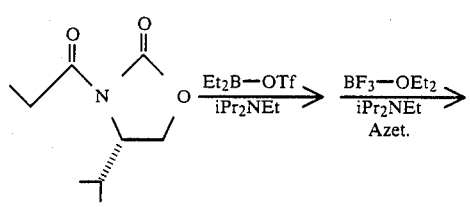

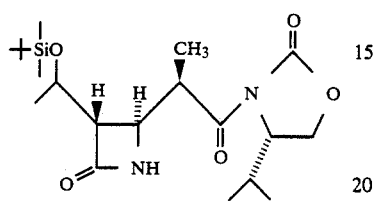

Procedure A

Following the general procedure of Example 6, into a dry 2-necked flask equipped with a magnetic spinbar was placed 0.2009 g (1.08 mmole) of N-propionyloxazolidinone. The flask was flushed with $N_2$ and sealed with a rubber septum. Methylene chloride (2 ml) was added, and the solution cooled to $-78°$ C. Diethylboryl trifluoromethanesulfonate (0.5933 g, 2.72 mmole) in 2 ml of $CH_2Cl_2$ was added followed immediately by 0.53 ml (0.3877 g, 3.00 mmole) of diisopropylethylamine. The light yellow solution was stirred at $-78°$ C. for 10 minutes and $BF_3.OEt_2$ (0.70 ml, 5.40 mmole) was added followed by the —OAc compound (219.1 mg, 0.762 mmole) in 5.0 ml of $CH_2Cl_2$. The reaction mixture was slowly warmed up to room temperature overnight. To the reaction mixture at 0° C. was added 1.0 ml of pH 7 phosphate buffer to quench the reaction followed by 1.0 ml of 30% aqueous hydrogen peroxide and the mixture was stirred at 0° C. for 1 hour. The mixture was transferred to a separating funnel containing aqueous $NaHCO_3$ and extracted with $CH_2Cl_2$ (3×20 ml). After drying the organic extracts over anhydrous $MgSO_4$ and evaporation of solvents in vacuo, the crude product crystallized. Yield was about 95%. HPLC analysis showed beta/alpha ratio of 84/16. By 250 MHz-$^1$H-NMR analysis, the ratio was 85/15.

EXAMPLE 12

Procedure B

Utilizing the same procedure described in Example 11 but at room temperature, the initial enolate and the resulting $BF_2$ enolate were generated, with the following quantities of reagents:

| | | |
|---|---|---|
| N—propionyoxazolidinone | 0.2425 g, | 1.309 mmole |
| $Et_2B$—OTf | 0.3140 g, | 1.440 mmole |
| $iPr_2NEt$ | 0.2031 g, | 1.571 mmole |
| $BF_3.OEt_2$ | 0.5575 g, | 3.928 mmole |
| —OAc | 0.3900 g, | 1.356 mmole, | a β/α ratio of 87/13 was obtained as shown by HPLC in 46% yield.

EXAMPLE 13

Reaction:
$^{19}$F-NMR Experiment

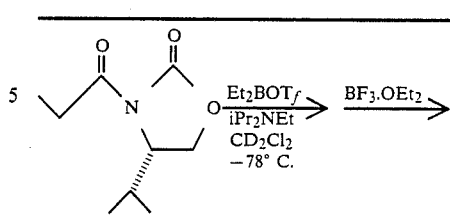

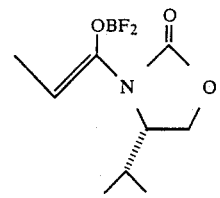

| | Reagents | | | |
|---|---|---|---|---|
| | Pr—Val—Ox | $Et_2B$—OTf | $iPr_2NEt$ | $BF_3.OEt_2$ |
| mol. wt. | 185.20 | 218.01 | 129.25 | 141.93 |
| mmole | 0.623 | 0.685 | 0.748 | 1.869 |
| grams | 115.3 mg | 149.4 mg | 96.7 mg | 265.3 mg |
| ml | — | 122 μl | 133 μl | 230 μl |
| Physical Constant | | d = 1.22 | d = 0.726 | d = 1.154 |
| Source | | | Aldrich | Aldrich |

Figure 2:
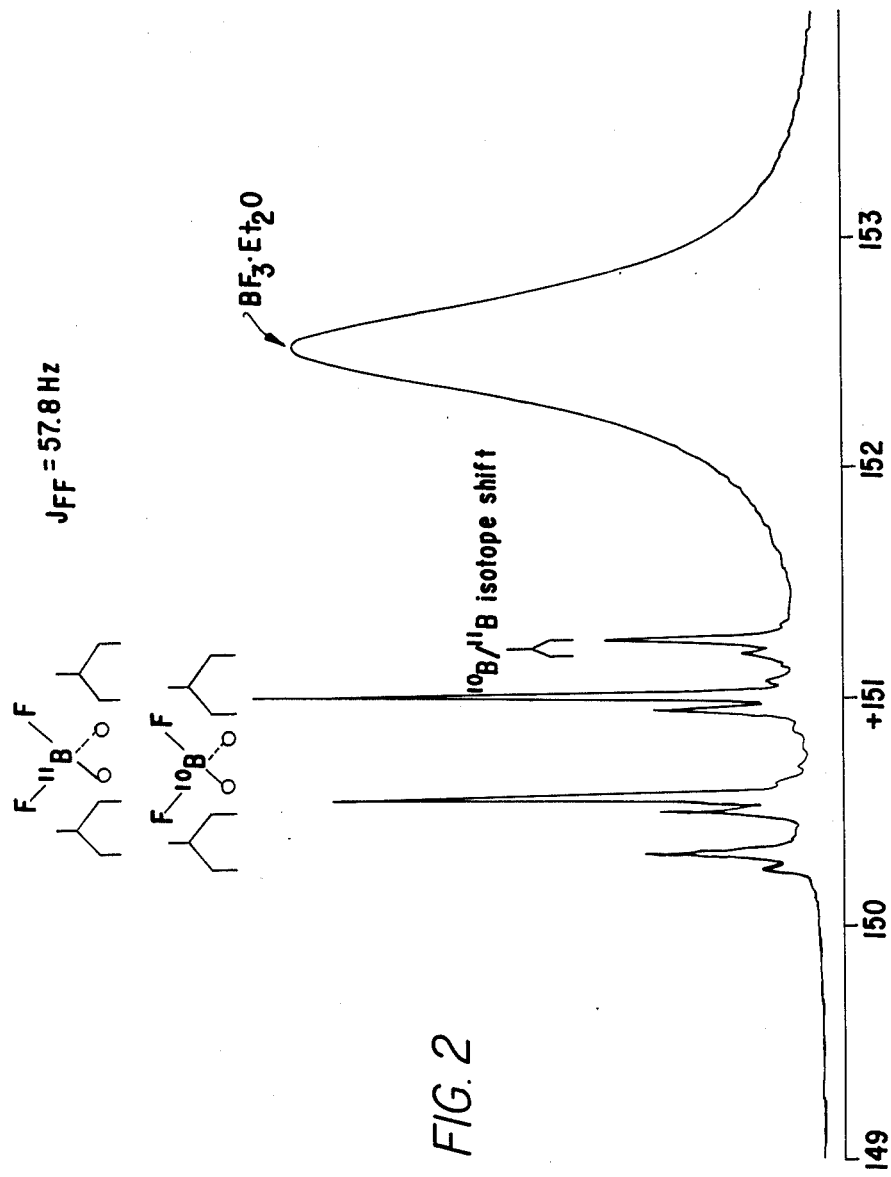
FIG. 2 is an expanded view of the 150-153 ppm region of FIG. 1.

Procedure:

To the N-propionyloxazolidinone (Pr-Val-Ox) in 2 ml of $CD_2Cl_2$ at $-78°$ C. was added the diethylboryltriflate ($Et_2B$-OTf) followed by the diisopropylethylamine ($iPr_2NEt$). The reaction mixture was stirred for ½ hour at $-78°$ C. The boron trifluoride etherate ($BF_3O$-$Et_2$) was added and warmed up to room temperature. $^{19}$F NMR was conducted at 250 MHz and the presence of the $BF_2$ enolate was shown by the pattern at 150.8 ppm (reference via internal standard $C_6F_6$, δ = 163 ppm) having a coupling constant of $J_{FF}=57.8$ Hz as shown in FIG. 1. FIG. 2 is an expanded view of the 150–153 ppm region.

EXAMPLE 14

Reaction:
$^{13}$C-NMR Experiment

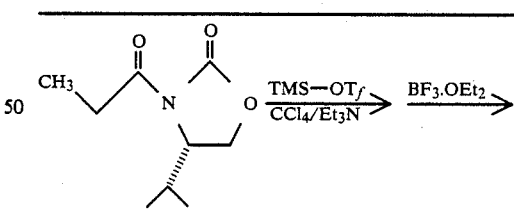

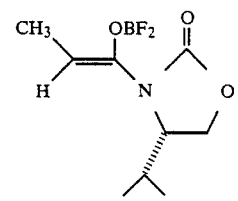

| | Reagents | | | |
|---|---|---|---|---|
| | Pr—Val—Ox | TMS—OTf | $Et_3N$ | $BF_3.OEt_2$ |
| mol. wt. | 185.20 | 222.26 | 101.19 | 141.93 |
| mmole | 1.99 | 2.99 | 3.98 | 5.97 |
| grams | 368.9 mg | 0.6641 | 0.4031 | 0.8473 |
| ml | — | 0.58 | 0.56 | 0.73 ml |

-continued

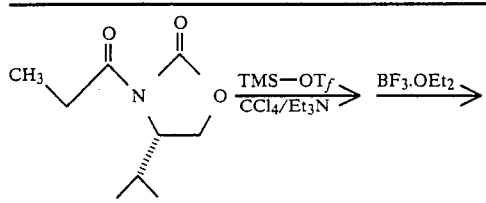

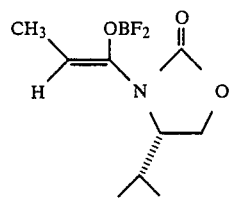

| Reagents | | | |
|---|---|---|---|
| Pr—Val—Ox | TMS—OTf | Et3N | BF3.OEt2 |
| Physical Constant | 1.0 equiv. | d = 1.150 1.5 equiv. | d = 0.726 2.0 equiv. | d = 1.154 |
| Source | | Aldrich | Eastman | Aldrich |

Procedure:

Utilizing the above indicated quantities, to the Pr-Val-Ox in 2 ml of CCl4 was added TMS-OTf followed by Et3N. Using D2O as external standard, $^{13}$C-NMR (100 MHz) of the enol was obtained showing the Z/E isomer ratio of 9:1. BF3.OEt2 was added and the resulting enolate was observed as a single isomer. The triplet obtained at 167–168 ppm evidenced dual fluorine incorporation into the enolate.

What is claimed is:

1. A compound of the formula:

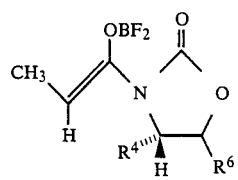

wherein $X^1$ and $X^2$ are independently O or S, $R^1$ is $C_1$-$C_4$ lower alkyl or alkoxyl, $R^4$, $R^5$ and $R^6$ are independently selected from H, $C_1$-$C_4$ alkyl, $C_7$-$C_{10}$ aralkyl, $C_6$-$C_{10}$ aryl, $C_7$-$C_{10}$ alkaryl, which can be substituted with —OH, —OR$^{10}$, —SH, SR$^{10}$, where $R^{10}$ is $C_1$-$C_4$ alkyl, with the proviso that $R^4$ and $R^5$ are not identical.

2. The compound of claim 1 wherein $R^4$ is sterically larger than $R^5$.

3. The compound of claim 2 wherein $R^1$ is beta-methyl.

4. The compound of claim 2 wherein $R^4$ and $R^6$ are independently selected from $C_1$-$C_4$ linear or branched alkyl, $C_7$-$C_{10}$ aralkyl or $C_4$-$C_{10}$ aryl.

5. The compound of claim 1 wherein $X^1$ and $X^2$ are oxygen.

6. The compound of claim 1 of the formula:

wherein $R^4$ is isopropyl or phenyl and $R^6$ is respectively, hydrogen or methyl.

* * * * *